US006383763B1

(12) United States Patent
Wallis

(10) Patent No.: US 6,383,763 B1
(45) Date of Patent: *May 7, 2002

(54) DETECTION OF MYCOBACTERIA

(75) Inventor: Robert S. Wallis, Cleveland, OH (US)

(73) Assignee: Case Western Reserve University, Cleveland, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/690,347

(22) Filed: Jul. 26, 1996

(51) Int. Cl.[7] .................... G01N 33/554; A61K 39/395; A61K 39/40; A61K 39/42
(52) U.S. Cl. ................ 435/7.32; 424/141.1; 424/150.1; 424/163.1; 424/178.1; 435/7.1
(58) Field of Search ................................ 435/7.32, 7.1; 424/141.1, 150.1, 163.1, 178.1

(56) References Cited

FOREIGN PATENT DOCUMENTS

WO 92/14155 8/1992 ......... G01N/33/569

OTHER PUBLICATIONS

Salata et al "Purification & characterization of the 30,000 dalton native Antigen of M. Tuberculosis & characterization of 6 monoclonal antibodies" J. Lab. Clin. Med 118:589–92 1991.*

DeWit et al "Nucleotide sequence of the 85 B–protein gene of M. Bovis BCG and M. tuberculosis" DNA Seq. 4:267–220, 1994.*

Sippola et al "*M. avium* antigenuria in patients w/aids & Disseminated *M. avium* disease" J. InF. Dis. 168:466–468, 1993.*

Kochi, The global tuberculosis situation and the new control strategy of the World Health Orgainzation, *Tubercle* 72:1–6 [1991].

Nolte and Metchock, "Mycobacterium," in *Manual of Clinical Microbiology*, Sixth Edition, ASM Press: Washington, [1995],pp. 400–437.

World Health Organizaiton TB Programme, quoted in "TB: A Global Emergency," *WHO*, 1994: Copy Not Provided.

Snider et al., "Global Burden of Tuberculosis," B.R. Bloom (ed.), *Tuberculosis: Pathogenesis, Protection and Control*, American Society for Microbiology, Washington, D.C., [1994], pp. 3–11.

Joklik et al. (eds.), *Zinsser Microbiology*, 18th ed., Appleton–Centry Crofts, Norwalk, CT, [1984], p. 564.

Thoen, "Tuberculosis in Wild and Domestic Mammals,"in B.R. Bloom (ed.) *Tuberculosis: Pathogenesis, Protection and Control*, American Society for Microbiology, Washington, D.C. [1994], pp. 157–162.

Thorel et al., Numerical taxonomy of mycobactin–dependnet mycobacteria, emended description of *Mycobacterium avium*, and description of *Mycobacterium avium* subsp. avium, subsp nov. *M. avium* subsp. paratuberculosis, subsp. nov., and *Mycobacterium avium* subsp. silvaticum subsp nov., *Int. J. Syst. Bacteriol.*, 40:254–260 [1990].

Nightingale et al., "Incidence of *M. avium intracellulare* Complex Bacteraemia in HIV–positive Patients," J. Infect Dis., 165:108–25 [1992].

Fry et al., "Epidemiology of Infection by Nontuberculous Mycobacteria. VI. Identification and Use of Epidemiologic Markers for Studies of *Mycobacterium avium, M. intracellular*, and *M. scrofulaceum*," *Am. Rev. Respir. Dis.*, 134:39–43[1986].

Peterson et al., "*M. Avium* Complex (Mac) Disease in Hiv–infected Patients Is a Uniform Infection of Bone Marrow That Does Not Correlate with the Level of Infection in Blood," *Natl. Conf. Hum. Retrovir. Rel. Pathogens* 2:56 [1995].

American Thoracic Society and Centers for Disease Control, "Treatment of Tuberculosis and Adults and Children," *Am. Rev. Respir. Dis.*, 134:355–363 [1986].

Centers for Disease Control, "National MDR–TB Task Force, National Action Plan to Combant Multidrug–resistant Tuberculosis," *Morbid. Mortal. Wkly. Rept.*, 41:1–48 [1992].

Rastogi et al., "Enhancement of Drug Susceptibility of *Mycobacterium avium* by Inhibitors of Cell Envelope Synthesis," *Antimicrob. Agents Chemother.*, 34:759–764 [1990].

Ratnam et al., "Simplified Acetylcysteine–alkali Digestion–decontamination Procedure for Isolation of Mycobacteria from Clinical Specimens," *J. Clin. Microbiol.* 25:1428–1438 [1987].

Centers for Disease Control, "Recommendations on Prophylaxis and Therapy for Disseminated *Mycobacterium avium* complex for Adults and Adolescents Infected with Human Immunodeficiency Virus," *Morbid. Mortal. Wkly Rept.*, 42(RR):14–20 [1993].

(List continued on next page.)

Primary Examiner—Rodney P Swartz
(74) *Attorney, Agent, or Firm*—Medlen & Carroll, LLP

(57) ABSTRACT

The present invention is directed to methods and compositions for the detection of infection and disease due to members of the genus Mycobacterium. In particular, the present invention is well-suited to the detection and identification of patients with disease or infection due to *M. tuberculosis* or MAC.

12 Claims, 23 Drawing Sheets

OTHER PUBLICATIONS

Havlik et al., "Disseminated *Mycobacterium avium* Complex Infection: Clinical Identification and Epidemiologic Trends," *J. Infect. Dis.*, 165:577–580 [1992].

Torriani et al., "Autopsy Findings in AIDS Patients with *M. avium* complex Bacteremia," *J. Infect. Dis.*, 170:1601–5 [1994].

Master (section editor) Section 3. "Mycobacteriology," in H.E. Isenberg (editor in chief), *Clinical Microbiology Procedures Handbook*, vol. 1, 3.01–3.16.4 [1994].

Snider, "The Tuberculin Skin Test," *Ann. Rev. Resp. Dis.*, 125(Suppl.):108–118 [1982].

Bardana, "Universal Occurrence of Antibodies to Tubercle *Bacilli in sera* From Non–tuberculous and tuberculous individuals," *Clin. Exp. Immunol.*, 13:65–77 [1973].

Daniel and Debanne, "The Serodiagnosis of Tuberculosis and other Mycobacterial Disease by Enzyme–linked Immnosorbent Assay," *Am. Rev. Resp. Dis.*, 158:678–680 [1987].

Wilkins et al., "A Rapid, Simple Enzyme Immunoassay for Detection of Antibody to Individual Epitopes in the Serodiagnosis of Tuberculosis," *Eur. J. Clin. Microbiol. Infect. Dis.*, 10:559–563 [1991].

Benjamin et al., "Serodiagnosis of Tuberculosis Using the Enzyme–Linked Immunoabsorbent Assay (ELISA) of Antibody to *Mycobacterium tuberculosis* Antigen $5^{1-3}$," *Amer. Rev. Respir. Dis.*, 126:1013–1016 [1982].

Maes et al., "Development of an Enzyme Immunoassay for the Serodiagnostic of Tuberculosis and Mycobacterioses," *Med. Microbiol. Immunol.*, 178:323–335 [1989].

Kalish et al., "Use of an Enzyme–Linked Immunosorbent Assay Technique in the Differential Diagnosis of Active Pulmonary Tuberculosis in Humans," *J. Infect. Dis.*, 147:523–530 [1983].

Nassau et al., "The Detection of Antibodies ot *Mycobacterium tuberculosis* by Microplate Enzyme–Linked Immunosorbent Assay (ELISA)," *Tubercle*, 57:67–70 [1976].

Garcia–Carreno, "Enzyme Immunoassay Using BCG in Serodiagnosis of Pulmonary Tuberculosis," *J. Hyg.*, 97:483–487 [1986].

Hernandez et al., "Sensitive Enzyme Immunoassay for Early Diagnosis of Tuberculous Meningitis," *J. Clin. Microbiol.*, 20:533–535 [1984].

McDonough et al., "Microplate and Dot Immunoassays for the Serodiagnosis of Tuberculosis," *J. Lab Clin. Med.*, 120:318–322 [1992].

Sada et al., "An ELISA for the Serodiagnosis of Tuberculosis Using a 30,00–Da Native Antigen of *Mycobacterium tuberculosis*," *J. Infect. Dis.*, 162:928–931 [1990].

Mathai et al., "Rapid Diagnosis of Tuberculous Meningitis with a Dot Enzyme Immunoassay to Detect Antibody in Cerebrospinal Fluid," *Eur. J. Clin. Microbiol. Infect. Dis.*, 10:440–443 [1991].

Turneer et al., "Humoral Immune Response in Human Tuberculosis: Immunoglobulins G, A, and M Directed Against the Purified P32 Protein Antigen of *Mycobacterium bovis* Bacillus Calmette–Guerin," *J. Clin. Microbiol.*, 26:1714–1719 [1988].

Kaushik et al., "Serodiagnostic Efficiency of Phospholipid Associated Protein of *Mycobacterium tuberculosis* $H_{37}Rv$," *Med. Microbiol. Immunol.*, 182:317–327 [1993].

Kumar et al., "Identification of a 25–Kilodalton Protein of *Mycobacterium bovis* BCG to Distinguish BCG Strains from *Mycobacterium tuberculosis*," *J. Clin. Microbiol.*, 34:224–226 [1996].

Chandramuki et al. "Levels of Antibody to Defined Antigens of *Mycobacterium tuberculous* in Tuberculous Meningitis," *J. Clin. Microbiol*, 27:821–825 [1989].

Near et al., "Use of Serum Antibody and Lysozyme Levels for Diagnosis of Leprosy and Tuberculosis," *J. Clin. Microbiol.*, 30:1105–1110 [1992].

Miöner et al., "Diagnosis of Tuberculous Meningitis: A Comparative Analysis of 3 Immunoassays, An Immune Complex Assay and the Polymerase Chain Reaction," *Tubercle Lung Dis.*, 76: 381–386 [1995].

Jackett et al., "Specificity of Antibodies to Immunodominant Mycobacterial Antigens in Pulmonary Tuberculosis," *J. Clin.Microbiol.*, 26:2313–2318 [1988].

Gal et al., "The Clinical Laboratory Evaluation of Cryptococcal Infections in the Acquired Immunodeficiency Syndrome," *Diagn. Microbiol. Infect. Dis.*, 7:249–54 [1987].

Wheat et al., "Diagnosis of Disseminated Histoplasmosis by Detection of *Histoplasma capsulatum* Antigen in Serum and Urine Specimens," *N. Engl. J. Med.* 314:83–8 [1986].

Young et al., "Detection of Phenolic Glycolipid I in sera from Patients with Lepromatous Leprosy," *J. Infect. Dis.*, 152:1078–81 [1985].

Sada et al., "Detection of Mycobacterial Antigens in Cerebrospinal Fluid of Patients with Tuberculous Meningitis by Enzyme–linked Immunosorbent Assay," *Lancet* 2:651–2 [1983].

al Orainey et al., "Detection of Mycobacterial Antigens in Sputum by an Enzyme Immunoassay," *Eur. J. Clin. Microbiol. Infect. Dis.*, 11:58–61 [1992].

Kansal et al., "Detection of Mannophosphoinositide Antigens in Sputum of Tuberculosis Patients by Dot Enzyme Immunoassay," *Med. Microbiol. Immunol. Berl.*, 180:73–8 [1991].

Yanez et al., "Determination of Mycobacterial Antigens in Sputum by Enzyme Immunoassay," *J. Clin. Microbiol.*, 23:822–5 [1986].

Kadival et al., "Radioimmunoassay of Tuberculous Antigen, "*Indian J. Med. Res.*, 75:765–70 [1982].

Chandramuki et al., "Detection of Mycobacterial Antigen and Antibodies in the Cerebrospinal Fluid of Patients with Tuberculous Meningitis," *J. Med. Microbiol.*, 20:239–247 [1985].

Cambiaso et al., "Immunological Detection of Mycobacterial Antigens in Infected Fluids, Cells and Tissues by Latex Agglutination—Animal Model and Clinical Application," *J. Immunol. Meth.*, 129:9–14 [1990].

Daniel, "Rapid Diagnosis of Tuberculosis: Laboratory Techniques Applicable in Developing Countries," *Rev. Infect. Dis.*, 2(Supplement 2): S471–S478 ([1989].

Raja et al., "Specific Detection of Mycobacterium Tuberculosis in Radiometric Cultures by Using an Immunoassay for Antigen 5," *J. Infect. Dis.*, 158:468–70 [1988].

Raja et al., "The Detection by Immunoassay of Antibody to Mycobacterial Antigens and Mycobacterial Antigens in Bronchoalveolar Lavage Fluid from Patients with Tuberculosis and Control Subjects," *Chest* 94:133–137 [1988].

Schoningh et al., "Enzyme Immunoassay for Identification of Heat–killed Mycobacteria Belonging to the Mycobacterium tuberculosis and *Mycobacterium avium* Complexes and Derived from Early Cultures," *J. Clin. Microbiol.*, 28:708–13 [1990].
Drowart et al., "Detection of Mycobacterial Antigens Present in Short–term Culture Media Using Particle Counting Immunoassay," *Am. Rev. Respir. Dis.*, 147:1401–6 [1993].
Yamamura et al., "Biology of the Mycobacterioses. Chemical and Immunological Studies on Peptides and Polysaccharides from Tubercle bacilli," *Ann. NY Acad. Sci.*, 154:88–97 [1968].
Chaparas et al., "Comparison of Lymphocyte Transformation, Inhibition of Macrophage Migration and Skin Tests Using Dailyzable and Nondialyzable Tuberculin Fractions from *Mycobacterium Bovis* (Bcg)," *J. Immunol.*, 107:149–53 [1971].
Affronti et al., "Some Early Investigations of Mycobacterium Tuberculosis," *Am. Rev. Respir. Dis.*, 92:1–8 [1995].
Daniel et al., "Reactivity of Purified Proteins and Polysaccharides from *Mycobacterium tuberculosis* in Delayed Skin Test and Cultured Lymphocyte Mitogenesis Assays," *Infect. Immun.*, 9:44–7 [1974].
Chaparas et al., "Tuberculin–active Carbohydrate That Induces Inhibition of Macrophage Migration but not Lymphocyte Transformation," *Science* 170:637–9 [1970].
Janicki et al., "A Reference System for Antigens of *Mycobacterium Tuberculosis,*" *Am. Rev. Respir. Dis.*, 104:602–4 [1971].
Daniel et al.,"Immunobiology and Species Distribution of Mycobacterium Tuberculosis Antigen 5," *Infect. Immun.*, 24:77–82 [1979].
Daniel et al., "Demonstration of a Shared Epitope Among Mycobacterial Antigens Using a Monoclonal Antibody," *Clin. Exp. Immunol.*, 60:249–58 [1985].
Daniel et al., "Specificity of *Mycobacterium tuberculosis* Antigen 5 Determined With Mouse Monoclonal Antibodies," *Infect. Immun.*, 45:52–5 [1984].
Closs et al., "The Antigens of *Mycobacterium Bovis*, Strain Bcg, Studied by Crossed Immunoelectrophoresis: a Reference System," *Scand. J. Immunol.*, 12:249–63 [1980].
Sippola et al., "*Mycobacterium Avium* Antigenuria in Patients with Aids and Disseminated *M. Avium* Disease," *J. Infect. Dis.*, 168:466–8 [1993].
Jones et al., "Relationship of the Manifestations of Tuberculosis to Cd4 Cell Counts in Patients with Human Immunodefiency Virus Infection," *Am. Rev. Respir. Dis.*, 148:1292–1297 [1993].
Santos et al., "Liver Disease in Patients with Human Immunodeficiency Virus Infection. Study of 100 Biopsies," *Rev. Clin. Esp.*, 193:115–8 [1993].
Pithie et al., "Fine–needle Extrathoracic Lymph–node Aspiration in Hiv–associated Sputum–negative Tuberculosis," *Lancet* 340:1504–5 [1992].
Barnes et al., "Tuberculosis in the 1900s," *Ann. Intern. Med.*, 199:400–10 [1993].
Brindle et al., "Quantitative Bacillary Response to Treatment in Hiv–associated Pulmonary Tuberculosis," *Am. Rev. Respir. Dis.*, 147:958–61 [1993].
Grange, "The Rapid Diagnosis of Paucibacillary Tuberculosis," Tubercle, 70:1–4 [1989].

Daniel et al., "Reduced Sensitvity of Tuberculosis Serodiagnosis in Patients with Aids in Uganda," *Tuber. Lung Dis.*, 75:33–7 [1994].
Villarino et al., "Management of Persons Exposed to Multidrug–resistant Tuberculosis," *Morb. Mort. Wkly. Rep.*, 41(RR–11):61–71 [1992].
Selwyn et al., "A Prospective Study of the Risk of Tuberculosis among Intravenous Drug Abusers with Human Immunodeficiency Virus Infection," *N. Eng. Med.*, 320:545–550 [1989].
Heifets and Good, "Current Laboratory Methods for the Diagnosis of Tuberculosis," in B.R. Bloom (ed.) *Tuberculosis: Pathogenesis, Protection and Control*, American Society for Microbiology, Washington, D.C. [1994], pp. 85–110.
Chan et al., "The Early Bactericidal Activity of Rifabutin Measured by Sputum Viable Counts in Hong Kong Patients with Pulmonary Tuberculosis," *Tubercle* 1992;33–8 [1992].
Jindani et al., "The Early Bactericidal Activity of Drugs in Patients with Pulmonary Tuberculosis," *Am. Rev. Respir. Dis.*, 121:939–49 [1980].
Torriani et al., "Autopsy Findings in Aids Patients with *M. Avium* Complex Bacteremia," *J. Infect. Dis.*, 170:1601–5 [1994].
Kemper et al., "Transient Bacteremia Due to *M. Avium* Domplex in Patients with Aids," *J. Infect. Dis.*, 170:488–93 [1994].
Andersen et al., "Proteins Released from *Mycobacterium Tuberculosis* During Growth," *Infect. Immun.*, 59:1905–10 [1991].
Tasaka et al., "Specificity and Distribution of Alpha Antigens of *Mycobacterium Avium–intracellulare, Mycobacterium Scrofulaceum*, and Related Species of Mycobacteria," *Am. Rev. Respir. Dis.*, 1985;132:173–4 [1985].
Matsuo et al., "Dloning and Expression of the Gene for the Dross–reactive Alpha Antigen of *Mycobacterium Kansasii,"* *Infect. Immun.*, 58:550–6 [1990].
Matsuo et al., "Dloning and Expression of the *Mycobacterium Bovis* Bcg Gene for Extracellular Alpha Antigen," *J Bacteriol.*, 170:3847–54 [1988].
Ohara et al., "Dloning and Sequencing of the Gene for Alpha Antigen from *M. Avium* and Mapping of B–cell Epitopes," *Infect. Immun.*, 61:1173–9 [1993].
DeWit et al., "Nucleotide Sequence of the 85b–protein Gene of *M. Bovis* Bcg and *M. Tuberculosis:* Dna Sequence," *J. DNA Seq. Map.*, in press. [1996]; Dopy Not Provided.
Ohara et al., "Dloning and Sequencing of the Gene for Alpha Antigen from *M. Avium* and Mapping of B–cell Epitopes," *Infect. Immun.*, 61:1173–9 [1993].
Filley et al., "Identification of an Antigenic Domain on *Mycobacterium Leprae* Protein Antigen 85b, Which Is Specifically Recognized by Antibodies from Patients with Leprosy," *J Infect. Dis.*, 169:162–9 [1994].
Sippola et al., "*Mycobacterium Avium* Antigenuria in Patients with Aids and Disseminated *M. Avium* Disease," *J. Infect. Dis.*, 168:466–8 [1993].
Drowart et al., "Isoelectrophoretic Dharacterization of Protein Antigens Present in Mycobacterial Dulture Filtrates and Recognized by Monoclonal Antibodies Directed Against the *Mycobacterium Bovis* Bcg Antigen 85 Domplex," *Scand J. Immunol.*, 36:697–702 [1992].
Daniel, "From the Dhicago Meetings—the Rapid Diagnosis of Tuberculosis: a Selective Review," *J. Lab. Dlin. Med.*, 116:277–282 [1990].

Grange, "The Humoral Immune Response in tuberculosi: Its Nature, Biological Role and Diagnostic Usefulenss," *Adv. Tuberc. Res.,* vol. 21:1–78 [1978].

Ellner and Wallis, "Immunologic Aspects of Mycobacterial Infections," *Rev. Infect Dis.,* 2(Supplement 2): S455–S459 [1989].

Krambovitis et al., "Improved Serodiagnosis of Tuberclosis Using Two Assay Test," *J. Dlin. Pathol.,* 39: 779–785 [1986].

Praputpittaya and Ivanyi, "Detection of an Antigen (MY4) Dommon to *M. tuberculosis* and *M. leprae* by 'Tandem' Immunoassay," *J. Immunol. Meth.,* 79:149–157 [1985].

Miorner et al., "Diagnosis of Tuberculous Meningitis: A Domparative Analysis of 3 Immunoassays, An Immune Domplex Assay and the Polymerase Dhaim Reaction," *Tubercle Lung Dis.,* 76: 381–386 [1995].

Mazurek et al., Detection of *Mycobacterium tuberculosis* in Derebrospinal Fluid Following Immunomagnetic Enrichment, *J. Dlin. Microbiol.,* 34: 450–453 [1996].

Straus et al., "Dlinical Applications of the Radioimmunoassay of Secretory Tuberculoprotein," *Proc. Natl. Acad. Sci. USA,* 78:3214–3217 [1981].

Straus and Wu, Radioimmunoassay of Tuberculoprotein Derived From *Mycobacterium tuberculosi, Proc. Natl. Acad. Sci. USA,* 77:4301–4304 [1980].

Sockett et al., "Evaluation of Four Serological Tests for Bovine Paratuberculosis," *J. Klin. Microbiol.,* 30:1134–1139 [1992].

De Kesel et al., Dloning and Expression of Protions of the 34–Kilodalton–Protein Gene of *Mycobacterium paratuberculosis:* Its Application to Serological Analysis of Johne's Disease, *J. Dlin. Microbiol.,* 31:947–954 [1993].

Dollins et al., "Evaluation of a Dommercial Enzyme–Linked Immunosorbent Assay for Johne's Disease," *J. Dlin. Microbiol.,* 29:272–276 [1991].

* cited by examiner a  b  c

Alpha antigen capture ELISA
spike recovery

Detection of TB alpha antigen
HIV- subjects

Detection of urinary alpha antigen
HIV+ subjects

ELISA for alpha antigen
in mycobacterial culture filtrates

Urinary alpha antigen
HIV- subjects

Urinary alpha antigen
HIV+ subjects

Sputum alpha antigen mean initial value: 27±13 pg/ml
t/2 (half life): 0.6 days mean initial value: 41.4±11 pg/ml
t/2 (half life): 5.6 days Sputum alpha antigen mean initial value: 41.4±11 pg/ml
t/2 (half life): 5.6 days

FUGURE 19

Comparison of amino acid sequences of alpha antigens of M. avium and M. tuberculosis

```
AV:   1 MTDLSEKVRA WGRRLLVGAA AAVTLPGLIG LAGGAATANA FSRPGLPVEY LQVPSAGMGR DIKVQFQSGG
TB:   1 MTDVSRKIRA WGRRLMIGTA AAVVLPGLVG LAGGAATAGA FSRPGLPVEY LQVPSPSMGR DIKVQFQSGG

AV:  71 NGSPAVYLLD GLRAQDDYNG WDINTPAFEW YYQSGLSVIM PVGGQSSFYA DWYQPACGKA GCSTYKWETF
TB:  71 NNSPAVYLLD GLRAQDDYNG WDINTPAFEW YYQSGLSIVM PVGGQSSFYS DWYSPACGKA GCQTYKWETF 147                                    181
AV:141 LTSELPSYLA SNKGVKRTGN AAVGISMSGS SAMILAVNHP DQFIYAGSLS ALLDPSQGMG PSLIGLAMGD
TB:141 LTSELPQWLS ANRAVKPTGS AAIGLSMAGS SAMILAAYHP QQFIYAGSLS ALLDPSQGMG PSLIGLAMGD

229
AV:211 AGGYKADAMW GPSSDPAWQR NDPSLHIPEL VGHNTRLWLY CGNGTPSELG GANMPAEFLE NFVRSSNLKF
TB:211 AGGYKAADMW GPSSDPAWER NDPTQQIPKL VANNTRLWVY CGNGTPNELG GANIPAEFLE NFVRSSNLKF

AV:281 QDAYNGAGGH NAVFNFNANG THSWEYWGAQ LNAMKPDLQG TLGASPGGGG
TB:281 QDAYNAAGGH NAVFNFPPNG THSWEYWGAQ LNAMKGDLQS SLGAG
```

FIGURE 20

Western blot of *M. avium* filtrate with serum of mice immunized with alpha antigen peptides 147 and 229 on polystyrene microparticles.

mwm    147    229

Western blot of filtrates of *M. avium* and
*M. tuberculosis* using goat *M. intracellulare* antisera, 1988.

FIGURE 21A — Kris: mwm, avi, tb ← alpha

FIGURE 21B — Kris-TB adsorbed: mwm, avi, tb; 22.5 →

FIGURE 21C — Jane: mwm, avi, tb ← alpha

FIGURE 22

Western blot of filtrates of *M. avium* and *M. tuberculosis* culture filtrates, using Kris serum, 1996

FIGURE 22A

TB AVI TB AVI

Preabsorbed W/TB

DETECTION OF MYCOBACTERIA

This application was made with government support under A145244 awarded by the National Institutes of Health. The government has certain rights in the invention.

FIELD OF THE INVENTION

The present invention relates to the detection and diagnosis of infection and disease due to the mycobacteria, especially *Mycobacterium tuberculosis* and other mycobacteria commonly associated with disease in immunocompromised patients including those with acquired immunodeficiency syndrome (AIDS). The present invention is suited for rapid screening of large populations for the presence of *M. tuberculosis* carriers, as well as diagnosing and monitoring disease or infection in patients who present at healthcare or public health facilities.

BACKGROUND OF THE INVENTION

Organisms within the genus Mycobacterium include obligate parasites, saprophytes, and opportunistic pathogens. Most species are free-living in soil and water, but for species such as *M. tuberculosis* and *M. leprae*, the causative agents of tuberculosis and leprosy respectively, the major ecological niche is the tissue of humans and other warm-blooded animals.

Despite the fact that most mycobacteria do not cause disease, a relatively small group of organisms within the genus is responsible for a large percentage of human morbidity and mortality worldwide. Tuberculosis remains a major global health problem, with nearly one third of the world's population infected. Indeed, tuberculosis is the leading cause of death due to a single infectious agent. In addition. the World Health Organization estimates that worldwide, there are 8–10 million new cases and over 3 million deaths directly attributed to this disease reported worldwide (A. Kochi, The global tuberculosis situation and the new control strategy of the World Health Organization, Tubercle 72:1–6 [1991]).

*M. tuberculosis* is exceptionally easily transmitted, as it is carried in airborne particles termed "droplet nuclei," produced when a patient with active tuberculosis coughs. These particles are from $1–5\mu$ in size, and are readily suspended in air currents. Infection occurs when droplet nuclei are inhaled and reach the terminal airways of the new host's lungs. Usually, the host immune response limits the multiplication and spread of the organism, although some organisms may remain dormant, but viable, for many years post-infection. Individuals infected with *M. tuberculosis* but without disease, usually have a positive skin test (i.e., with purified protein derivative [PPD]), but are asymptomatic and generally not infectious. However, latently infected individuals have a 10% risk for developing active tuberculosis at some point during their life; the risk is greatest within the first two years post-infection. For HIV-positive individuals, the risk is much greater, with the risk at 10–15% per year for progression to active disease (F. S. Nolte and B. Metchock, "Mycobacterium," in *Manual of Clinical Microbiology*, Sixth Edition, ASM Press: Washington, [1995],pp. 400–437).

Co-infection with human immunodeficiency virus (HIV) and *M. tuberculosis* has resulted in staggering increases in tuberculosis rates—as much as 200% in the past 4 years, particularly in impoverished countries with few resources available to control this epidemic. Yet even western industrialized countries have reported increases in tuberculosis rates of from 2 to 14% per year during the past decade (World Health Organization TB Programme, quoted in "TB: A Global Emergency," WHO, 1994). These increases, coupled with the emergence of multi-drug-resistant strains, and the recognition that tuberculosis is one HIV-related opportunistic infection which can be readily transmitted to HIV-uninfected persons, have focused the attention of physicians, researchers, and public health workers on issues related to tuberculosis control, particularly in terms of development of improved vaccines for tuberculosis prevention and improved tests for tuberculosis diagnosis.

In the United States, aggressive approaches to tuberculosis control including isolation of patients in facilities such as sanitoria and the development of drugs effective against *M. tuberculosis* resulted in a steady decline in the incidence of tuberculosis until about 1985, when the trend reversed and the reports of new tuberculosis cases began to increase. If the trend for the years 1980–1984 is used to calculate the number of expected cases, the Centers for Disease Control and Prevention (CDC) estimated that between 1985–1992, approximately 51,000 excess cases have accumulated (D. E. Snider et al., "Global burden of tuberculosis," in B. R. Bloom (ed.), *Tuberculosis: Pathogenesis, Protection and Control*, American Society for Microbiology, Washington, D.C., [1994], pp. 3–11).

A number of contributory factors are likely to be responsible for the observed increase in tuberculosis cases, including the AIDS pandemic, immigration from areas with high endemicity of tuberculosis, general deterioration of the health care infrastructure, transmission in high-risk environments (e.g., homeless shelters), and the increase in the number of multi-drug resistant *M. tuberculosis* strains (Nolte and Metchock, supra, at p. 400). Unless the effectiveness and availability of methods and drugs to detect and treat tuberculosis do not substantially improve, it is expected that over 30 million deaths and 90 million new cases of tuberculosis will occur in the years between 1990–2000 (Snider et al., at p. 10).

Although it is the major cause, organisms other than *M. tuberculosis* are sometimes associated with tuberculosis in humans and other animals. These organisms are included in the "*M. tuberculosis* complex," which includes *M. bovis, M. africanum,* and *M. microti,* as well as *M. tuberculosis. M. bovis* causes tuberculosis in cattle, humans and other primates, carnivores (e.g., dogs and cats), swine, parrots, and some birds of prey. Human disease is virtually indistinguishable from that caused by *M. tuberculosis,* and is treated in a similar manner (Nolte and Metchock, supra, at 402). Similarities between *M. bovis* and *M. tuberculosis* led to the development of the bacillus of Calmette-Guérin (BCG) an attenuated form of *M. bovis,* as a vaccine against tuberculosis in many parts of the world (See e.g., W. K. Joklik et al. (eds.), *Zinsser Microbiology,* 18th ed., Appleton-Century Crofts, Norwalk, Conn., [1984], p. 564).The human health problems associated with *M. bovis* were largely responsible for the development of methods for the pasteurization of milk and the adoption of compulsory pasteurization in the early 1900s (See, C. O. Thoen, "Tuberculosis in wild and domestic mammals," in B. R. Bloom (ed.) *Tuberculosis: Pathogenesis, Protection and Control,* American Society for Microbiology, Washington, D.C. [1994], pages 157–162). *M. africanum* has been reported from cases of tuberculosis in tropical Africa. *M. microti* causes generalized tuberculosis in voles, and produces local lesions in such animals as guinea pigs, rabbits, and calves (Nolte and Metchock, supra, at 402).

Thus, *M. tuberculosis* is not the only respiratory pathogen of great public health concern, and neither is the *M. tuber-*

*culosis* complex. Recent developments in the taxonomy and study of the mycobacteria have resulted in recognition of *M. avium* complex (MAC) organisms as the cause of disseminated disease in immunocompromised patients, in particular AIDS patients. The two major species associated with MAC are *M. avium* and *M. intracellulare*. However, the MAC includes 28 serovars of these two distinct species, although three additional serovars of *M. scrofulaceum* (i.e., *M. avium—M. intracellulare—M. scrofulaceum* complex) were previously included. Within the *M. avium* species, three subspecies have been proposed, based on phenotypic and genotypic characteristics (*M. avium* subspecies *avium, M. avium* subspecies *paratuberculosis,* and *M. avium* subspecies *silvaticum*) (M.-F. Thorel et al., Numerical taxonomy of mycobactin-dependent mycobacteria, emended description of *Mycobacterium avium,* and description of *Mycobacterium avium* subsp. *avium,* subsp. nov. *M. avium* subsp. *paratuberculosis,* subsp. nov., and *Mycobacterium avium* subsp. *silvaticum* subsp. nov., Int. J. Syst. Bacteriol., 40:254–260 [1990]). As additional information is gathered on the genetic relationships among the mycobacteria, it is likely that changes will occur in the taxonomy of these organisms.

*M. avium,* an important pathogen of poultry and swine was recognized as a cause of disease in chickens in the late 1800s, but was not recognized as a cause of human disease until 1943 (See, Nolte and Metchock, supra, at 402). *M. intracellulare* is usually associated with disease in swine and cattle. In addition to its veterinary significance, MAC is an important pathogen of immunocompromised patients, especially those with AIDS. Indeed, disseminated MAC infection is the most common opportunistic infection observed late in the course of HIV disease. It has been reported that the frequency of disease due to MAC rises from 3% per year for individuals with CD4 counts of 100–200/$\mu$l to 39% at CD4 counts of <10/$\mu$l (S. D. Nightingale et al., "Incidence of *M. avium* intracellulare complex bacteraemia in HIV-positive patients," J. Infect. Dis., 165:108–25 [1992]). Disease with MAC is characterized by fever, cachexia, hepatic dysfunction, and anemia. As with infection with *M. tuberculosis,* infection with MAC may promote HIV expression, leading to accelerated HIV disease progression.

Human acquisition of *M. avium* appears to occur via inhalation or ingestion of fresh water in which bacilli are concentrated (K. L. Fry et al., "Epidemiology of infection by nontuberculous mycobacteria. VI. Identification and use of epidemiologic markers for studies of *Mycobacterium avium, M. intracellulare,* and *M. scrofulaceum,*" Am. Rev. Respir. Dis., 134:39–43[1986]). It is hypothesized that local infection is followed by hematogenous spread to organs of the reticuloendothelial system. It is here, in bone marrow and lymph nodes, that the number of MAC colony forming units (CFU) ultimately rise to levels several logs higher than are present in blood (D. Peterson et al., "*M. avium* complex (MAC) disease in HIV-infected patients is a uniform infection of bone marrow that does not correlate with the level of infection in blood," Natl. Conf. Hum. Retrovir. Rel. Pathogens 2:56 [1995]). The observed mycobacteremia apparently represents "spillover" of bacilli from these heavily infected organs. Alternatively, MAC mycobacteremia may occur intermittently, arising from the gastrointestinal tract, without inevitably causing tissue infection.

Recently, our understanding of the mycobacteria, including the recently described species (e.g., *M. genavense*) associated with disseminated disease in HIV-infected individuals, as well as the potential pathogens *M. asiaticum, M. haemophilum, M. malmoense, M. shimoidei,* and *M. celatum,* has greatly increased, largely due to an increased interest in opportunistic pathogens, especially those associated with disease in AIDS patients. Nonetheless, many problems remain unresolved, and reliable, rapid methods are needed for the detection of latent and active mycobacterial infections, especially in the case of AIDS patients.

Treatment of Mycobacterial Disease and Infection

The unique properties of the mycobacterial cell wall, growth rates, and other factors have provided avenues as well as detours in our development of methods for detection and treatment of mycobacterial disease. The mycobacteria characteristically have cell walls with a high lipid content, including waxes such as mycolic acid. The properties of this waxy cell wall provide the "acid-fast" nature of the organisms, as once dye is taken into the cells, they are not easily decolorized, even with acid-alcohol. Thus, unlike most organisms, the mycobacteria are said to be "acid fast" and are often referred to as "acid-fast bacilli" or "AFB."

The growth rate of the mycobacteria ranges from slow to very slow, with generation times ranging from two to 24 hours. Most isolates, including *M. tuberculosis* require long incubation periods (i.e., 4–8 weeks for traditional culture methods) under optimal conditions for growth to be easily visible in vitro. Once the organisms from a primary culture have grown, biochemical and other tests must be done in order to provide an identification. This is an unacceptably long time between sampling and a definitive identification of the organism causing disease in a patient.

The slow growth rate and the pathogenic processes of *M. tuberculosis* contribute to problems encountered in treating tuberculosis patients. As most antimicrobial drugs work against actively growing cultures, the relatively metabolically inactive mycobacteria enclosed within relatively impermeable waxy cell walls are generally unaffected by most drugs commonly used to combat bacterial disease.

The first line of drugs used against *M. tuberculosis* include isoniazid (INH), rifampin, pyrazinamide, ethambutol, and streptomycin. The second line drugs include para-amino salicylic acid, ethionamide, cycloserine, capromycin, kanamycin, amikacin, ciprofloxacin, ofloxacin and rifabutin. It is recommended that patients initially be treated with INH, rifampin, ethambutol, and pyrazinamide for 2 months. Those patients with fully drug-susceptible isolates then may be treated with INH and rifampin for an additional four months (American Thoracic Society and Centers for Disease Control, "Treatment of tuberculosis and adults and children," Am. Rev. Respir. Dis., 134:355–363 [1986]). Patients with isolates resistant to either INH or rifampin must be treated with alternative regimens for longer duration. In all cases, successful treatment of patients must continue long after acid-fast bacilli are no longer detected in sputum samples.

Drug resistant *M. tuberculosis* strains of have become a serious concern worldwide. In a recent nationwide survey of drug resistance among tuberculosis cases reported during the first quarter of 1991, it was found that 14.9% had isolates that were resistant to at least one anti-tuberculosis drug, and 3.3% had isolates resistant to both INH and rifampin (Centers for Disease Control, "National MDR-TB Task Force, national action plan to combat multidrug-resistant tuberculosis," Morbid. Mortal. Wkly. Rept. 41:1–48 [1992]). This is of grave concern, as INH and rifampin are the most effective drugs in our arsenal against *M. tuberculosis.*

For MAC, the concerns are potentially even more significant. Strains of MAC have been reported to be intrinsically resistant to anti-tuberculosis drugs and many other antimicrobials due to failure of these drugs to penetrate the lipid-rich cell wall (N. Rastogi et al., "Enhancement of drug susceptibility of *Mycobacterium avium* by inhibitors of cell envelope synthesis," Antimicrob. Agents Chemother., 34:759–764 [1990]; and N. Rastogi et al., "Simplified acetylcysteine-alkali digestion-decontamination procedure for isolation of mycobacteria from clinical specimens," J. Clin. Microbiol., 25:1428–1438 [1987]). Indeed, optimal regimens for treatment of either chronic pulmonary disease or disseminated MAC infections in AIDS patients have not been defined. In addition, no therapeutic regimen has been shown to be of sustained clinical benefit for patients with disseminated MAC (Nolte and Metchock, supra, at p. 428). It is recommended that patients with HIV and <100 $CD4^+$ cells be given prophylaxis against MAC that is to be continued for the patient's life, unless multi-drug therapy becomes necessary due to disseminated disease (Centers for Disease Control, "Recommendations on prophylaxis and therapy for disseminated *Mycobacterium avium* complex for adults and adolescents infected with human immunodeficiency virus," Morbid. Mortal. Wkly Rept., 42(RR):14–20 [1993]). Preventive therapy for MAC can be problematic because of interactions with other drugs commonly used in HIV infection, particularly the new protease inhibitors. Although no optimal treatment regimen has been defined for disseminated MAC, the U.S. Public Health Service Task Force on Prophylaxis and Therapy for MAC recommends that treatment continued for the lifetime of the patient, even if improvement is noted; this treatment should include at least two chemotherapeutic agents, one of which should be azithromycin or clarithromycin.

The situation is even potentially more grim if other Mycobacterium species are associated with disease in a patient, as almost all of the strains of the "rapid grower" (ie., in vitro growth may be observed in as few a two days) Mycobacterium species (i.e., *M. chelonae, M. fortuitum, M. abscessus,* etc.) are resistant to the anti-tuberculosis drugs. Thus, prophylactic treatment of immunocompromised patients is problematic and treatment is dependent upon the results of antimicrobial susceptibility testing of patient isolates.

Detection of Mycobacterial Disease and Infection

The field of diagnostic and clinical microbiology has continued to evolve, and yet, there remains a general need for systems that provide rapid and reliable detection of disease and infection due to microorganisms such as *M. tuberculosis.* Nontheless, the role of the clinical mycobacteriology laboratories cannot be underestimated in view of their potential contributions in controlling the spread of tuberculosis and non-tuberculosis disease through the timely detection, isolation, identification, and determination of drug susceptibility of these organisms. There is a "new sense of urgency" regarding the reporting of acid-fast smear, cultures, and drug susceptibility results to physicians, prompted in large part to the emergence of multi-drug resistant strains of *M. tuberculosis* (Nolte and Metchock, supra, at p. 400). Traditionally, tuberculosis surveillance has involved the use of preliminary skin tests (e.g., tuberculin tests), with positives being further evaluated for active disease by radiographic analysis (i.e., chest X-rays), and sputum cultures. Other samples are sometimes submitted to the laboratory for culture, including blood, bronchoalveolar lavage fluid, bronchial washings, gastric lavage fluids, urine, body fluids (e.g., cerebrospinal [CSF], pleural, peritoneal, pericardial, etc.), tissues (e.g., lymph nodes, skin, or other biopsy materials), abscess contents, aspirated fluids, skin lesions, and wounds.

In contrast to the situation with tuberculosis, blood cultures are often used for the isolation of MAC from immunocompromised patients, especially those with AIDS. Positive MAC blood cultures are generally, but not always, associated with clinical evidence of tissue infection, which typically can involve the bone marrow, liver, or lymph nodes (J. Havlik et al., "Disseminated *Mycobacterium avium* complex infection: clinical identification and epidemiologic trends," J. Infect. Dis., 165:577–580 [1992], F J. Torriani et al., "Autopsy findings in AIDS patients with *M. avium* complex bacteremia," J. Infect. Dis., 170:1601–5 [1994]). Thus, detection of MAC in tissue samples provides useful information on a patient's status. However, culturing of blood remains the most commonly used method for diagnosis of MAC infection, primarily because of the requirement for an invasive procedure to sample infected tissues.

Culture Methods. Once a specimen has been received in the laboratory suspected of containing mycobacteria, the specimen will generally be stained and examined for the presence of AFB. Sputum and other "dirty" specimens are decontaminated and concentrated prior to staining and culturing. Specimens are inoculated onto either solid egg-based media (i.e., Lowenstein-Jensen agar), or liquid medium, in which growth is more rapid. Various commercial growth media systems and methods are available for detection of mycobacteria, including BACTEC (Becton-Dickinson Diagnostic Instrument Systems), Septi-Chek (Becton-Dickinson Microbiology Systems), and the Isolator system (Wampole). Automated detection methods (e.g., those based on production of radiolabelled $CO_2$, turbidity or light) have been developed to identify cultures with microbial growth. However, growth of *M. tuberculosis* and other mycobacterial species must be confirmed by other methods. Methods presently accepted for detection and identification of are described in great detail in various publications (see e.g., N. Master (section editor) Section 3. "Mycobacteriology," in H. E. Isenberg (editor in chief), *Clinical Microbiology Procedures Handbook,* volume 1, 3.0.1–3.16.4 [1994]).

Immunological Methods. Methods for diagnosis of tuberculosis based on immunologic methods such as detection of delayed type hypersensitivity (DTH) skin responses, as well as the detection of anti-mycobacteria antibodies, or mycobacterial antigens have been studied. Historically, skin tests have been commonly used as indicators of infection with *M. tuberculosis.* The tuberculin skin test, still commonly in use, was the first immunodiagnostic test developed for detection of tuberculosis. Problems with this test include its inability to distinguish active disease from past sensitization, as well as its unknown predictive accuracy (D. Snider, "The tuberculin skin test," Am. Rev. Resp. Dis., 125(Suppl.):108–118 [1982]). Even among healthy skin test reactors, the test cannot distinguish those individuals with continued latent infection (in whom there is a continued risk of developing active disease) from those in whom a protective immune response has eradicated that infection. In vitro tests to determine the cell-mediated responses to mycobacterial antigens have also been described. However, they are expensive, technically demanding to perform and interpret, and provide no additional data than are available from skin testing (See e.g., Nolte and Metchock, supra, at p. 426).

Despite the fact that much effort has been devoted to development of serological tests for tuberculosis, these methods have not found widespread clinical use (E. Bardana, "Universal occurrence of antibodies to tubercle bacilli in sera from non-tuberculous and tuberculous individuals," Clin. Exp. Immunol., 13:65–77 [1973]; and T. M. Daniel and S. M. Debanne, "The serodiagnosis of tuberculosis and other mycobacterial disease by enzyme-linked immunosorbent assay," Am. Rev. Resp. Dis., 158:678–680 [1987]). Nonetheless, perhaps because antibody detection methods are commonly used in the diagnosis of infectious disease, assay methods based on anti-mycobacterial antibody detection have been investigated.

Antibody Detection. Several studies have focused on methods to determine the anti-mycobacterial antibody level in patients' sera. These studies have used a variety of antigen preparations, including crude extracts, purified native antigens, and recombinant proteins. Immunoassays, including ELISAs and radioimmunoassays (RIA) have been used in many of these studies (See e.g., E. G. Wilkins et al., "A Rapid, Simple Enzyme Immunoassay for Detection of Antibody to Individual Epitopes in the Serodiagnosis of Tuberculosis," Eur. J. Clin. Microbiol. Infect. Dis., 10: 559–563 [1991]; R. G. Benjamin et aL, "Serodiagnosis of Tuberculosis Using the Enzyme-Linked Immunoabsorbent Assay (ELISA) of Antibody to *Mycobacterium tuberculosis* Antigen $5^{1-3}$," Amer. Rev. Respir. Dis., 126:1013–1016 [1982]); R. Maes et al., "Development of an Enzyme Immunoassay for the Serodiagnostic of Tuberculosis and Mycobacterioses," Med. Microbiol. Immunol., 178: 323–335 [1989]); S. B. Kalish et al., "Use of an Enzyme-Linked Immunosorbent Assay Technique in the Differential Diagnosis of Active Pulmonary Tuberculosis in Humans," J. Infect. Dis., 147: 523–530 [1983]); E. Nassau et al., "The Detection of Antibodies to *Mycobacterium tuberculosis* by Microplate Enzyme-Linked Immunosorbent Assay (ELISA)," Tubercle, 57: 67–70 [1976]; F. L. Garcia-Carreno, "Enzyme Immunoassay Using BCG in Serodiagnosis of Pulmonary Tuberculosis," J. Hyg., 97: 483–487 [1986]; R. Hernandez et al., "Sensitive Enzyme Immunoassay for Early Diagnosis of Tuberculous Meningitis," J. Clin. Microbiol., 20:533–535 [1984]; J. A. McDonough et al., "Microplate and Dot Immunoassays for the Serodiagnosis of Tuberculosis," J. Lab Clin. Med., 120:318–322 [1992]; E. Sada et al., "An ELISA for the Serodiagnosis of Tuberculosis Using a 30,00-Da Native Antigen of *Mycobacterium tuberculosis*," J. Infect. Dis., 162:928–931 [1990]; A. Mathai et al., "Rapid Diagnosis of Tuberculous Meningitis with a Dot Enzyme Immunoassay to Detect Antibody in Cerebrospinal Fluid," Eur. J. Clin. Microbiol. Infect. Dis., 10:440–443 [1991]; M. Turneer et al., "Humoral Immune Response in Human Tuberculosis: Immunoglobulins G, A, and M Directed against the Purified P32 Protein Antigen of *Mycobacterium bovis* Bacillus Calmette-Guerin," J. Clin. Microbiol., 26: 1714–1719 [1988]; N. K. Kaushik et al., "Serodiagnostic Efficiency of Phospholipid Associated Protein of *Mycobacterium tuberculosis* $H_{37}Rv$," Med. Microbiol. Immunol., 182:317–327 [1993]; D. Kumar et al., "Identification of a 25-Kilodalton Protein of *Mycobacterium bovis* BCG to Distinguish BCG Strains from *Mycobacterium tuberculosis*," J. Clin. Microbiol., 34: 224–226 [1996]; Chandramuki et al. "Levels of Antibody to Defined Antigens of *Mycobacterium tuberculosis* in Tuberculous Meningitis," J. Clin. Microbiol., 27: 821–825 [1989]; K. A. Near et al., "Use of Serum Antibody and Lysozyme Levels for Diagnosis of Leprosy and Tuberculosis," J. Clin. Microbiol., 30: 1105–1110 [1992]; and H. Miöner et al., "Diagnosis of Tuberculous Meningitis: A Comparative Analysis of 3 Immunoassays, An Immune Complex Assay and the Polymerase Chain Reaction," Tubercle Lung Dis., 76: 381–386 [1995].

Although as listed above, numerous researchers have attempted to develop immunodiagnostic systems based on detection of antibody directed against mycobacterial antigens, no antibody tests have been accepted or sufficiently developed for routine diagnosis of tuberculosis. This is in large part due to the fact that the specificities of tests that use crude antigens are too low to be useful clinically. In addition, not all patients respond to the same mycobacterial antigens; any increased specificity achieved by using purified antigens is compromised by a concomitant decrease in sensitivity (See e.g., P. S. Jackett et al., "Specificity of Antibodies to Immunodominant Mycobacterial Antigens in Pulmonary Tuberculosis," J. Clin.Microbiol., 26: 2313–2318 [1988]). Lastly, immune responses are inadequate in immunocompromised hosts who are at greatest risk of developing tuberculosis. In order to avoid the problems associated with detecting host immune response, detection methods for mycobacterial antigens themselves have been investigated.

Antigen Detection. Detection of microbial antigens in fluids remote from the site of infection has been applied to diagnosis and monitoring of therapy for several infectious diseases other than tuberculosis, including cryptococcosis, histoplasmosis, and, on an experimental basis, leprosy. The type of antigen and the optimal strategy for testing varies according to the illness. In the case of cryptocococcis, a polysaccharide capsular antigen can be detected in cerebrospinal fluid and blood using a simple latex agglutination test (A. A. Gal et al., "The clinical laboratory evaluation of cryptococcal infections in the acquired immunodeficiency syndrome," Diagn. Microbiol. Infect. Dis., 7:249–54 [1987]). In disseminated histoplasmosis, a heat stable polysaccharide antigen may be detected in blood, CSF, and urine by radioimmunoassay (L. J. Wheat et al., "Diagnosis of disseminated histoplasmosis by detection of *Histoplasma capsulatum* antigen in serum and urine specimens," N. Engl. J. Med., 314:83–8 [1986]). In leprosy, serum levels of *M. leprae* phenolic glycolipid I correlate with bacillary load at diagnosis and during therapy, ranging from 12 ng/ml in paucibacillary patients to as high as 8000 ng/ml in multibacillary patients (D. B. Young et al., "Detection of phenolic glycolipid I in sera from patients with lepromatous leprosy," J. Infect. Dis., 152:1078–81 [1985]). However, the successes with these organisms have not been mirrored in diagnosis of tuberculosis and MAC disease, with the exception of one report for MAC, described below.

Detection of Mycobacterial Antigens. Previous reports of antigen detection assays for rapid diagnosis of tuberculosis have been limited to examination of fluids obtained from the site of clinical disease, such as cerebrospinal fluid, sputum, or bronchoalveolar lavage fluid (E. Sada et al., "Detection of mycobacterial antigens in cerebrospinal fluid of patients with tuberculous meningitis by enzyme-linked immunosorbent assay," Lancet 2:651–2 [1983]; I. O. al Orainey et al., "Detection of mycobacterial antigens in sputum by an enzyme immunoassay," Eur. J. Clin. Microbiol. Infect. Dis., 11:58–61 [1992]; R. Kansal et al., "Detection of mannophosphoinositide antigens in sputum of tuberculosis patients by dot enzyme immunoassay," Med. Microbiol. Immunol. Berl., 180:73–8 [1991]; M. A. Yanez et al., "Determination of mycobacterial antigens in sputum by enzyme immunoassay," J. Clin. Microbiol., 23:822–5 [1986]; G. V. Kadival et al., "Radioimmunoassay of tuberculous antigen," Indian J. Med. Res., 75:765–70 [1982], A. Chandramuki et al., "Detection of mycobacterial antigen and antibodies in the cerebrospinal fluid of patients with tuberculous meningitis," J. Med. Microbiol., 20: 239–247 [1985]; C. L. Cambiaso et al., "Immunological detection of mycobacterial antigens in infected fluids, cells and tissues by latex agglutination—Animal model and clinical application," J. Immunol. Meth., 129: 9–14 [1990]). A number of other antigen assays have also been described (See e.g., T. M. Daniel, "Rapid diagnosis of tuberculosis: Laboratory techniques applicable in developing countries," Rev. Infect. Dis., 2(Supplement 2): S471–S478 ([1989]).

In other studies, the infected fluids were placed in liquid culture for a short period, and mycobacterial products were detected in the culture medium (A. Raja et al., "Specific detection of Mycobacterium tuberculosis in radiometric cultures by using an immunoassay for antigen 5," J. Infect. Dis., 158:468–70 [1988]; A. Raja et al., "The detection by immunoassay of antibody to mycobacterial antigens and mycobacterial antigens in bronchoalveolar lavage fluid from patients with tuberculosis and control subjects," Chest 94: 133–137 [1988]; R. Schoningh R et al., "Enzyme immunoassay for identification of heat-killed mycobacteria belonging to the *Mycobacterium tuberculosis* and *Mycobacterium avium* complexes and derived from early cultures," J. Clin. Microbiol., 28:708–13 [1990]; A. Drowart et al., "Detection of mycobacterial antigens present in short-term culture media using particle counting immunoassay," Am. Rev. Respir. Dis., 147:1401–6 [1993]). The detection threshold of these assays ranged from 1 ng to 1 μg/ml. All used a polyclonal antiserum rather than monoclonal antibody for capture; several used the same serum for both capture and detection. In none of these reports were fluids remote from the site of infection studied, and in none could the assay identify subjects with latent infection.

*M. tuberculosis* Antigens. In contrast to the situation with many bacteria, the antigens of *M. tuberculosis* are a remarkably complex mixture of proteins, polysaccharides, and lipids. The polysaccharide antigens share antigenic cross-reactivity with Nocardia, the corynebacteria, and staphylococci, and generally do not elicit delayed type hypersensitivity (DTH) (Y. Yamamura et al., "Biology of the mycobacterioses. Chemical and immunological studies on peptides and polysaccharides from tubercle bacilli," Ann. NY Acad. Sci., 154:88–97 [1968]; and S. D. Chaparas et al., "Comparison of lymphocyte transformation, inhibition of macrophage migration and skin tests using dialyzable and nondialyzable tuberculin fractions from *Mycobacterium bovis* (BCG)," J. Immunol., 107:149–53 [1971]). However, the protein antigens of the Mycobacterium elicit a DTH response, and stimulate lymphocyte blastogenic responses in both sensitized humans and guinea pigs (L. F. Affronti et al., "Some early investigations of *Mycobacterium tuberculosis*," Am. Rev. Respir. Dis., 92:1–8 [1995]); T. M. Daniel et al., "Reactivity of purified proteins and polysaccharides from *Mycobacterium tuberculosis* in delayed skin test and cultured lymphocyte mitogenesis assays," Infect. Immun., 9:44–7 [1974]; and S. D. Chaparas et al., "Tuberculin-active carbohydrate that induces inhibition of macrophage migration but not lymphocyte transformation," Science 170:637–9 [1970]).

The antigenic repertoire of *M. tuberculosis* includes some proteins which are also found intracellularly, and some which appear uniquely as secreted proteins. As the technology to define these antigens has improved, their number has grown. In 1971, 11 antigens could be identified by immunoprecipitation in culture filtrate (the spent medium of cultures of *M. tuberculosis* after the bacilli have been removed by filtration (B. W. Janicki et al., "A reference system for antigens of *Mycobacterium tuberculosis*," Am. Rev. Respir. Dis., 104:602–4 [1971]). Antigen 5 (a 38 kD protein), and antigen 6 (a 30–32 kD protein later termied alpha antigen, BCG 85B, and MPT59), were prominent, and appeared to have some antigenic determinants which were restricted to *M. tuberculosis* (T. M. Daniel et al., "Immunobiology and species distribution of *Mycobacterium tuberculosis* antigen 5," Infect. Immun., 24:77–82 [1979]; T. M. Daniel et al., "Demonstration of a shared epitope among mycobacterial antigens using a monoclonal antibody," Clin. Exp. Immunol., 60:249–58 [1985]; and T. M. Daniel et al., "Specificity of *Mycobacterium tuberculosis* antigen 5 determined with mouse monoclonal antibodies," Infect. Immun., 45:52–5 [1984]). A decade later, Closs and colleagues identified as many as 50 distinct antigens using a system of crossed immunoelectrophoresis (O. Closs et al., "The antigens of *Mycobacterium bovis*, strain BCG, studied by crossed immunoelectrophoresis: a reference system," Scand. J. Immunol., 12:249–63 [1980]). The use of 2-D gel electrophoresis has increased this number to greater than 100. This growing number of potential antigens has presented a challenge in the development of diagnostic and treatment systems.

MAC Antigens. In contrast to these reports in which only infected fluids were studied, a method was reported for detection of a MAC protein antigen in urine of AIDS patients with disseminated MAC infection (A. A. Sippola et al., "*Mycobacterium avium* antigenuria in patients with AIDS and disseminated *M. avium* disease," J. Infect. Dis., 168:466–8 [1993]). This assay utilized a goat antiserum ("K-II") which had been developed by immunization with *M. intracellulare*, and which primarily recognized a 22.5 kD antigen of *M. intracellulare*, *M. avium* and *M. scrofulaceum*, but not *M. tuberculosis*. Antigenuria was detected in clinical specimens using an assay in which supported nitrocellulose strips were dipped into voided urine samples, which were then probed with the antiserum. Antigenuria was detected in 7/11 patients with *M. avium*-complex disease, and in 16/100 HIV+ controls. Two of the apparent false positive controls were subsequently found to have disseminated *M. avium* infection.

Although this assay format was initially appealing in terms of its simplicity, it has several major shortcomings, including: the use of supported nitrocellulose strips hinders uniform washing of multiple samples; the binding of the target antigen to the paper is non-specific; the assay cannot be used to detect non-protein antigens, as their binding to the paper may not be adequate. Also, the specificity of the assay is entirely determined by that of the antiserum. It is therefore critical that the serum not cross-react with human proteins or antigens of other pathogens, an unrealistic expectation for this assay. Therefore, the advantages of these researchers' assay may be outweighed by its disadvantages and/or be inadequate to offer clinicians a substantial advantage when compared to the use of blood cultures for detection of mycobacteria.

Effect of HIV Infection on Diagnosis of Mycobacterial Disease

HIV infection alters the manifestations of tuberculosis, particularly in those patients with advanced HIV disease, in whom half have mycobacteremia and more than 75% have lymph node, hepatic, or bone marrow involvement, particularly those with low CD4 counts (B. E. Jones et al., "Relationship of the manifestations of tuberculosis to CD4 cell counts in patients with human immunodeficiency virus infection," Am. Rev. Respir. Dis., 148:1292–1297 [1993]; G. I. Santos et al., "Liver disease in patients with human immunodeficiency virus infection. Study of 100 biopsies," Rev. Clin. Esp., 193:115–8 [1993]; A. D. Pithie et al., "Fine-needle extrathoracic lymph-node aspiration in HIV-associated sputum-negative tuberculosis," Lancet 340:1504–5 [1992]; and P. F. Barnes et al., "Tuberculosis in the 1990s," Ann. Intern. Med., 119:400–10 [1993].

However, HIV infection is accompanied by less radiographic evidence of pulmonary disease, fewer lung zones with cavitation, and reduced numbers of mycobacterial colony-forming units in sputum (R. J. Brindle et a., "Quantitative bacillary response to treatment in HIV-associated pulmonary tuberculosis," Am. Rev. Respir. Dis., 147:958–61 [1993]). Thus, the likelihood of diagnosis based on expectorated sputum is reduced in HIV-associated tuberculosis, even though the total mycobacterial burden may be greater. This has led to the necessity of increased evaluation of specimens other than sputum, particularly tissues such as pleura, liver, and bone marrow. Patients with miliary or disseminated tuberculosis, particularly those with HIV infection, often require multiple biopsies prior to initiation of therapy.

Again, despite the large number of studies, no antigen detection method has been developed to date which provides reliable, highly specific, and highly sensitive results, especially for "dirty" samples such as sputum (See e.g., J. M. Grange, "The rapid diagnosis of paucibacillary tuberculosis," Tubercle, 70:1–4 [1989]; and Nolte and Metchock, supra, at p. 426).

Importantly, serodiagnostic tests for tuberculosis, although potentially simple and inexpensive, have been especially hampered by poor sensitivity in HIV-infected persons in whom antibody responses are diminished (T. M. Daniel et al., "Reduced sensitivity of tuberculosis serodiagnosis in patients with AIDS in Uganda," Tuber. Lung Dis., 75:33–7 [1994]). This is important because the patient populations that are dually infected with HIV and *M. tuberculosis* is at greatest risk for developing active tuberculosis (M. E. Villarino et al., "Management of persons exposed to multidrug-resistant tuberculosis," Morb. Mort. Wkly. Rep., 41(RR-11):61–71 [1992]).

Diagnosis of Latent Infection with *M. tuberculosis*

Identification of individuals with latent *M. tuberculosis* infection is a problem which cannot be addressed by current methods. The natural history of *M. tuberculosis* infection is such that only 5–10% of individuals who are otherwise healthy will ever develop tuberculosis. As mentioned above, the risk of tuberculosis is highest in the first year following infection, but tuberculosis can occur as long as 50 years later. Thus, the infection clearly is contained but not eradicated in many infected but healthy individuals. Presently, there is no reliable method to distinguish between individuals who are latently infected and those whose infections have been eradicated by a protective immune response. Both groups have positive skin tests with purified protein derivative (PPD), as the longevity of a positive skin test can reflect immunologic memory as well as persistent latent infection.

The presence of immunosuppressive concurrent illnesses increases the likelihood of recrudescent disease in tuberculosis-infected persons. This is most strongly expressed in HIV-co-infected persons, in whom the risk of re-activation of tuberculosis may be increased from 10 to 100 fold. Indeed, HIV has emerged as the most significant risk factor for the progression of latent tuberculosis to active disease (Snider et al., at p. 5; Selwyn et al., "A prospective study of the risk of tuberculosis among intravenous drug abusers with human immunodeficiency virus infection," N. Eng. J. Med., 320:545–550 [1989]). However, skin testing becomes increasingly unreliable as an indicator of *M. tuberculosis* infection as the CD4 count declines. It thus remains difficult to efficiently target those individuals who would benefit most from preventive therapy.

Yet, identification of latently-infected persons is desirable for initiation of tuberculosis preventive therapy. Although such therapy (daily doses of INH for nine months) can be administered to all skin test positive individuals, such therapy obviously would only benefit those subjects who ultimately would have developed tuberculosis. Thus at least 10–20 subjects must be treated to prevent one case of tuberculosis. The other 9–19 treated subjects are subjected to risks associated with INH (e.g., hepatitis, neuropathy) without any potential benefit. This problem is compounded by the present inability to monitor the effectiveness of preventive therapy. Some individuals will fail preventive therapy because of poor compliance with longterm administration of INH. Others will fail because they were infected with an INH-resistant isolate. At present, there is no method to determine whether preventive therapy has been successful in completely eradicating latent infection with *M. tuberculosis*.

In sum, there is no entirely satisfactory method for diagnosis either active tuberculosis or latent mycobacterial infection. Direct examination of sputum or infected tissues is insufficiently sensitive (See e.g., L. B. Heifets and R. C. Good, "Current laboratory methods for the diagnosis of tuberculosis," in B. R. Bloom (ed.) *Tuberculosis: Pathogenesis, Protection and Control*, American Society for Microbiology, Washington, D.C. [1994], pages 85–110). Traditional methods, including cultivation of the organism require the time and facilities for prolonged incubation. Assays based on DNA amplification are expensive and technically demanding, and may not be applicable for routine use in clinical laboratories outside of major medical centers in industrialized countries. The development of a simple, rapid, diagnostic test which does not rely on the growth of organisms in vitro, but that is capable of identifying individuals with latent, subclinical *M. tuberculosis* infection, and which might predict the likelihood of subsequent relapse, would be of tremendous value for tuberculosis control programs worldwide.

Monitoring of Therapy

Many factors can adversely affect the response to anti-tuberculous therapy. These include primary drug resistance, patient non-compliance, malabsorption, adverse interactions with other medications, and other host factors. Inadequate treatment can lead to emergence of secondary drug resistance due to selective pressures on mycobacterial growth. In order to assess a patient's response to anti-tuberculosis therapy, patients must be monitored throughout their treatment regimen.

However, sputum cultures and AFB smears return to negative slowly during therapy, such that the proportion of samples which become negative are typically only 40% at 1 month, 80% at 2 months, and 90–95% at 3 months. Chest radiographs also improve slowly, and may not significantly improve until 3 months of treatment. It thus is difficult to identify promptly those patients who ultimately will fail any given tuberculosis treatment regimen. Better early indicators of success or failure clearly are needed.

Mitchison has suggested that the early bactericidal activity of anti-tuberculosis regimens, as determined by quantitative sputum cultures, might predict the overall effectiveness of a treatment regimen (S. L. Chan et al., "The early bactericidal activity of rifabutin measured by sputum viable counts in Hong Kong patients with pulmonary tuberculosis," Tubercle 1992;33–8 [1992]; and A. J. Jindani et al., "The Early Bactericidal Activity of Drugs in Patients with Pulmonary Tuberculosis," Am. Rev. Respir. Dis., 121:939–49 [1980]). He observed approximately a $10^{-3}$ drop in the number of viable *M. tuberculosis* bacilli during the first 2 weeks of effective multi-drug therapy, and noted lesser reductions with less effective regimens. He suggested that new drugs for tuberculosis might be evaluated in short term studies (1–2 weeks) using quantitative culture as an endpoint. However, this approach has not been widely accepted, largely because of difficulties of performing the assay in a standardized fashion, particularly with regard to homogenization of non-uniform sputum specimens. This lack of standardization precludes the use of this method in the clinical setting.

Problems also exist in monitoring therapy for MAC infection in AIDS patients through serial blood cultures. An autopsy series of 44 patients with MAC bacteremia found that 13 (30%) had no histologic evidence of MAC disease (F. J. Torriani et al., "Autopsy findings in AIDS patients with *M. avium* complex bacteremia," J. Infect. Dis., 170:1601–5 [1994]), suggesting that transient bloodstream infection may occur and may be self-limited. Conversely, other patients have only transiently or intermittently positive blood cultures in the face of high tissue burdens of mycobacteria (C. A. Kemper et al., "Transient bacteremia due to *M. avium* complex in patients with AIDS," J. Infect. Dis., 170:488–93 [1994]). These observations suggest that sustained mycobacteremia may be a late event in the natural history of MAC infection, and that blood culture is not an adequate diagnostic or monitoring tool when used alone. However, access to the main site of infection (bone marrow, lymph node, or liver) requires an invasive diagnostic procedure which is not usually undertaken without prior attempts at diagnosis by non-invasive measures. These combined factors often lead to a delay in diagnosis and initiation of therapy, and make it difficult to evaluate the response to therapy.

In sum, despite advances in the detection of *M. tuberculosis* and other mycobacteria, the need remains for a safe, reliable, easy-to-use system for the detection of infection with these organisms, as well as means for monitoring patients with disease or infection. In particular, there is an urgent need for useful methods to use samples such as urine and other fluids for the detection of infection and disease with Mycobacterium species.

SUMMARY OF THE INVENTION

The present invention provides a rapid method for the detection of disease and infection due to the mycobacteria, in particular *M. tuberculosis*, as well as MAC. The present invention is intended for detection of pulmonary mycobacterial disease or infection, and disseminated mycobacterial disease, as well as localized infection with mycobacteria at sites other than the pulmonary area.

The present invention provides kits for the detection of Mycobacterium in a test sample, comprising: a) a solid support; and b) a monoclonal antibody directed against a portion of alpha antigen immobilized on the solid support. In one embodiment, the kit further comprises a primary antibody, while in another embodiment the kit comprises a reporter antibody, in yet another embodiment the kit further comprises an amplifier system. It is also contemplated that the kit of the present invention comprise a primary antibody and reporter antibody, as well as an amplifier system. In a particularly preferred embodiment, the Mycobacterium species detected is *Mycobacterium tuberculosis*. In an alternative embodiment the Mycobacterium species detected is *Mycobacterium avium*.

It is also contemplated that the kit of the present invention will include additional components, including, but not limited to, such items as an alpha antigen control, a diluent such as saline or water, as well as a plurality of alpha antigen samples with known concentrations of alpha antigen suitable for use in preparing a standard curve(s) for the determination of antigen concentration in the test (i.e., patient) samples. Furthermore, in kits in which biotinylated antibodies are used, in one preferred embodiment, the primary antibody is preadsorbed with an avidin compound (i.e., strepavidin) coupled to biotinylated capture antibody, prior to use in the kit. It is further contemplated that the kit of the present invention comprise methods for analyzing samples using blots, including but not limited to Western blots. These blotting kits may include additional reagents such as those listed above, as well as reagents, including but not limited to, such as paper suitable for the blotting system used, and blocking solution.

It is also contemplated that the antibodies of the kit of the present invention be prepared through the use of synthetic peptides as immunogens. In this embodiment, synthetic peptides of known sequence are used to induce the production of at least one of the antibodies used in the kit. It is also contemplated that the synthetic peptides be used as an immunogen while they are still attached to the beads used to prepare them. Thus, the present invention encompasses antigens of mycobacteria that are naturally occurring and harvested from samples such as sputum, urine or blood samples, as well as mycobacterial antigens that are produced synthetically for use in the production of antibodies for use in the kit. It is also contemplated that these synthetic peptides be used as antigens in the kit. In a preferred embodiment, the synthetic peptides correspond to the alpha antigen of *M. tuberculosis* or MAC. Thus, the sequences of SEQ ID NOS:1–8 may be used in the form of synthetic peptides for use in the present invention. It is also contemplated that immune complexes will be tested using the kit of the present invention. In this embodiment, the immune complexes may be treated using methods known in the art to dissociate antibodies from antigens.

It is also contemplated that the samples tested using the kit of the present invention will be obtained from individuals infected with one or more types of the human immunodeficiency virus. It is also contemplated that the kit will be used for monitoring the progression of therapy in individuals infected with Mycobacterium, in particular *M. tuberculosis* and/or MAC. It is further contemplated that the kit will be used with samples from patients who are infected with *M. tuberculosis*, as determined by skin test positivity, chest radiograph positivity, and/or sputum cultures containing *M. tuberculosis*.

The present invention also provides methods for the detection of Mycobacterium in a sample comprising: a) providing: i) a sample suspected of containing at least a portion of the alpha antigen of Mycobacterium and ii) a monoclonal antibody directed against the portion of Mycobacterium alpha antigen; b) adding the sample to the monoclonal antibody under conditions such that the antibody binds to the Mycobacterium alpha antigen in the sample to form an antibody-antigen complex; and c) detecting the binding of said antigen and antibody.

In a preferred embodiment of the method of the present invention, the detecting comprises adding the primary antibody to the antigen-antibody complex so that the primary antibody binds to the antigen to form an antibody-antigen-antibody sandwich. In another preferred embodiment of the method, the detecting further comprises adding a reporter reagent to the antibody-antigen-antibody sandwich to form an antibody-antigen-antibody-antibody sandwich. In a particularly preferred embodiment, the detecting further comprises adding an amplifier to said antibody-antigen-antibody-antibody sandwich.

In one embodiment, the monoclonal antibody comprises a murine monoclonal antibody. In a preferred embodiment, the murine monoclonal antibody is biotinylated. In a particularly preferred embodiment, the primary antibody is preadsorbed with avidin (e.g., streptavidin) coupled to biotinylated capture antibody, prior to use in the method of the present invention for the detection of Mycobacterium species. In yet another particularly preferred embodiment, the solid support is coated with avidin.

In another embodiment, detection is achieved through use of such methods as enzyme immunoassay, radioimmunoassay, fluorescence immunoassay, flocculation, particle agglutination, and in situ chromogenic assay. It is not intended that the present invention be limited to any particular assay format.

It is also contemplated that the method of the present invention will include additional components, including, but not limited to, such items as an alpha antigen control, a diluent such as saline or water, as well as a plurality of alpha antigen samples with known concentrations of alpha antigen suitable for use in preparing standard curve(s) for the determination of antigen concentration in the test (i.e., patient) samples. Furthermore, in methods in which biotinylated antibodies are used, in a preferred embodiment, the primary antibody is preadsorbed with an avidin compound (i.e., strepavidin) coupled to biotinylated capture antibody prior to use in the method. It is further contemplated that the method of the present invention comprise methods for analyzing samples using blots, including but not limited to Western blots. These blotting methods may include additional reagents such as those listed above, as well as reagents, including but not limited to, such as paper suitable for the blotting system used, and blocking solution.

It is also contemplated that the antibodies of the method of the present invention be prepared through the use of synthetic peptides as immunogens. In this embodiment, synthetic peptides of known sequence are used to induce the production of at least one of the antibodies used in the method. It is also contemplated that the synthetic peptides be used as an immunogen while they are still attached to the beads used to prepare them. Thus, the present invention encompasses antigens of mycobacteria that are naturally occurring and harvested from samples such as sputum, urine or blood samples, as well as mycobacterial antigens that are produced synthetically for use in the production of antibodies for use in the method. It is also contemplated that these synthetic peptides be used as antigens in the kit. In a preferred embodiment, the synthetic peptides correspond to the alpha antigen of *M. tuberculosis* or MAC. Thus, the sequences of SEQ ID NOS:1–8 may be used in the form of synthetic peptides for use in the present invention.

In one embodiment of the method, the Mycobacterium detected by the method of the present invention is selected from the group consisting of *Mycobacterium tuberculosis, Mycobacterium avium* and *Mycobacterium intracellulare.* In one embodiment of the methods of the present invention, the portion of said Mycobacterium alpha antigen is selected from the group comprising SEQ ID NOS: 1, 2, 3, 4, 5, 6, 7 and 8. Thus, it is contemplated that fragments of the alpha antigen, as well as the entire alpha antigen will be used in the methods of the present invention. It is also contemplated that immune complexes will be tested using the methods of the present invention. In this embodiment, the immune complexes may be treated using methods known in the art to dissociate antibodies from antigens.

It is contemplated that any sample will be used in the method of the present invention, including but not limited to urine samples, sputum samples, blood samples, and serum samples. In the case of sputum samples, it is contemplated that most samples will be digested and/or decontaminated using standard methods prior to their analysis in the method of the present invention. It is also contemplated that some samples tested using the method of the present invention will be obtained from individuals infected with human immunodeficiency virus, including, but not limited to, HIV-1 and HIV-2.

It is also contemplated that the methods of the present invention will be used for monitoring the progression of therapy in individuals infected with Mycobacterium, in particular *M. tuberculosis* and/or MAC. It is further contemplated that the methods will be used with samples from patients who are infected with *M. tuberculosis,* as determined by skin test positivity, chest radiograph positivity, and/or sputum cultures containing *M. tuberculosis.*

The present invention also provides methods for the detection of mycobacterial antigen in a urine sample comprising a) providing: i) a urine sample suspected of containing at least a portion of alpha antigen of Mycobacterium; and ii) a monoclonal antibody directed against the portion of Mycobacterium alpha antigen; b) adding the urine sample to the monoclonal antibody under conditions such that the antibody binds to the Mycobacterium alpha antigen in the urine sample to form an antibody-antigen complex; and c) detecting the binding.

The present invention also provides methods for the detection of Mycobacterium in a sample comprising: a) providing: i) a sample suspected of containing at least a portion of the alpha antigen of Mycobacterium and ii) a monoclonal antibody directed against the portion of Mycobacterium alpha antigen; b) adding the sample to the monoclonal antibody under conditions such that the antibody binds to the Mycobacterium alpha antigen in the sample to form an antibody-antigen complex; and c) detecting the binding of said antigen and antibody.

In a preferred embodiment of the method of the present invention, the detecting comprises adding the primary antibody to the antigen-antibody complex so that the primary antibody binds to the antigen to form an antibody-antigen-antibody sandwich. In another preferred embodiment of the method, the detecting further comprises adding a reporter reagent to the antibody-antigen-antibody sandwich to form an antibody-antigen-antibody-antibody sandwich. In a particularly preferred embodiment, the detecting further comprises adding an amplifier to said antibody-antigen-antibody-antibody sandwich.

In one embodiment, the monoclonal antibody comprises a murine monoclonal antibody. In a preferred embodiment, the murine monoclonal antibody is biotinylated. In a particularly preferred embodiment, the primary antibody is preadsorbed with avidin (e.g., streptavidin) coupled to biotinylated capture antibody prior to use in the method of the present invention for the detection of Mycobacterium species. In yet another particularly preferred embodiment, the solid support is coated with avidin.

In another embodiment, detection is achieved through use of such methods as enzyme immunoassay, radioimmunoassay, fluorescence immunoassay, flocculation, particle agglutination, and in situ chromogenic assay. It is not intended that the present invention be limited to any particular assay format.

It is also contemplated that the method of the present invention will include additional components, including, but not limited to, such items as an alpha antigen control, a diluent such as saline or water, as well as a plurality of alpha antigen samples with known concentrations of alpha antigen suitable for use in preparing standard curve(s) for the determination of antigen concentration in the test (i.e., patient) samples. Furthermore, in methods in which biotinylated antibodies are used, in a preferred embodiment, the primary antibody is preadsorbed with an avidin compound (i.e., strepavidin) coupled to biotinylated capture antibody prior to use in the method. It is further contemplated that the method of the present invention comprise methods for analyzing samples using blots, including but not limited to Western blots. These blotting methods may include additional reagents such as those listed above, as well as reagents, including but not limited to, such as paper suitable for the blotting system used, and blocking solution.

It is also contemplated that the antibodies of the method of the present invention be prepared through the use of synthetic peptides as immunogens. In this embodiment, synthetic peptides of known sequence are used to induce the production of at least one of the antibodies used in the method. It is also contemplated that the synthetic peptides be used as an immunogen while they are still attached to the beads used to prepare them. Thus, the present invention encompasses antigens of mycobacteria that are naturally occurring and harvested from samples such as sputum, urine or blood samples, as well as mycobacterial antigens that are produced synthetically for use in the production of antibodies for use in the method. It is also contemplated that these synthetic peptides be used as antigens in the kit. In a preferred embodiment, the synthetic peptides correspond to the alpha antigen of *M. tuberculosis* or MAC. Thus, the sequences of SEQ ID NOS:1–8 may be used in the form of synthetic peptides for use in the present invention.

In one embodiment of the method, the Mycobacterium detected by the method of the present invention is selected from the group consisting of *Mycobacterium tuberculosis, Mycobacterium avium* and *Mycobacterium intracellulare.* In one embodiment of the methods of the present invention, the portion of said Mycobacterium alpha antigen is selected from the group comprising SEQ ID NOS: 1, 2, 3, 4, 5, 6, 7 and 8. Thus, it is contemplated that fragments of the alpha antigen, as well as the entire alpha antigen will be used in the methods of the present invention. It is also contemplated that immune complexes present in urine samples will be tested using the methods of the present invention. In this embodiment, the immune complexes may be treated using methods known in the art to dissociate antibodies from antigens.

It is also contemplated that some samples tested using the method of the present invention will be obtained from individuals infected with human immunodeficiency virus, including, but not limited to, HIV-1 and HIV-2.

It is also contemplated that the methods of the present invention will be used for monitoring the progression of therapy in individuals infected with Mycobacterium, in particular *M. tuberculosis* and/or MAC. It is further contemplated that the methods will be used with samples from patients who are infected with *M. tuberculosis,* as determined by skin test positivity, chest radiograph positivity, and/or sputum cultures containing *M. tuberculosis.*

The present invention also provides a composition comprising purified monoclonal antibody directed against a portion of Mycobacterium alpha antigen. In one embodiment, the monoclonal antibody is a murine monoclonal antibody. In an alternative embodiment, the murine monoclonal antibody is directed against epitopes of the alpha antigen of *M. tuberculosis, M. avium* or *M. intracellulare.* In a particularly preferred embodiment, the murine monoclonal antibody is directed against *M. tuberculosis* epitopes. In yet another preferred embodiment, the alpha antigen used to produce the murine monoclonal antibody is comprised of SEQ ID NOS:1, 2, 3, 4, 5, 6, 7, or 8. It is also contemplated that the monoclonal antibody of the present invention will be produced through the use of synthetic peptides as antigens. In a preferred embodiment, the monoclonal antibody of the present invention is raised against SEQ ID NOS: 3, 4, 6 or 7. It is further contemplated that the monoclonal antibody be produced using any suitable methods for monoclonal antibody production, including intrasplenic methods, cell culture, etc. It is not intended that the monoclonal antibody of the present invention be limited to an antibody produced using a particular method or produced using a particular animal species. It is also not intended that the antibodies used in the present invention be of a particular class of immunoglobulin.

DESCRIPTION OF THE FIGURES

FIG. 1 shows Western blots for detection of alpha antigen purified from culture filtrates.

FIG. 2 is a graphical representation of the reaction used to produce a colored reaction product in the amplified ELISA test method.

FIG. 3 is a graph showing the results of an amplified ELISA test for detection of alpha antigen as described in Example 3.

FIG. 4 is a graph showing the detection of alpha antigen in spiked samples of human serum and urine.

FIG. 5 is a graph showing the results of a comparison between detection of *M. tuberculosis* by the BACTEC system and the amplified ELISA test method.

FIG. 6 is a graph showing the amplified ELISA results for urine samples from HIV-negative tuberculosis patients and controls.

FIG. 7 is a graph showing the amplified ELISA results for serum samples from HIV-negative tuberculosis patients and controls.

FIG. 8 is a graph showing the amplified ELISA results for urine samples from HIV-positive tuberculosis patients and controls.

FIG. 9 shows Western blots of filtrates of *M. tuberculosis, M. avium,* and *M. smegmatis* using monoclonal TBC27 as the capture antibody.

FIG. 10 is a graph showing the standard curves for alpha antigen amplified ELISA using culture filtrates of *M. tuberculosis* and *M. avium.*

FIG. 11 shows the urinary antigen values in HIV-negative subjects grouped according to their *M. tuberculosis* and *M. avium* status.

FIG. 12 shows the urinary antigen values in HIV-positive subjects grouped according to their *M. tuberculosis* and *M. avium* status.

FIGS. 13A–13C show the results of alpha antigen detection assays for sputum samples obtained from three patients, with one patient's results being shown in each of the three (i.e., FIGS. 13A–13C).

FIGS. 14A–14F show the results of alpha antigen detection assays for sputum samples obtained from nine patients, with one patient's results being shown in each of the nine figures (i.e., FIGS. 14A–14F).

FIG. 15 shows the results of alpha antigen detection assays for sputum samples obtained from one patient.

FIG. 16 shows Western blots for the detection of alpha antigen by three monoclonal antibodies.

FIG. 19 shows the amino acid sequences of *M. tuberculosis* and *M. avium* alpha antigen.

FIG. 20 shows Western blots of *M. avium* filtrate tested with murine antiserum directed against alpha antigen peptides.

Figure 1:
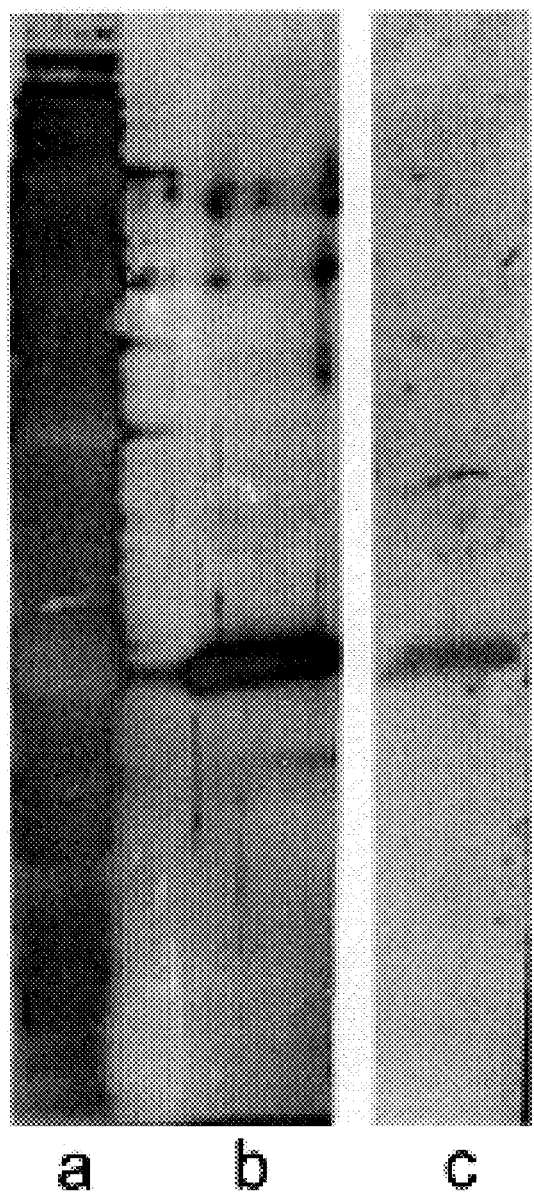
Figure 2:
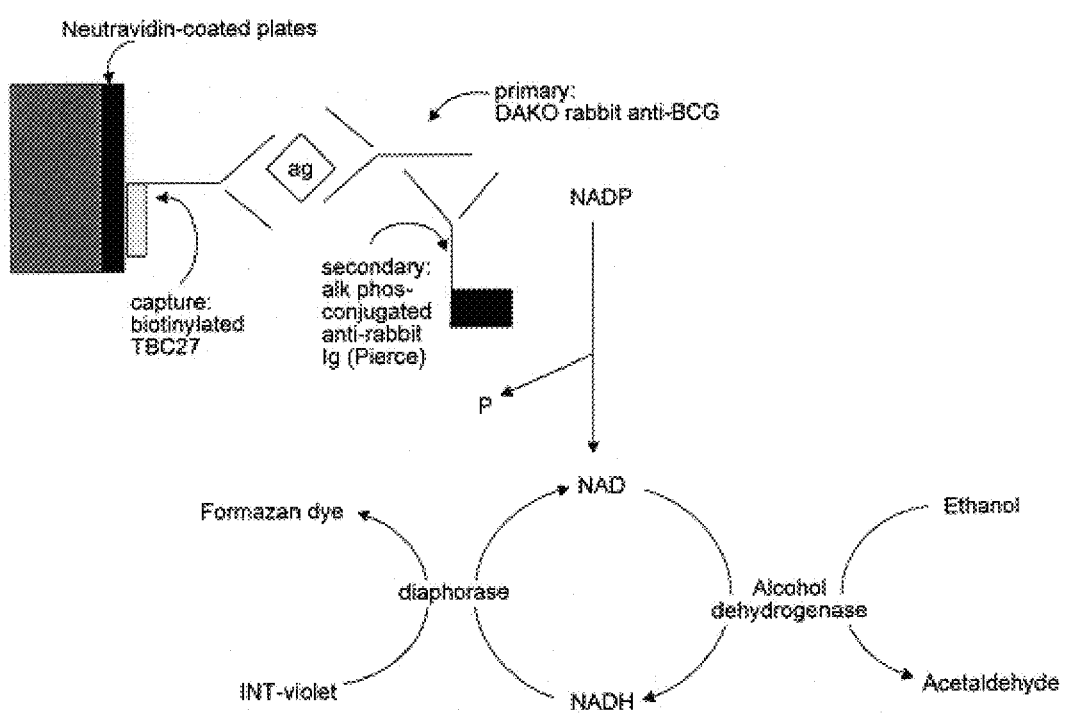

FIGS. 21A–21C show Western blots of *M. avium* and *M. tuberculosis* culture filtrates tested with goat *M. intracellulare* antisera. FIG. 21A shows the results with Kris antiserum; FIG. 21B shows the results with Kris antiserum adsorbed with *M. tuberculosis*; and FIG. 21C shows the results with Jane antiserum.

FIGS. 22A–22B show Western blots of *M. avium* and *M. tuberculosis* culture filtrates tested with Kris antiserum and Kris antiserum adsorbed with *M. tuberculosis*. FIG. 22A shows the results with the unabsorbed antiserum and FIG. 22B shows the results with adsorbed antiserum.

GENERAL DESCRIPTION OF THE INVENTION

Previous reports of antigen detection assays for direct diagnosis of tuberculosis have been limited to examination of fluids obtained from the site of clinical disease, such as cerebrospinal fluid, sputum, or bronchoalveolar lavage fluid. Furthermore, the range of the lower limit of detection of these assays was reported to be from 1 ng to 1 µg/ml. In addition, the lower detection thresholds were only achieved in those assay which used a polyclonal antiserum for capture. Moreover, several used the same serum for both capture and detection. In none of these reports were fluids remote from the site of infection studied. None of these assays were able to identify subjects with latent infection. This is in contrast with the present invention, in which identification of a mycobacterial antigen in fluids remote from the site of infection in patients infected with *M. tuberculosis* is possible.

In the method of the present invention, a sandwich ELISA (enzyme-linked immnuosorbent assay) with a monoclonal antibody for capture and a secondary antibody for detection of bound monoclonal antibody is used. In a preferred embodiment, the signal from the assay is amplified using an recycling enzymatic method, which increases the signal over 500 fold. Special measures are included in order to reduce background noise. The assay offers numerous advantages as compared to existing methods for tuberculosis diagnosis. First, body fluids remote from the site of infection can be tested using the method of the present invention. The test can be used with infected body fluids, as well as urine and blood. Although urine and blood usually do not contain *M. tuberculosis*, these sites may contain secreted products of the infection. Detection of these secreted products provides a clear advantage in attempts to diagnose a localized infection such as is usually the case in tuberculosis. It is a particularly important advantage in diagnosis of tuberculosis in children, from whom quality sputum specimens are difficult to collect and are generally not available.

Detection of Alpha Antigen

Alpha antigen is an abundantly-produced, secreted 30 kD mycobacterial protein involved in mycolic acid synthesis. During development of the present invention, it was determined that alpha antigen was a potentially useful indicator of mycobacterial disease, as it can account for up to 20% of the protein content of spent mycobacterial culture medium (A. Andersen et al., "Proteins released from *Mycobacterium tuberculosis* during growth," Infect. Immun., 59:1905–10 [1991]). In addition, homologous alpha proteins exist for most species of mycobacteria, including the *M. tuberculosis* and *M. avium* complexes. However, it is also contemplated that other antigens may be detected using the methods and compositions of the present invention.

The present invention provides rapid, reliable detection of mycobacterial antigens in such samples as body fluids (e.g., urine, blood and sputum) for the detection of various mycobacterial species, as the antigens have both species specific and shared epitopes (H. Tasaka et aL, "Specificity and distribution of alpha antigens of *Mycobacterium avium-intracellulare, Mycobacterium scrofulaceum*, and related species of mycobacteria," Am. Rev. Respir. Dis., 1985;132:173–4 [1985]). Furthermore, the genes for alpha antigens of *M. tuberculosis, bovis, avium*, and *kansasii*, have been cloned and sequenced (See e.g., K. Matsuo et al., "Cloning and expression of the gene for the cross-reactive alpha antigen of *Mycobacterium kansasii*," Infect. Immun., 58:550–6 [1990]; K. Matsuo et al., "Cloning and expression of the *Mycobacterium bovis* BCG gene for extracellular alpha antigen," J Bacteriol., 170:3847–54 [1988]; N. Ohara et al., "Cloning and sequencing of the gene for alpha antigen from *M. avium* and mapping of B-cell epitopes," Infect. Immun., 61:1173–9 [1993]; and L. DeWit et al., "Nucleotide sequence of the 85B-protein gene of *M. bovis* BCG and *M. tuberculosis:* DNA sequence," J. DNA Seq. Map., in press. [1996]).

At 30 kD), the alpha antigens may be too large to be filtered intact through the renal glomeruli, particularly when complexed with antibody, nonetheless, the present invention provides means to detect alpha antigens present in urine samples. While an understanding of the mechanism by which it is possible to detect the antigens in urine is not necessary to the successful practice of the invention, it is believed that cleavage of the protein may occur in vivo as a consequence of intracellular digestion by proteolytic enzymes within the macrophages, in the circulation, or in the kidney (e.g., by brush border peptidases), and permit excretion of the antigen or portions thereof. Antibody epitopes of alpha antigens of *M. bovis, M. leprae, M. tuberculosis*, and *M. avium* are largely restricted to the carboxy-terminal half of the protein (Ohara et al., "Cloning and sequencing of the gene for alpha antigen from *M. avium* and mapping of B-cell epitopes," Infect. Immun., 61:1173–9 [1993]; and E. Filley et al., "Identification of an antigenic domain on *Mycobacterium leprae* protein antigen 85B, which is specifically recognized by antibodies from patients with leprosy," J Infect. Dis., 169:162–9 [1994]). Thus, fragments representing the N-terminal portion of *M. tuberculosis* may be present in the urine, even if the native antigen is too large to be filtered by the glomeruli. It is contemplated that these fragments will be detected using the compositions and methods of the present invention.

The present invention provides numerous advantages over the methods previously and currently in use to detect infection and/or disease with *M. tuberculosis* or MAC. For example, all of the previously reported tuberculosis antigen detection assays were applied only to infected fluids or to early cultures, the assays were considerably less sensitive than this assay, and in addition, relied upon an animal antiserum developed against a whole organism of another mycobacterial species (BCG) for detection, resulting in poor specificity. Furthermore, none of the previously described assays were applied to urine and blood samples.

Also, the present invention detects products of the mycobacteria, rather than the host response to the organism. This provides an important advantage, as the host response is impaired in immunocompromised patients at highest risk of tuberculosis. Thus, tests such as those previously reported that are based on the host response are insufficiently sensitive in this population. In addition, the present invention permits detection of latent infection in individuals at highest risk of developing tuberculosis. This is significant, because once the infection is detected, preventive therapy can be initiated. This is not possible with the previously described methods.

Also, unlike the previously described methods, the present invention can be used for early monitoring of anti-tuberculosis therapy, providing a useful tool in predicting which individuals might experience treatment failure with a particular regimen. Thus, the present invention can also be used in the rapid evaluation of new anti-tuberculosis therapies.

Importantly for clinical diagnosis and public health tuberculosis clinics, the method of the present invention is rapid, requiring only 1–2 days to complete, as opposed to a minimum of 2–4 weeks for culture. Furthermore, the present invention can be performed during a single visit to the clinic, unlike the routine skin testing methods which require a return visit in order to observe and record the skin test results. Also importantly, the present invention provides an inexpensive method that is within the capabilities of existing clinical and public health mycobacteria laboratories. This is generally not true for methods that require specialized equipment and training (e.g., the polymerase chain reaction [PCR]). The test is very flexible, permitting the detection of various antigens or alpha antigen epitopes. The assay can be used to detect all secreted mycobacterial antigens by substituting a non-specific binding method for the capture antibody.

In addition, the results obtained by the present invention for detection of antigenuria are much superior to those of such previous methods as that of Sippola et al. (A. A. Sippola et al., "*Mycobacterium avium* antigenuria in patients with AIDS and disseminated *M. avium* disease," J. Infect. Dis., 168:466–8 [1993]). For example, as described in Example 16 of the present application, the K-II antiserum was found by Western blot of *M. avium* filtrate, to primarily recognize three antigens. One antigen was approximately 38–42 kD, and may be lipoarabinomannan (LAM), a mycobacterial polysaccharide. The second antigen is a 30 kD antigen that was determined to be alpha antigen. The third antigen was approximately 25 kD. This is significant for the reliable and reproducible detection of antigenuria, as these antigens differ considerably in terms of potential species-specificity. Antibodies to polysaccharides reach high levels in mycobacterial infection; however, they generally are broadly cross reactive and have limited diagnostic potential (S. D. Chaparas et al., "Tuberculin-active carbohydrate that induces inhibition of macrophage migration but not lymphocyte transformation," Science 170:637–9 [1970]; and A. Drowart et al., "Isoelectrophoretic characterization of protein antigens present in mycobacterial culture filtrates and recognized by monoclonal antibodies directed against the *Mycobacterium bovis* BCG antigen 85 complex," Scand. J. Immunol., 36:697–702 [1992]). It is contemplated that in addition to the alpha antigen, antigens such as the 25 kD antigen described in Example 16 will be detected in the present invention.

In contrast with the previous studies, the present invention provides a more sensitive method for the reliable detection of infection and/or disease due to *M. tuberculosis* or MAC, based on the detection of mycobacterial products, rather than the host response to the mycobacteria.

Definitions

To facilitate further understanding of the invention, a number of terms are defined below:

The terms "sample" and "specimen" in the present specification and claims are used in their broadest sense. On one hand, they are meant to include a specimen or culture. On the other hand, they are meant to include both biological and environmental samples. These terms encompasses all types of samples obtained from humans and other animals, including but not limited to, body fluids such as urine, blood, sputum, fecal matter, cerebrospinal fluid (CSF), semen, and saliva, as well as solid tissue. These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

Whether biological or environmental, a sample suspected of containing microorganisms may (or may not) first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be analyzed by the medium and method of the present invention.

As used herein, the term "culture" refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "organism" is used to refer to any species or type of microorganism, including but not limited to bacteria, yeasts and other fungi. As used herein, the term fungi, is used in reference to eukaryotic organisms such as the molds and yeasts, including dimorphic fingi.

As used herein, the term "Mycobacterium" is used in reference to the genus Mycobacterium, the only genus in the family Mycobacteriaceae. As used herein, the term "mycobacteria" is used in reference to all of the organisms included within the genus Mycobacterium, including all of the taxonomic levels lower than genus, including, but not limited to species, subspecies, strains, etc. As used herein, *M. tuberculosis* is used in reference to all of the species included within the "*M. tuberculosis* complex," including *M. tuberculosis, M. bovis, M. microti, M. africanum,* and any other organism subsequently recognized as falling within this taxonomic group.

As used herein, the terms "microbiological media" and "culture media," and "media" refer to any substrate for the growth and reproduction of microorganisms. "Media" may be used in reference to solid plated media which support the growth of microorganisms. Also included within this definition are semi-solid and liquid microbial growth systems including those that incorporate living host organisms, as well as any type of media.

As used herein, the term "primary isolation" refers to the process of culturing organisms directly from a sample. Thus, primary isolation involves such processes as inoculating an agar plate from a culture swab, urine sample, environmental sample, etc. Primary isolation may be accomplished using solid or semi-solid agar media, or in liquid. As used herein, the term "isolation" refers to any cultivation of organisms, whether it be primary isolation or any subsequent cultivation, including "passage" or "transfer" of stock cultures of organisms for maintenance and/or use.

As used herein, the term "presumptive diagnosis" refers to a preliminary diagnosis which gives some guidance to the treating physician as to the etiologic organism involved in the patient's disease. Presumptive diagnoses are often based on "presumptive identifications," which as used herein refer to the preliminary identification of a microorganism based on observation such as colony characteristics, growth on primary isolation media, gram stain results, etc.

As used herein, the term "definitive diagnosis" is used to refer to a final diagnosis in which the etiologic agent of the patient's disease has been identified. The term "definitive identification" is used in reference to the fmal identification of an organism to the genus and/or species level.

As used herein, the terms "digestion" and "decontamination" are used in reference to the standard methods used by mycobacteriology laboratories to treat samples such as sputum prior to culturing or testing the samples.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, equines, ovines, etc.).

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen or portion of an antigen.

As used herein, the terms "antigen fragment" and "portion of an antigen" are used in reference to a portion of an antigen. Antigen fragments or portions may occur in various sizes, ranging from a small percentage of the entire antigen to a large percentage, but not 100% of the antigen. However, in situations where at least a portion of an antigen is specified, it is contemplated that the entire antigen may be present. It is contemplated that antigen fragments or portions, may, but are not required to comprise an "epitope" recognized by an antibody. Antigen fragments or portions also may or may not be immunogenic.

As used herein, the term "immunoassay" is used in reference to any method in which antibodies are used in the detection of an antigen. It is contemplated that a range of immunoassay formats be encompassed by this definition, including but not limited to direct immunoassays, indirect immunoassays, and "sandwich" immunoassays." A particularly preferred format is a sandwich enzyme-linked immunosorbent assay (ELISA). However, it is not intended that the present invention be limited to this format. It is contemplated that other formats, including radioimmunoassays (RIA), immunofluorescent assays (IFA), and other assay formats, including, but not limited to, variations on the ELISA method will be useful in the method of the present invention. Thus, other antigen-antibody reaction formats may be used in the present invention, including but not limited to "flocculation" (ie., a colloidal suspension produced upon the formation of antigen-antibody complexes), "agglutination" (i.e., clumping of cells or other substances upon exposure to antibody), "particle agglutination" (i.e., clumping of particles coated with antigen in the presence of antibody or the clumping of particles coated with antibody in the presence of antigen); "complement fixation" (ie., the use of complement in an antibody-antigen reaction method), and other methods commonly used in serology, immunology, immunocytochemistry, histochemistry, and related fields.

As used herein, the term "cell staining" is used in reference to methods used to label or stain cells to enhance their visualization. This staining or labelling may be achieved through the use of various compounds, including but not limited to, fluorochromes, enzymes, gold, and iodine. It is contemplated that the definition encompasses such methods as "in situ chromogenic assays," in which a test (i.e., an assay) is conducted on a sample in situ. It is also contemplated that the in situ chromogenic assay will involve the use of an immunoassay (i.e., an ELISA).

As used herein, the term "capture antibody" refers to an antibody that is used to bind an antigen and thereby permit the recognition of the antigen by a subsequently applied antibody. For example, the capture antibody may be bound to a microtiter well and serve to bind mycobacterial antigens present in a sample added to the well. Another antibody (termed the "primary antibody") is then used to bind to the antigen-antibody complex, in effect to form a "sandwich" comprised of antibody-antigen-antibody. Detection of this complex can be performed by several methods. The primary antibody may be prepared with a label such as biotin, an enzyme, a fluorescent marker, or radioactivity, and may be detected directly using this label. Alternatively, a labelled "secondary antibody" or "reporter antibody" which recognizes the primary antibody may be added, forming a complex comprised of antibody-antigen-antibody-antibody. Again, appropriate reporter reagents are then added to detect the labelled antibody. Any number of additional antibodies may be added as desired. These antibodies may also be labelled with a marker, including, but not limited to an enzyme, fluorescent marker, or radioactivity.

As used herein, the term "reporter reagent" or "reporter molecule" is used in reference to compounds which are capable of detecting the presence of antibody bound to antigen. For example, a reporter reagent may be a calorimetric substance which is attached to an enzymatic substrate. Upon binding of antibody and antigen, the enzyme acts on its substrate and causes the production of a color. Other reporter reagents include, but are not limited to fluorogenic and radioactive compounds or molecules. This definition also encompasses the use of biotin and avidin-based compounds (e.g., including compounds but not limited to neutravidin and streptavidin) as part of the detection system. In one embodiment of the present invention, biotinylated antibodies may be used in the present invention in conjunction with avidin-coated solid support.

As used herein the term "signal" is used in reference to an indicator that a reaction has occurred, for example, binding of antibody to antigen. It is contemplated that signals in the form of radioactivity, fluorogenic reactions, and enzymatic reactions will be used with the present invention. The signal may be assessed quantitatively as well as qualitatively.

As used herein, the term "amplifier" is used in reference to a system which enhances the signal in a test method such as an ELISA.

As used herein, the term "solid support" is used in reference to any solid material to which reagents such as antibodies, antigens, and other compounds may be attached. For example, in the ELISA method, the wells of microtiter plates often provide solid supports. Other examples of solid supports include microscope slides, coverslips, beads, particles, cell culture flasks, as well as many other items.

As used herein, the term "kit" is used in reference to a combination of reagents and other materials. It is contemplated that the kit may include reagents such as capture antibody, reporter antibody, and amplifier.

DETAILED DESCRIPTION OF THE INVENTION

The present invention provides compositions and methods for the rapid detection of mycobacterial antigens in such samples as blood, serum, urine, sputum, and culture filtrates. Therefore, this invention provides significant advantages in the diagnosis, monitoring, and treatment of patients with infections and/or disease with such organisms as *M. tuberculosis* and MAC.

In particular, the present invention provides methods and compositions for an amplified ELISA method for the detection of the mycobacteria. In this method, two antibody preparations are used, namely a "capture" antibody and a "reporter" antibody (or "antibody pair"). The capture antibody is used to "capture" mycobacterial antigens present in a sample, in order to permit their detection upon the addition of the reporter antibody and amplifier system.

In a particularly preferred embodiment, the present invention provides compositions and methods for the detection of alpha antigen present in patient samples or other specimens. It is contemplated that the method be used to detect either the antigen or specific epitopes within the alpha antigen. It is not intended that the invention be limited to particular epitopes of the alpha antigen. Thus, it is also not intended that the present invention be limited to particular antibodies. For example, the capture antibody may be a monoclonal antibody directed against alpha antigen of *M. tuberculosis*, while the reporter antibody is a polyclonal or monoclonal antibody directed against an organism, such as *M. bovis* BCG.

Although embodiments have been described with some particularity, many modifications and variations of the preferred embodiment are possible without deviating from the invention.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); pg (picograms); l or L (liters); ml (milliliters); $\mu$l (microliters); cm (centimeters); mm (millimeters); $\mu$m (micrometers); nm (nanometers); OD (optical density); $OD_{492}$ (optical density at 492 nm); °C. (degrees Centigrade); PPD (purified protein derivative of *M. tuberculosis*, Connaught Laboratories, Ontario, Canada); PBS (phosphate buffered saline, Sigma); CHAPS detergent (3[3(3-Cholamidopropyll) diethylammonio]-1-propane-sulfonate); BSA (bovine serum albumin, Pierce); Tris (TRIZMA, Sigma); RPM (revolutions per minute); TBS (Tris buffered saline 0.05 M pH 8.0, Sigma). The following commercial enterprises or governmental agencies are identified as follows: Amersham (Amersham Life Science, Arlington Hts, Ill.); ATCC (American Type Culture Collection, Rockville, Md.); Becton Dickinson (Becton Dickinson Diagnostic Systems Instrument Systems, Sparks, Md.; Becton Dickinson Microbiology Systems, Cockeysville, Md.); BioRad (BioRad, Hercules, Calif.); Biowhittaker (Walkersville, Md.); Boehringer Mannheim (Indianapolis, Ind.); DAKO (DAKO, Carpinteria, Calif.); Difco (Difco Laboratories, Detroit, Mich.); Fisher (Fisher Scientific, Pittsburgh, Pa.); Isolator (Wampole Laboratories, Cranbury, N.J.); NCBI (National Center for Biotechnology Information, Bethesda Md., http://www3.ncbi.nlm.nih.gov/Entrez/index.html); NLM (National Library of Medicine, Bethesda Md.); Pierce (Pierce, Rockford, Ill.); S&S (Schleicher & Schuell, Keene, N.H.); Sigma (Sigma Chemical Co., St. Louis, Mo.); PGC (PGC Scientifics, Gaithersburg, Md.); Spectrum (Spectrum Medical Industries, Los Angeles, Calif.); U.S. Biochemical (U.S. Biochemical Corp., Cleveland, Ohio); Cambridge (Cambridge Diagnostics, Cambridge, Mass.); and Molecular Devices (Molecular Devices, Menlo Park, Calif.). Unless otherwise indicated, all of the chemicals used in the following Examples were obtained from Sigma.

EXAMPLE 1

Growth of *Mycobacterium tuberculosis*, Preparation of Culture Filtrates, Purification of Alpha Antigen, and Confirmation by Western Blot In this Example, cultures of *M. tuberculosis* were grown in order to produce culture filtrates for detection of alpha antigen. *M. tuberculosis* strain H37Rv was obtained from ATCC. Although ATCC #27294 was utilized in this Example, it is contemplated that other deposits of H37Rv (e.g., ATCC #25618, 35800, etc.) will be suitable for use in the present invention. Bacilli were cultured in Proskauer Beck medium in roller bottles at 37° C., at 5 RPM, in a humidified atmosphere for 10 weeks. Bacilli were removed by filtration using filter paper with progressively smaller pore size filters, up to 0.2μ (S & S). Ammonium sulfate (Sigma) was added to the liquid spent medium to a fmal concentration of 60% saturation at 3° C. The filtrate was refrigerated with constant magnetic stirring overnight. The resulting precipitate was sedimented at 2000 RPM. The liquid was removed, the precipitate resuspended in distilled water, and then was dialysed against a water bath using a 10 kD cutoff dialysis membrane (Spectrum).

The precipitated protein was applied to a diethylaminoethyl cellulose column (Sigma), washed with 0.01 M phosphate buffer, and then eluted with a linear gradient of from 0.01 M to 0.3 M sodium phosphate. Alpha antigen eluted at a salt concentration of 0.07 M. The antigen was concentrated by lyophilization, and then applied to a preparative isoelectric focusing cell (Rotofor chamber, Biorad), with 10 mg CHAPS detergent (Bio-Rad), 5 ml glycerol, and 1 ml pH 3–10 ampholytes (Bio-Rad), 1 ml pH 5–7 ampholytes (Bio-Rad) and a final volume of 55 ml. A constant power of 12 W was applied for 5 hr. The fractions containing alpha antigen were identified by SDS-PAGE and Western blot as described below. Selected fractions were then further fractionated by preparative SDS-PAGE using a PrepCell column (Bio-Rad) using a 10% acrylamide gel according to the manufacturer's recommendations. Protein fractions were collected from this column and were simultaneously concentrated and dialyzed using a cylindrical membrane device with a 10 kD cutoff (Micro-ProDiCon, Spectrum). Fractions containing pure alpha antigen were identified by SDS-PAGE, colloidal gold stain (Aurodye, Amersham), and Western blot.

SDS polyacrylamide gel electrophoresis was performed using 10% acrylarnide in the running gel, and 4% acrylamide in the stacking gel, in a Mini-Protean apparatus (Biorad) as suggested by the manufacturer. The protein to be electrophoresed was mixed with an equal volume of reducing sample buffer (Tris 1.51 g, pH 6.75, 4% SDS, 20% glycerol, and 10 µl 2-mercaptoethanol suspended to 100 ml in $H_2O$), and boiled for 2 minutes prior to application to the gel. After electrophoresis, the sample was transferred to 0.2µ pore size nitrocellulose paper (S&S).

Western blotting was performed by blocking nonspecific binding with 5% bovine fetal serum (BioWhittaker) and 5% bovine serum albumin (BSA, Sigma) in phosphate buffered saline (Sigma). The antibody was diluted from 1:10 to 1:5000, as needed (i.e., depending upon the starting concentration), in wash buffer with 1% BSA, and was incubated with the nitrocellulose blot overnight with constant rocking at 0.5 RPM at room temperature. The blot was washed twice for 5 minutes in PBS with Tween 20 0.1% (Sigma). An alkaline phosphatase conjugated secondary antibody (Sigma) was diluted 1:500 in PBS with 1% BSA and incubated for 6 hr with rocking at room temperature. The blot was washed twice as above. The blot was then added to 30 ml of a solution of 100 mM Tris, 100 mM NaCl, 5 mM $MgCl_2$, with 50 mg nitroblue tetrazolium and 5 mg 5-bromo-4-chloro-3-indoyl phosphate. Development was stopped by washing in water.

These methods were satisfactory for purification of alpha antigen (85-B) from its related antigen 85-A, which differs only slightly in molecular size but more substantially by isoelectric point. A blot of *M. tuberculosis* alpha antigen purified by this approach is shown in FIG. 1. In this Figure, lane "a" contained *M. tuberculosis* culture filtrate as the antigen and the stain on this lane was colloidal gold. Lane "b" of FIG. 1 contained alpha antigen purified as described above and the stain was also colloidal gold. Lane "c" of FIG. 1 contained alpha antigen identical to lane b and stained with biotinylated TBC27.

EXAMPLE 2

Production of Murine Monoclonal Antibody

The monoclonal antibody designated as TBC27 was produced for use in the ELISA method of the present invention. This monoclonal was developed by immunization with *M. tuberculosis* alpha antigen obtained using the methods of Example 1. Six week-old female Balb/c mice (Charles River, Mass.) were immunized with 50 $\mu$g alpha antigen in incomplete Freund's adjuvant (DIFCO, Detroit, Mich.). Twice, animals were boosted with additional 50 $\mu$g of antigen at two week intervals, and sacrificed 2 weeks after the last boost. Spleen cells were fused to SP2/0 Ag 14 myeloma cells (ATCC) using polyethylene glycol (Sigma), and were propagated in Dulbecco's modified Eagle' medium (Sigma) with added hypoxanthine, aminopterin, and thymidine. Supernatants of wells with visible growth were tested for antibody by ELISA. The wells of Immulon 2 plates (PGC) were sensitized overnight (i.e., 12–18 hours), with 50 $\mu$l *M. tuberculosis* filtrate (10 $\mu$g/ml), and 25 $\mu$l of 3% glutaraldehyde in 0.15 M sodium phosphate. The plates were washed with wash buffer (TBS with 0.1% Tween-20). Supernatants from hybridoma wells were added to the wells and allowed to incubate overnight at room temperature, with rocking at 5 RPM. The plates were washed with wash buffer. Antibody was detected using alkaline phosphatase-conjugated anti-mouse Ig (Sigma) and alkaline phosphatase, as recommended by the manufacturer (Sigma). Wells found to be positive for antibody production were expanded in culture, through the use of standard methods for expansion of monoclonal antibody-producing clones. The supernatants were collected, lyophilized, and dialyzed. The antibody was biotinylated using the ImmunoPure NHS LC-biotin kit (Pierce) and the manufacturer's recommendations.

An immunoadsorbent column was prepared using ImmunoPure immobilized strepavidin (Pierce) according to the manufacturer's recommendations. Biotinylated TBC-27 was passed twice over the column. The column was regenerated between passes, according to the manufacturer's recommendations. The preadsorbed TBC-27 was used in subsequent studies for the antigen detection ELISA, as described below.

EXAMPLE 3

Detection of Alpha Antigen in *M. tuberculosis* Culture Filtrates

In this Example, an ELISA method (C. J. Stanley et al, "Enzyme amplification can enhance both the speed and the sensitivity of immunoassays," J. Immunol. Meth., 83:89–95 [1985]; and C. H. Self, "Enzyme amplification—a general method applied to provide an immunoassisted assay for placental alkaline phosphatase," J. Immunol. Meth., 76:389–93 [1985]) that substantially increases the speed and sensitivity of ELISA, was extensively modified for use for the detection of alpha antigen, including the addition of another step. In this method, an alkaline phosphatase conjugate was used to convert NADP to NAD, which then entered a regenerating cycle leading to production of a colored formazan dye. A schematic of the reaction is shown in FIG. 2. Its use in the alpha antigen assay has resulted in over a 1000 fold reduction in the lower limit of detection of the assay (ie., from 20 ng/ml, to from 1 to 10 pg/ml). The samples used in this pilot study were culture filtrates obtained from cultures of *M. tuberculosis* grown as described in Example 1.

In this method, 100 $\mu$l biotinylated TBC27 diluted 1:1000 in BSA blocker (Pierce) in TBS was added to each well of neutravidin-precoated ELISA plates (commercially available from Pierce). After 2 hr, the plate was washed with wash buffer (TBS/Tween 20 0.1%). Further nonspecific binding was inhibited by adding 300 $\mu$l SuperBlock (Pierce) twice, as per the manufacturer's recommendations.

Standards (*M. tuberculosis* filtrate, with a 10% alpha antigen content as determined by densitometry of colloidal gold stained gels) and samples were diluted with equal volumes of an appropriate buffer depending on the nature of the experiment. For example, in assays comparing mycobacterial filtrates of different species, or of sputum samples, the diluent was TBS. For serum or urine, the diluent was pooled serum or urine (respectively) obtained from a group of healthy individuals with no known TB exposure, no residence in a TB endemic area, no history of BCG vaccination, a PPD skin test reaction of 0 mm induration within the past year, and no history of a reaction of greater than 0 mm in the past. The diluted standards, and the samples, were then diluted with an equal volume of BSA blocker in TBS. One hundred μl was then added to each well. Standards were tested in duplicate, and samples were tested in individual wells. The plate was incubated overnight on a rocking table at 5 RPM in a humidor. The plate was washed 3 times with washing buffer. 100 μl of 1:1000 anti-BCG rabbit serum (commercially available from DAKO) preabsorbed with biotinylated TBC27 using an avidin column as described in Example 2, was added and allowed to incubate at room temperature overnight (i.e., 18–20 hours).

The plate was washed as above, and 100 μl alkaline phosphatase-conjugated anti-rabbit Ig (commercially available from Pierce) diluted 1:5000 in BSA Blocker in TBS was added, and allowed to incubate for 2 hours with rocking as described above. The plate was then washed again as described above. To the washed plate, 100 μl amplifier (NADP+0.02 mM (Boehringer) in 50 mM diethanolamine (Sigma), 1 mM $MgCl_2$ (Sigma), 0.1 mM $ZnCl_2$, (Sigma), and 15 mM $NaN_3$ (Sigma), at pH 9.5) was added to each well. The plate was incubated for 10 minutes at room temperature, during which time NAD was generated. Then, 200 μl diaphorase-dehydrogenase mixture was added (2 mg/ml alcohol dehydrogenase (Sigma), 1.5 mg/ml diaphorase (Boehringer), 4% ethanol (Sigma), 0.55 mM INT-violet (Sigma), 5 mg/ml BSA (Sigma), at pH 7.2). After 5 minutes of incubation time, the $OD_{492}$ was measured using a Maxline microplate reader (Molecular Devices). A four-parameter standard curve relating concentration to optical density was generated using SoftMax computer software (Molecular Devices).

Because background signal is often the limiting factor in amplified assays, several measures were undertaken to reduce background signal in this assay. First, the antiserum used for detection (anti-BCG rabbit serum) of the alpha antigen was reabsorbed by passing it over a streptavidin column to which biotinylated TBC27 (ie., the primary antibody) had been coupled. This was done to remove nonspecific reactivity against mouse IgG as well as specific alpha-anti-idiotypic antibody. Second, a conjugated anti-rabbit-Ig was selected which had been depleted of reactivity with murine and human IgG. Third, biotin/avidin was used to fix the capture antibody to the plate; this in turn allowed for more vigorous washing protocols with a detergent-containing buffer. Fourth, particular blocking reagents (BSA Blocker and SuperBlock, Pierce) were used, and albumin devoid of alkaline phosphatase activity was selected (Pierce). Finally, several sources of NADP were tested to identify reliable sources of NADP which contained the least amount of contaminating NAD. In multiple reproductions of this Example, it was determined that the best source of NADP was Boehringer, whereas that from Sigma was inferior.

Figure 3:
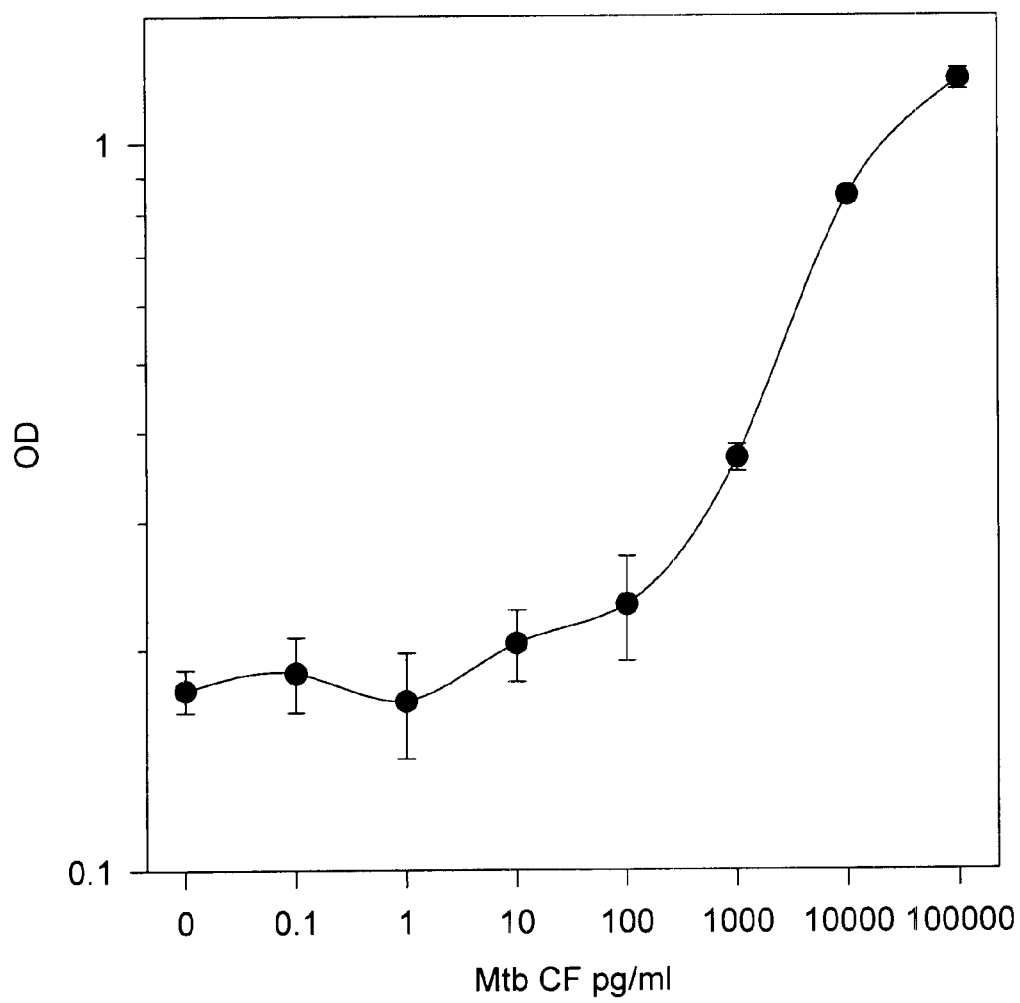

The results of this example are shown in FIG. 3. Data in this figure are presented on a log-log scale to show its wide dynamic range. The horizontal axis reflects total protein content of M. tuberculosis culture filtrate; of this, alpha antigen represented approximately 10%, as estimated by densitometric measurement of proteinstained gels. Thus, the lower limit of detection of the assay was approximately 1 pg/ml.

EXAMPLE 4

Recovery of M. tuberculosis Alpha Antigen in Spiked Samples

Figure 4:
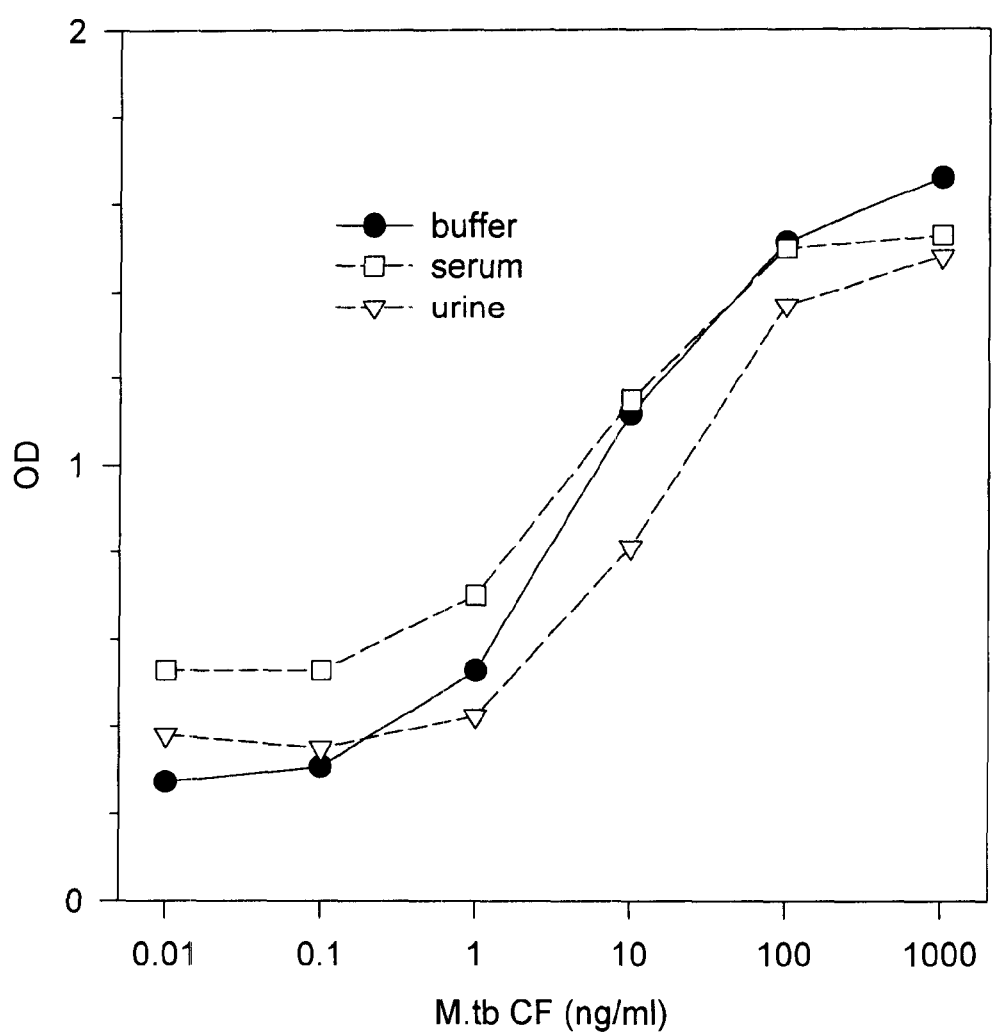

In this Example, the same methods as described in Example 3 were used for testing of serum or urine, with the exception that M. tuberculosis culture filtrates were added to normal pooled normal human serum or urine, as described above. This experiment was conducted in order to determine whether alpha antigen from M. tuberculosis filtrate could be detected in such samples. The results of this experiment are shown in FIG. 4. As can be seen from FIG. 4, the sensitivity of the assay was not substantially affected by either diluent (i.e., normal serum or urine). However, the study suggests that separate diluents for standards be used, depending upon the type of clinical sample.

EXAMPLE 5

Radiometric Detection of M. tuberculosis Compared to Alpha Antigen Detection

Radiometric detection of growth of mycobacteria is the standard to which clinical laboratories are held for rapid diagnosis of tuberculosis by accrediting agencies such as the Joint Commission on Accreditation of Healthcare Organizations (JCAHO). Thus, it was of interest to compare a commonly used radiometric method with the ELISA method of the present invention for the detection of M. tuberculosis.

For clinical samples of infected body fluids (e.g., sputum, etc.), standard methods of specimen processing are used, including decontamination and concentration. These samples are then inoculated into special radiometric medium which contains $^{14}C$-radiolabelled palmitic acid. For the BACTEC system (Becton Dickinson), metabolic activity of any organisms in the culture bottle results in production of $^{14}CO_2$. The gas above the liquid medium in the bottle is sampled daily and the $^{14}CO_2$ content measured. The result is expressed as a growth index (GI). GI values above 20–30 are considered positive. Cultures with positive growth indices must then be examined using other methods in order to identify the organism(s) present.

Figure 5:
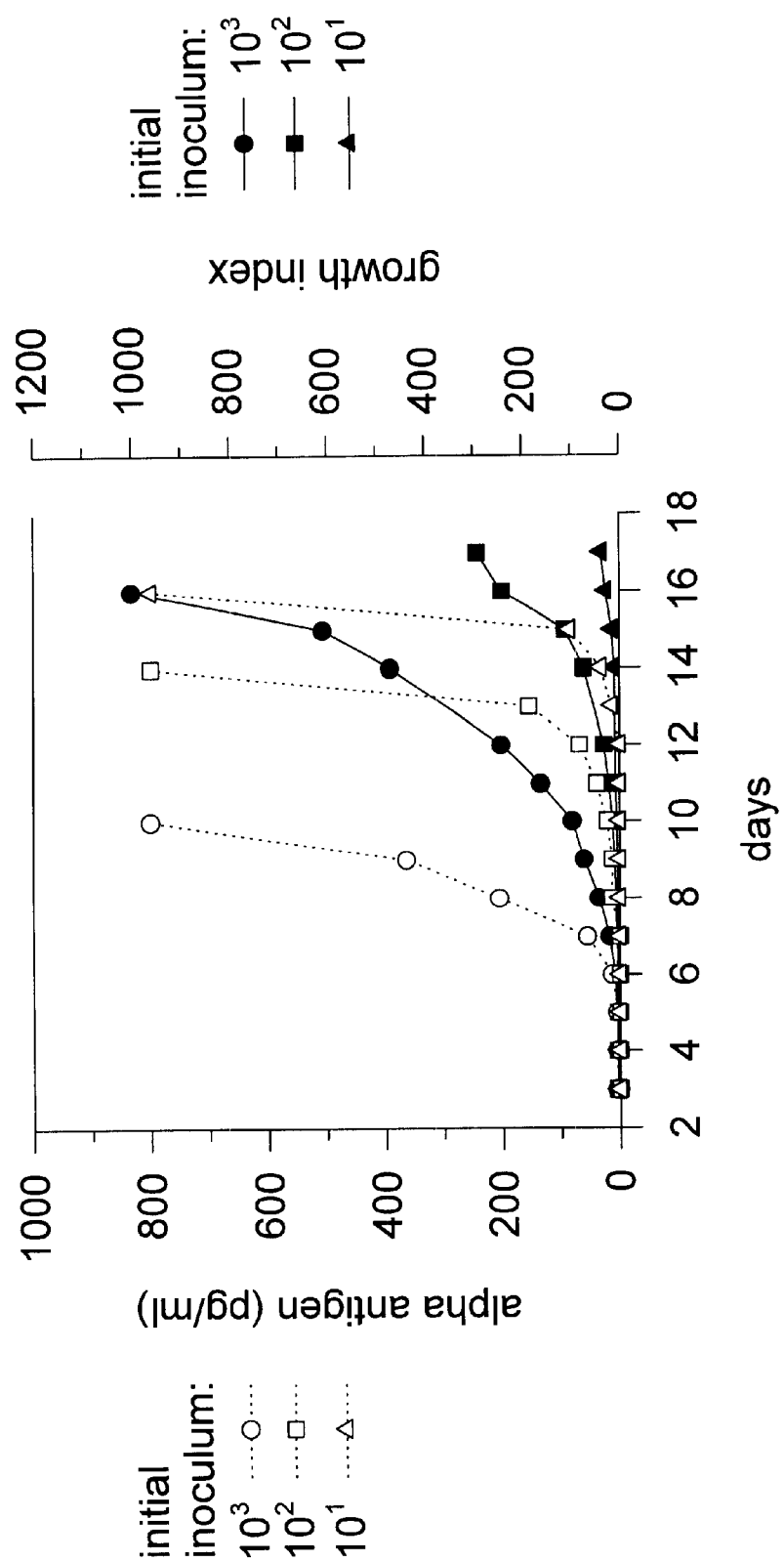

As in the previous Example, BACTEC 14B bottles supplied by the manufacturer were inoculated with from $10^4$ to $10^1$ colony forming units (CFU) of M. tuberculosis strain H37rv. Growth indices were measured daily as recommended by the manufacturer; simultaneous samples were collected for measurement of alpha antigen using the ELISA method of the present invention. On each day of measurement, 0.2 ml of medium was removed from the BACTEC bottle for measurement of alpha antigen, and an equal volume of fresh medium was replaced. The results of this study are shown in FIG. 5. In FIG. 5, solid data points represent growth index (GI) values, while the open data points represent alpha antigen content. The lower limit of detection of alpha antigen in this experiment was 10 pg/ml. Clinical samples are generally scored as positive when growth indices reach 30. The time to positivity of the two assays is summarized in Table 1:

TABLE 1

Comparison of BACTEC and Amplified ELISA

| Inoculum | Days to GI > 30 | Alpha Antigen Concentration at GI = 30 | Days to Alpha Antigen > 10 pg |
|---|---|---|---|
| $10^4$ | 5 | 61 | <4 |
| $10^3$ | 8 | 205 | 6 |
| $10^2$ | 12 | 68 | 8 |
| $10^1$ | 17 | >800 | 13 |

Thus, regardless of inoculum size, growth was detected from 2 to 4 days earlier by the antigen detection assay of the present invention, as compared to radiometric assay.

EXAMPLE 6

Radiometric Detection of *M. avium* Compared to Alpha Antigen Detection

In view of the importance of *M. avium*, the methods described in Example 5 above were used with a culture of *M. avium* replacing the *M. tuberculosis* culture used in the previous Example. This *M. avium* culture was a clinical isolate obtained from the blood of an AIDS patient with disseminated *M. avium* infection. This culture was propagated in Proskauer Beck medium as described above, with the exception that 1% dextrose was added to the culture medium.

It was found that the amplified ELISA assay system was substantially less sensitive for detection of M. avium alpha antigen than for *M. tuberculosis*. Antigen was detected only simultaneously or within one day of positive GI values. Despite more rapid growth of *M. avium*, antigen levels were less than 10% of those found with *M. tuberculosis*. Table 2 shows the results observed in this experiment.

TABLE 2

M. avium Detection

| Initial CFU | Days to GI > 30 | Days to Alpha Antigen > 10 pg/ml |
|---|---|---|
| $10^4$ | 4 | 4 |
| $10^3$ | 5 | 5 |
| $10^2$ | 6 | 6 |
| $10^1$ | 8 | 7 |

Nonetheless, these results indicate that the present invention may be used for the detection of alpha antigen in culture filtrates.

EXAMPLE 7

Alpha Antigen Detection in Urine and Serum of HIV-Negative Tuberculosis Patients In this Example, urine and serum obtained from Ugandan tuberculosis patients not infected with HIV, as well as tuberculosis-negative, HIV-negative controls were tested using the amplified ELISA assay described in Example 3.

These HIV-negative patients with tuberculosis had presented to the Uganda TB Control Programme referral center at Mulago Hospital, Kampala, the clinical site of the Case Western Reserve University TB Research Unit. Pulmonary tuberculosis was diagnosed on the basis of a compatible chest radiograph, a positive sputum AFB smear, and confirmatory growth of *M. tuberculosis* on culture of sputum. These patients were determined to be HIV-1 uninfected by commercial serum ELISA test system (Cambridge). Urine and serum specimens were obtained for antigen detection assay prior to initiation of therapy for tuberculosis.

Control subjects without tuberculosis were identified from among patients under treatment for conditions other than tuberculosis, at the Pulmonary Clinic at Mulago Hospital. Their diagnoses were asthma and chronic bronchitis. None of these patients were known or suspected to be HIV-infected. Given the prevalence of HIV infection in Kampala (approximately 8%) it is unlikely that more than one subject in this group was HIV-infected. However, in view of the prevalence of PPD skin test reactivity in Kampala (approximately 70% in HIV uninfected persons; reviewed in M. Schulzer et al., "An estimate of the future size of the tuberculosis problem in sub-Saharan Africa resulting from HIV infection," Tuber. Lung Dis., 73:52–8 [1992], and the published erratum which appears in Tuber. Lung Dis., 73(4):245–6 [1992]), it is likely that 14 of the subjects in this group had been infected with *M. tuberculosis*. Assuming a lifetime risk of tuberculosis of 10% in *M. tuberculosis*-infected HIV-negative persons, and 70% in *M. tuberculosis*-infected HIV-positive persons, it is likely that approximately one subject in this cohort will develop tuberculosis in the future due to recrudescence of latent infection.

Figure 6:
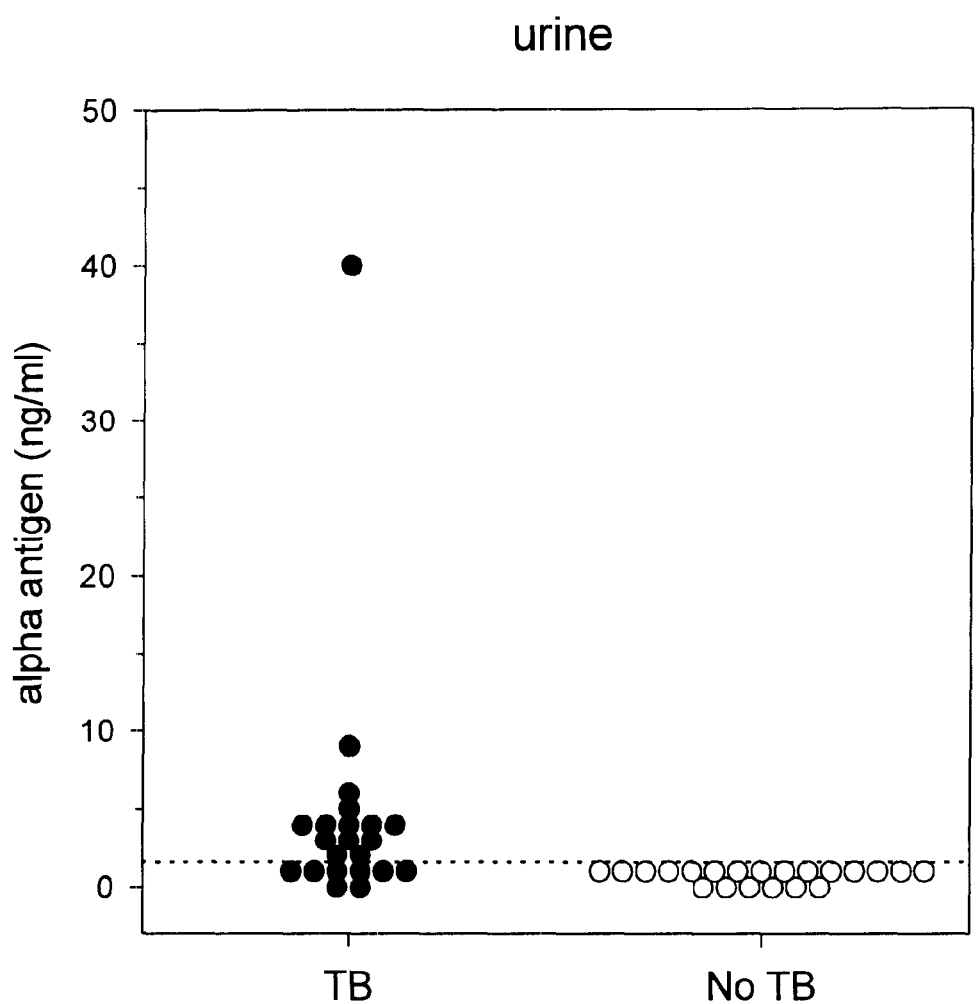
Figure 7:
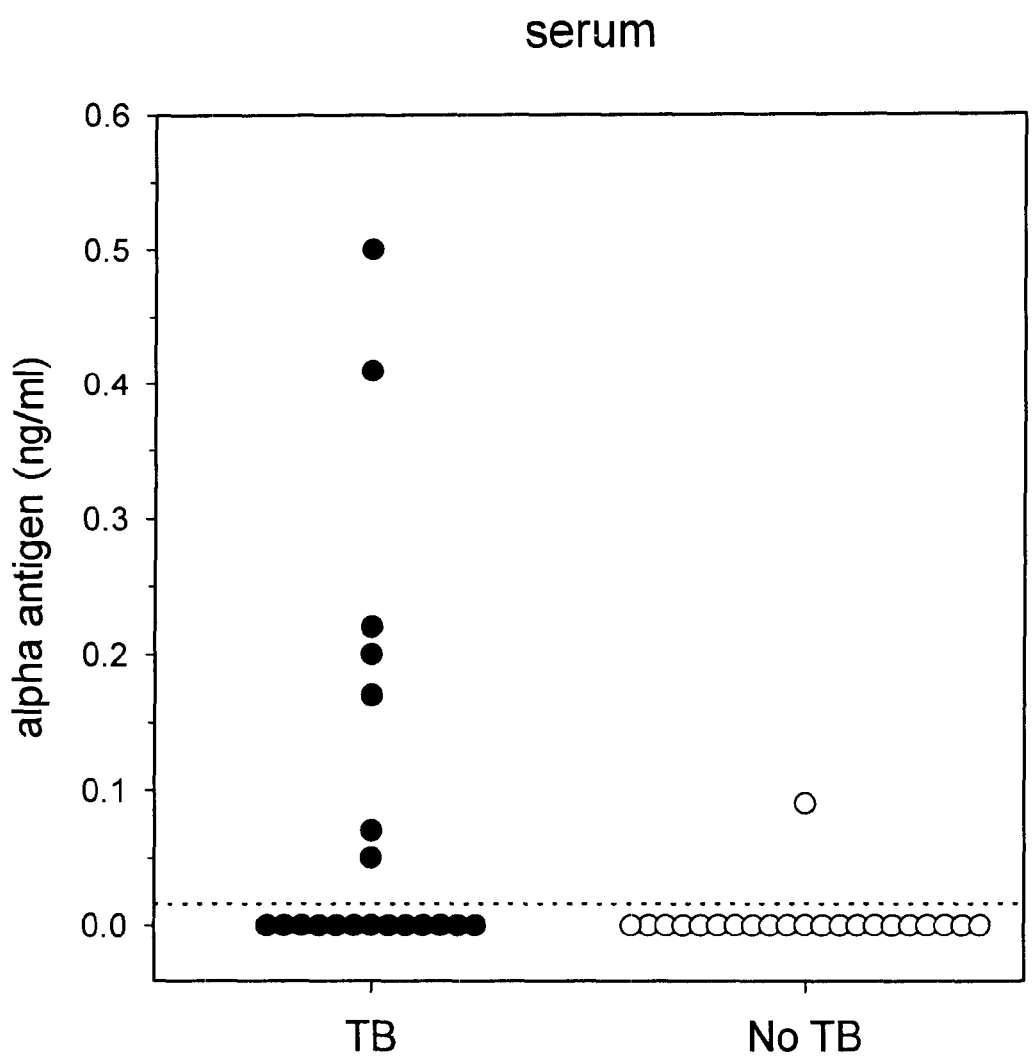

The amplified ELISA test system of Example 3 was used to test serum and urine of these patients. For this experiment, cutoff values of 2 ng/ml and 20 pg/ml for urine and sputum, respectively, were selected. At these values, the sensitivity and specificity of the assay with these specimens were determined. For serum samples from non-tuberculosis patients, 21 were found to be negative, while one was positive. For serum samples from tuberculosis patients, 13 were found to be positive, while seven were found to be negative. Thus, for serum samples, the sensitivity was 35%, and the specificity was 95%. For urine samples from non-tuberculosis patients, 21 were found to be negative, and none were found to be positive. For urine samples from tuberculosis patients, eight were found to be negative, while 13 were found to be positive. Thus, for urine samples, the sensitivity was 62%, and the specificity was 100%. FIG. 6 graphically shows the results with the urine, while FIG. 7 shows the results with the serum samples from these patients.

EXAMPLE 8

Alpha Antigen Detection in Urine of HIV-Positive Tuberculosis Patients

In this study, urine samples from two cohorts of HIV infected subjects were tested using the ELISA assay described in Example 3. The first cohort was composed of Ugandan patients and the second was composed of HIV patients from Cleveland, Ohio. The Ugandan HIV-infected patients were diagnosed with tuberculosis based on the observation of a tuberculosis-compatible chest radiograph, a positive sputum AFB smear, and confirmatory growth of *M. tuberculosis* on culture of sputum. These patients were determined to be HIV-1 infected by the same commercial serum ELISA test described in Example 7.

A control Ugandan group, composed of Ugandan HIV-infected patients without tuberculosis was identified in the course of evaluation and enrollment in tuberculosis preventive therapy studies in Uganda. These individuals had originally presented at anonymous HIV testing centers in Kampala, were found to be seropositive, and were referred to the Case Western Reserve University tuberculosis center for possible enrollment in preventive therapy studies. These subjects had normal chest radiographs, and had negative sputum AFB smears and cultures. The mean CD4 count of this group was 360/µl.

The second cohort included HIV-infected patients with disseminated *M. avium* infection identified through the Cleveland AIDS Clinic or hospital ward, on the basis of a positive blood, bone marrow, or lymph node culture. Three individuals were being treated for their MAC disease at the time the urine cultures were collected,, although one individual was included in this study two weeks before the diagnosis was established. Three additional individuals were studied at the time of diagnosis but prior to initiation of therapy.

A control group of HIV-infected subjects without MAC or tuberculosis were identified at similar locations in Cleveland. Several subjects had multiple blood cultures for suspected *M. avium* disease, but none were positive. The mean CD4 count of this group was 280/µl.

Figure 8:
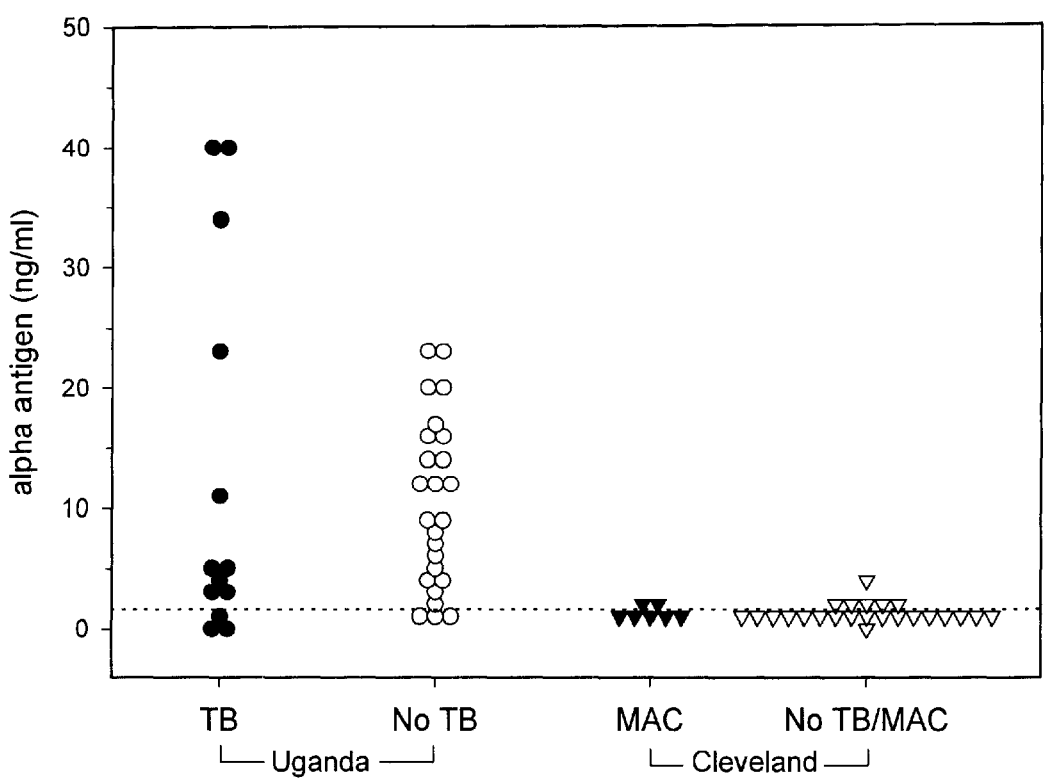

The same cutoff (2 ng/ml) was used as in Example 7. The results for detection of urinary alpha antigen in this example are shown in FIG. 8. These results indicated that the sensitivity (77%) was increased from that in HIV-uninfected subjects in Example 7. Apparent false positives were observed in 22 of 25 HIV-infected Ugandans without tuberculosis. However, using the estimates in this group, it is likely that 18 were actually infected with *M. tuberculosis*, and 12 may develop tuberculosis due to recrudescence of latent infection. The positive values in this subgroup may therefore reflect production of alpha antigen by tubercle bacilli contained within granulomas.

EXAMPLE 9

Detection of Alpha Antigen in Urine

Subjects for this example were identified as follows: patient with untreated pulmonary tuberculosis were identified on the basis of a positive sputum acid fast smear with culture confirmation, and a chest radiograph compatible with pulmonary tuberculosis at the Tuberculosis Treatment Centre, Kampala, Uganda. All subjects with tuberculosis were tested for HIV by ELISA. A 10% random sample of positives were confirmed by Western blot for quality assurance (using a commercial kit from BioRad). Although CD4 cell counts were not determined in this group, recent studies performed in a similar cohort (newly diagnosed HIV+ pulmonary tuberculosis) at this site found a median CD4 cell count of 343/µL.

HIV-infected Ugandans without tuberculosis were enrolled through their participation in a placebo control arm of a study of preventive therapy for tuberculosis in HIV-infected persons. These subjects had chest films and sputum cultures at regular intervals which were negative for tuberculosis. The median CD4 cell count of this group was 355/µL.

Ugandans without tuberculosis, and who were not known to be HIV-infected, were recruited through the Chest Clinic at Mulago Hospital, Kampala. This group consisted of patients with chronic bronchitis or asthma, normal chest radiographs, not known to be HIV seropositive, and never having had *M. tuberculosis* identified in sputum, and not known to ever have been treated with any antituberculous drugs. Based on the prevalence of HIV seroreactivity and tuberculin skin test reactivity in Kampala, approximately 15 (70%) of these subjects were likely to PPD positive, and no more than 1–2 (10%) were likely to be HIV seropositive. Approximately half of the Ugandan population was vaccinated once with BCG in infancy. However, tuberculin skin test reactivity in Ugandan adults is not affected by the administration of BCG during infancy (ie., as indicated by the presence of a BCG scar); this is thought to reflect infection with *M. tuberculosis*.

HIV-infected persons at low risk for tuberculosis were recruited at University Hospitals, Cleveland, Ohio, through the AIDS Clinical Trials Unit. The incidence of tuberculosis among American-born persons in the greater Cleveland area was 3.2/100,000 in 1994, one of the lowest among metropolitan areas in the United States. Subjects from this site were studied if they were not known to have disseminated MAC, tuberculosis, or a history of a positive tuberculin skin test, and had not emigrated from a country with a high risk of tuberculosis, and had not been given preventive therapy for tuberculosis. The other HIV-related infectious diagnoses in this group included six patients with *Pneumocystis carinii* pneumonia (PCP), five patients with cytomegalovirus (CMV) infection, eight patients infected with herpes simplex virus or herpes zoster, five patients with candidiasis, one patient with toxoplasmosis, one patient with syphilis, one patient with cryptococcosis, two patients with tracheobronchitis due to Xanthomonas or Pseudomonas, and two patients with unspecified hepatitis. The median CD4 cell count of this patient group was 170/µl.

Subjects from this site identified with disseminated *M. avium* infection (MAC) were diagnosed on the basis of positive blood or lymph node culture in the setting of a compatible clinical presentation. Two of the 7 subjects had simultaneous blood cultures which were positive and had not yet begun treatment for MAC. The median CD4 cell count of this group was 20/µl.

Persons at low risk for HIV infection were identified among laboratory and university personnel. Subjects in this group who had not previously had a positive tuberculin skin test, and who had not been tested within the past year, were skin tested tested after urine collection. Information was collected from these subjects regarding BCG vaccination and country of origin. Subjects were excluded if they had been given preventive therapy for tuberculosis.

Tuberculin skin testing was performed by the Mantoux method using 5 T.U. (tuberculin units) with PPD. Induration was read at 48 hr. Results were scored as positive if induration was ≧5 or 10 mm in HIV-infected and uninfected subjects, respectively. In healthy American subjects, only a 0 mm response was read as negative, and subjects with reactions of from 1 to 9 mm were not included in the study.

Dual color flow cytometry was performed for enumeration of CD3+ and CD4+ cells. Growth of *M. tuberculosis* on culture was confirmed by standard methods, based on colonial morphology on Lowenstein-Jensen medium, nitrate and niacin positivity, and resistance to 5% thiopencarboxylic acid hydrazine.

Alpha antigen was detected by ELISA using a biotinylated monoclonal antibody TBC27 as described in Example 3. A standard curve was generated using serial dilutions of *M. tuberculosis* culture filtrate in which the alpha antigen content was determined by densitometric analysis of colloidal gold stained blots, in parallel with Western blot using TBC27, as described in Example 1. Pooled urine from PPD skin test-negative healthy subjects was used as a diluent for the standard. *M. tuberculosis* filtrate was prepared by precipitation in ammonium sulfate of spent Proskauer Beck medium from 8 week cultures of *M. tuberculosis* strain H37Rv, as previously described in Example 1. *M. avium* filtrate was similarly prepared with the exception that the spent medium was supplemented with 1% dextrose (i.e., as described in Example 6.

Figure 9:
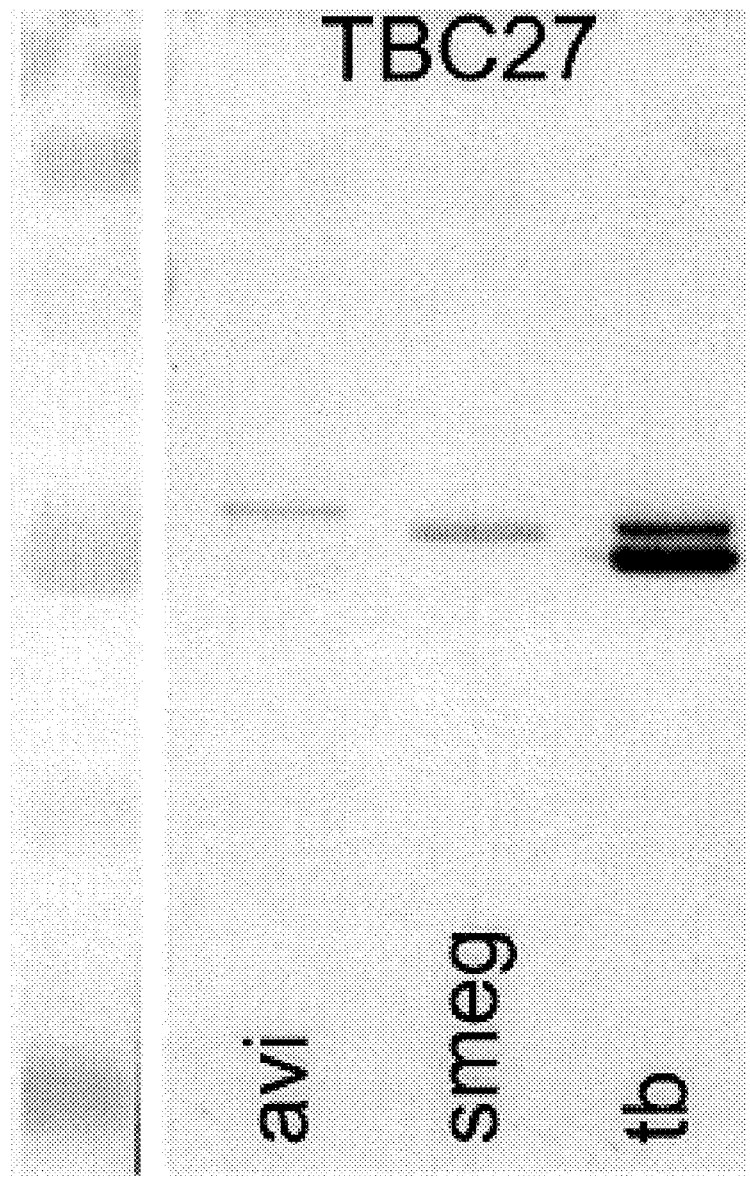
Figure 10:
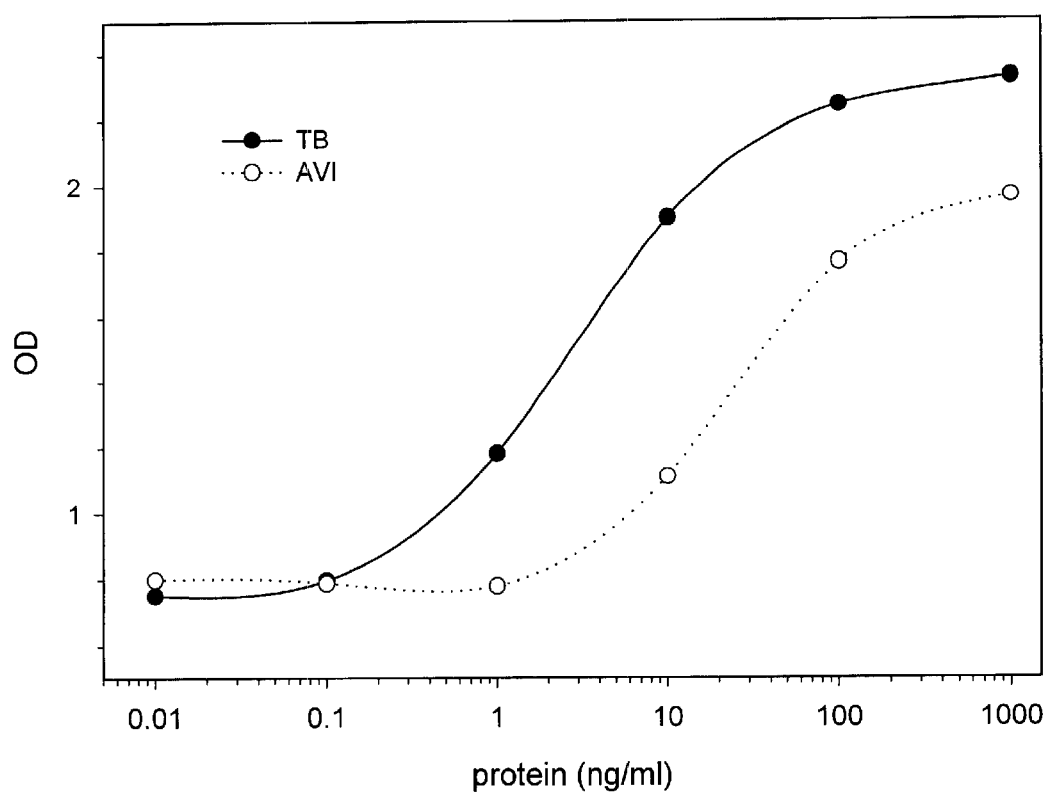
Figure 11:
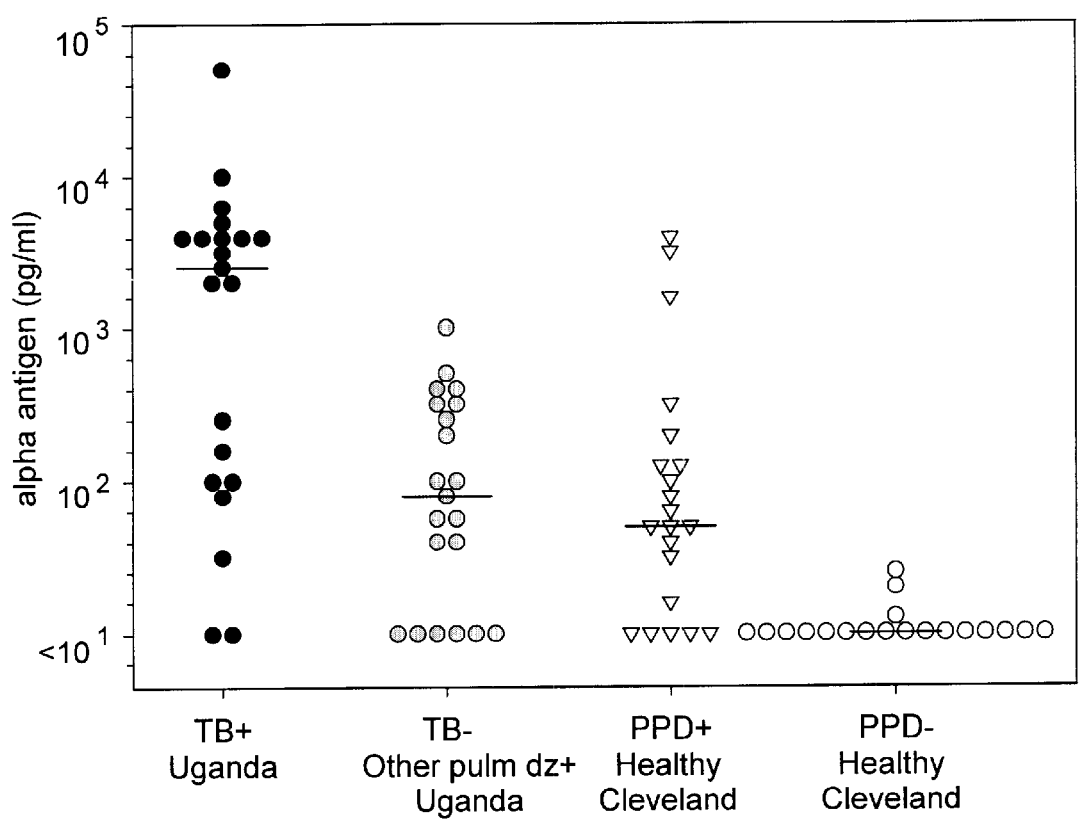
Figure 12:
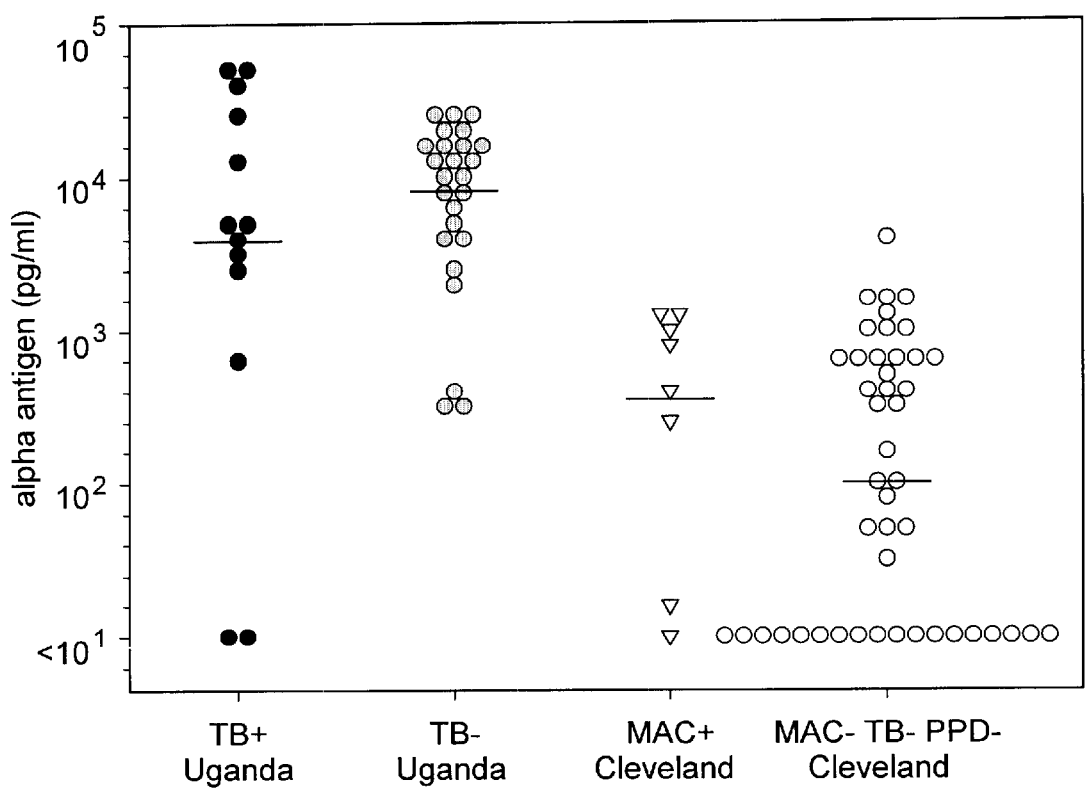
Figure 13A:
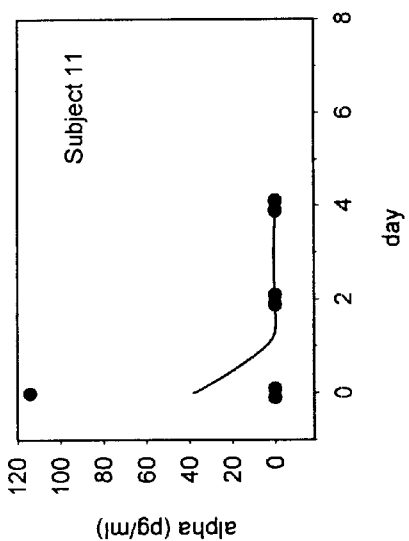
Figure 13B:
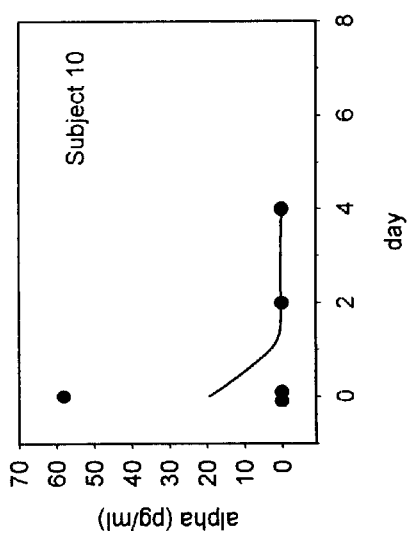
Figure 13C:
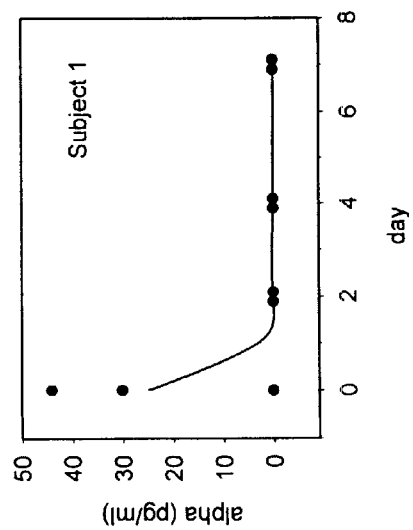
Figure 14C:
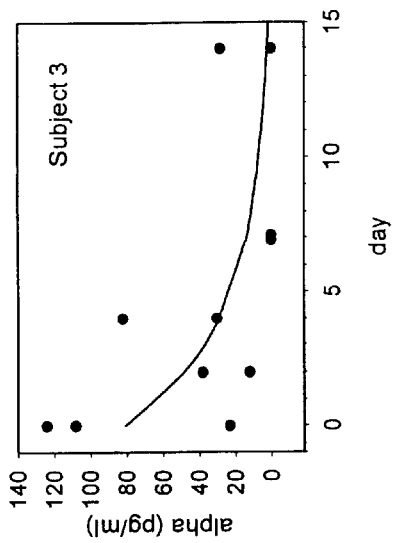
Figure 14B:
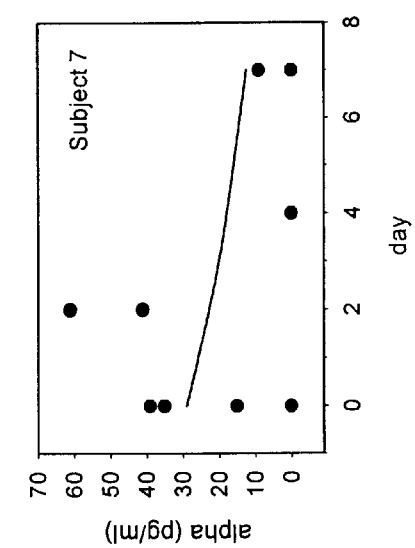
Figure 14A:
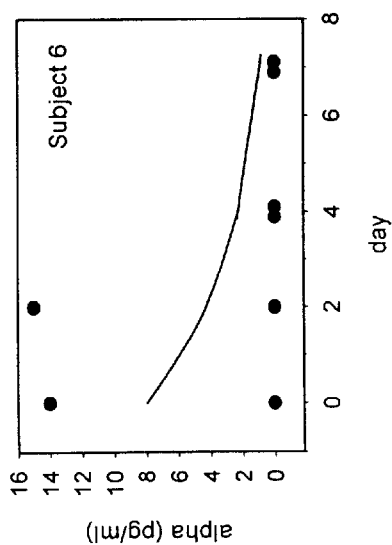
Figure 14D:
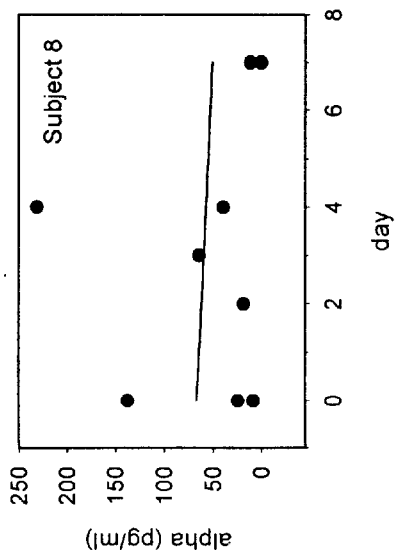
Figure 14E:
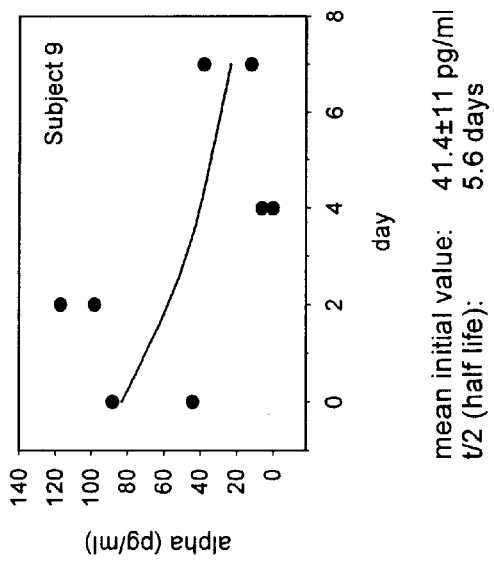
Figure 14F:
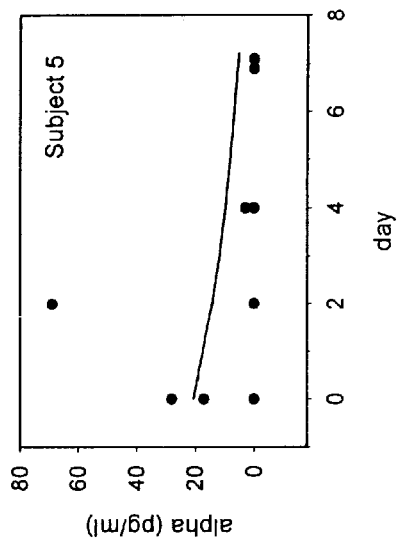
Figure 15:
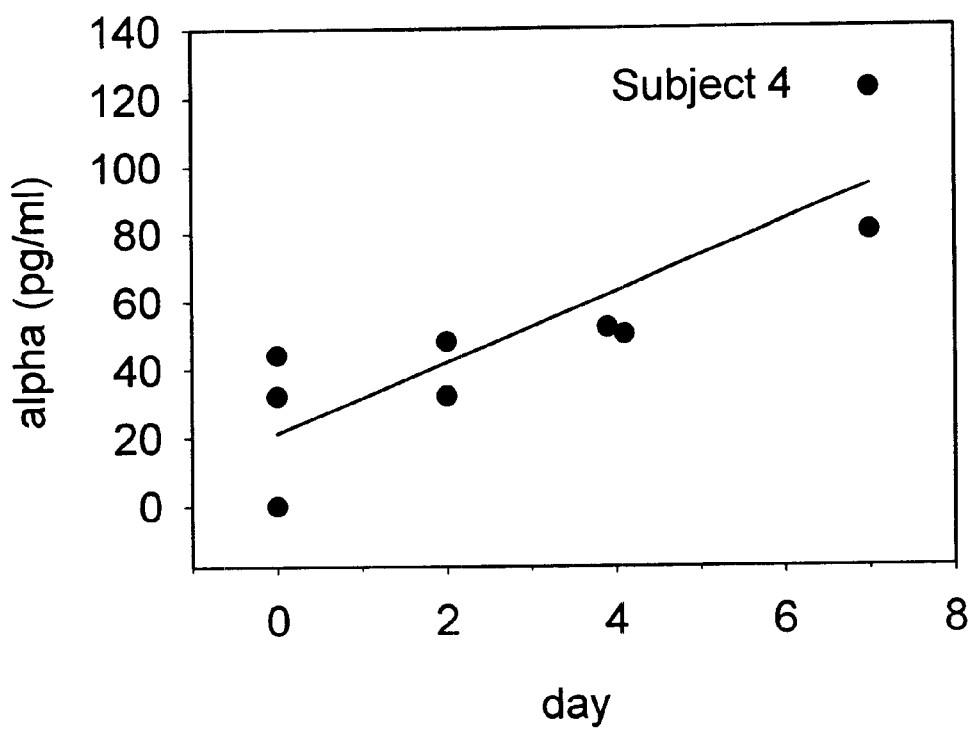
Figure 16:
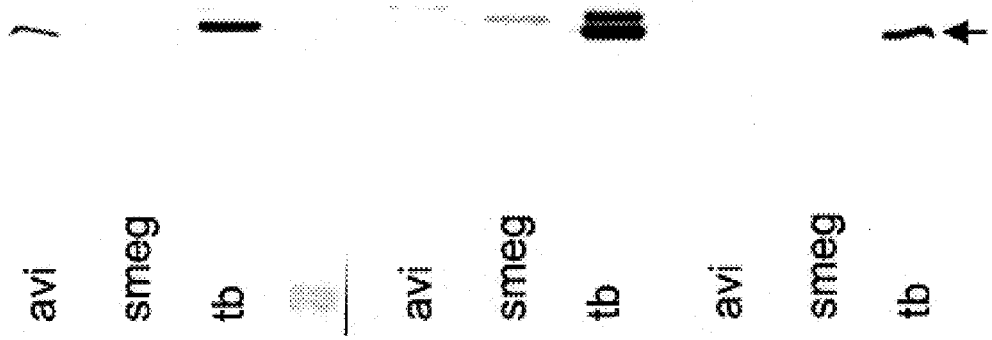
Figure 17:
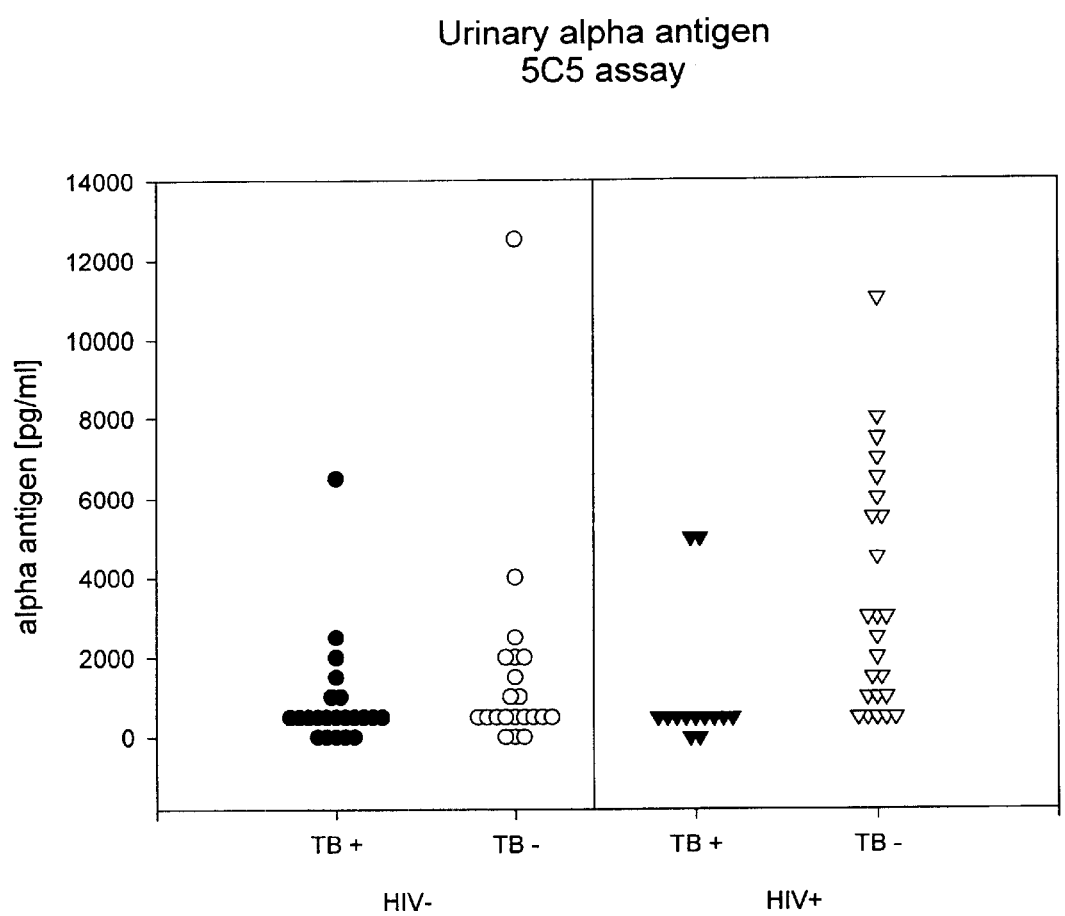
FIG. 17 shows the results of alpha antigen detection assays from urine samples of HIV-positive and HIV-negative individuals.
Figure 18:
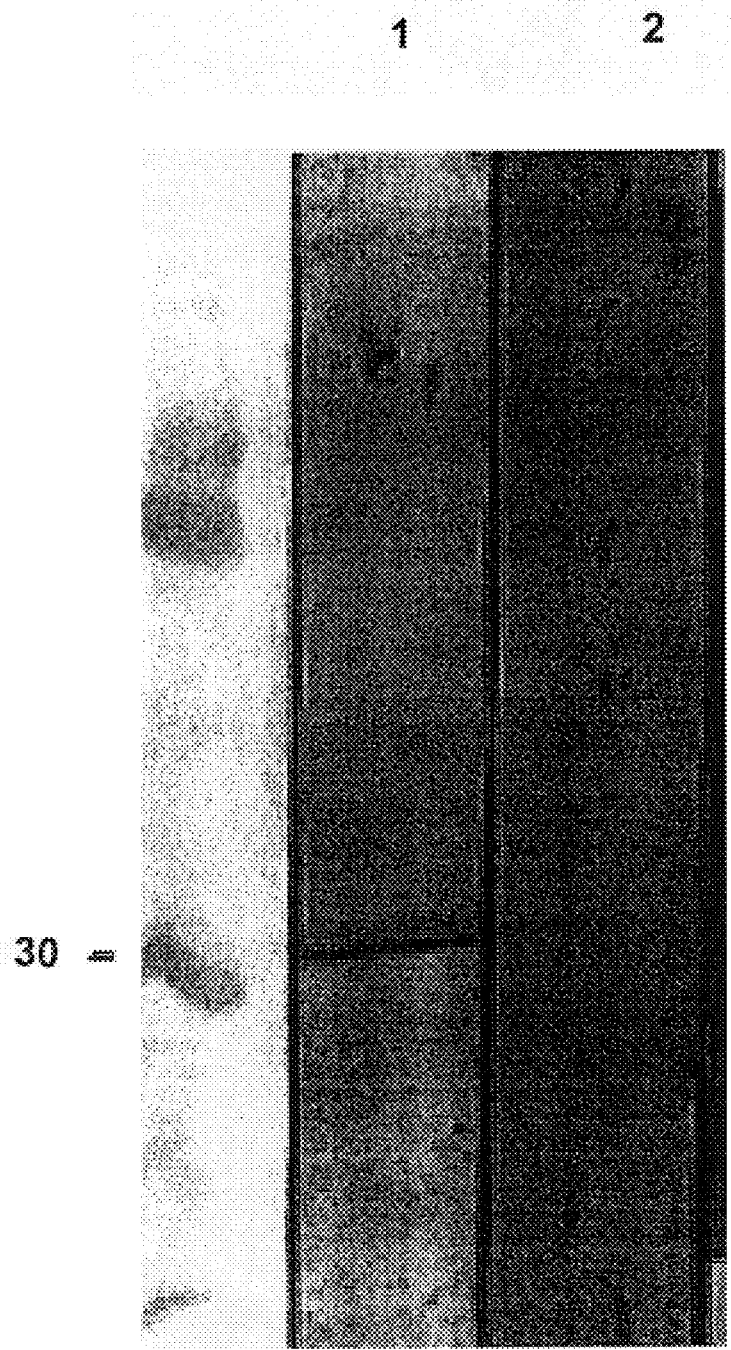
FIG. 18 shows a Western blot in which 5C5 was used to detect alpha antigen.

The relative specificity of the capture monoclonal antibody for alpha antigen of *M. tuberculosis* when tested by western blot is shown in FIG. 9. As shown in this Figure, there is a band of reduced intensity in the *M. avium* lane, as compared with the *M. tuberculosis* lane. Representative standard curves using culture filtrates of *M. tuberculosis* and *M. avium* are shown in FIG. 10. In FIG. 10, the horizontal axis reflects total protein content of the respective mycobacterial filtrates. In *M. tuberculosis* filtrate, alpha antigen represents approximately 10% of total protein, as estimated by densitometric measurement of colloidal gold-stained blots. Thus, the threshold for detection of alpha antigen in this assay was approximately 10 pg/ml, although in some experiments it was found to be as low as 1 pg/ml. The mid-range sensitivity of the assay for M. avium was found to be 12-fold less sensitive than that for M. tuberculosis, when the two filtrates were compared based on total protein content. Approximately half of this difference can be accounted by the reduced alpha antigen content of M. avium filtrate (5% instead of 10% of total protein).

At high protein concentrations, the assay was found to become progressively less sensitive for M. avium filtrate, approaching a 100-fold difference at 1 µg/ml. In effect, this limited the maximum response to *M. avium* filtrate to the equivalent of 1–2 ng/ml *M. tuberculosis* alpha antigen. Additional specificity for *M. tuberculosis* may arise from differential secretion of proteins by the two species, in that following infection with equal numbers of organisms in Proskauer-Beck medium, growth of *M. avium* is more rapid, but results in a lower concentration of secreted protein.

Urinary alpha antigen levels were then evaluated in several groups of subjects, identified as follows, and represented in FIGS. 11 and 12. The results varied according to the TB and HIV status of the subjects. Log-transformed urinary antigen determinations from these subjects are presented in these figures, so that differences between groups can be distinguished over a wide range of values. As shown in these Figures, among HIV-seronegative subjects, antigenuria was greatest in subjects with active untreated pulmonary tuberculosis. In this group, the median value was 2.24 alpha antigen (per mg/ml). Sixty-two percent of this group had values of 2 ng/ml or greater. Intermediate values were observed in two groups of subjects with latent infection with *M. tuberculosis.* These groups included Ugandan pulmonary clinic subjects with asthma and bronchitis, and healthy PPD-positive personnel from the American university cohort. None of the subjects in either group had received preventive therapy for tuberculosis. The degree of antigenuria did not differ between these two groups (median values of 79 and 50 pg/ml, respectively, in Ugandan and American subjects). Urinary antigen was undetectable in all but 2 of the skin test negative healthy American subjects. Only 1 of 18 subjects had antigenuria of >2 ng/ml.

Among all HIV-seronegative subjects, the median values differed significantly among those with active tuberculosis, those with latent infection, and those who by skin test were uninfected, using the Kruskal-Wallis analysis of variance of ranks ($p<0.001$). The non-parametric ANOVA equivalent was used because the data failed a test of normality. All three possible pair wise comparisons also differed significantly ($p<0.05$, using Dunn's method).

Antigenuria was greater in the corresponding groups of HIV-infected subjects. For example, in HIV-infected Ugandans with and without tuberculosis, median urinary antigen levels were 4.3 and 8.3 ng/ml, respectively ($p<0.001$ for both when compared to corresponding HIV-negative groups). The median urinary alpha antigen value in AIDS patients with disseminated MAC was 510 pg/ml; in those without MAC, it was 79 pg/ml. Antigenuria of >2 ng/ml was observed in only one subject without epidemiologic or culture evidence for *M. tuberculosis* infection. Among all HIV-positive subjects, the median values differed by Kruskal-Wallis rank ANOVA ($p<0.001$). Pairwise comparisons showed differences between either Ugandan group and either Cleveland group ($p<0.05$), but not in other comparisons.

In HIV-seronegative persons, values of ≧2 ng/ml were diagnostic of active tuberculosis with a sensitivity of 62% and a specificity of 98%. Intermediate values (between 33 pg/ml and 2 ng/ml) were consistent with either latent infection or active disease. These findings suggest that the mycobacteria in latently infected persons are not dormant, but rather are metabolically active. Thus, it is contemplated that the antigen detection assay may have potential application to distinguish those skin test positive individuals with viable *M. tuberculosis* from those whose infection has been eradicated, either by preventive therapy or a protective immune response. This may allow for greater selectivity in application of preventive therapy for tuberculosis.

No antigen could be detected in approximately 10% of Ugandan tuberculosis patients regardless of HIV status. Antibodies to other pathogens such as HIV can be detected in urine; it is possible that pretreatment of urine specimens to dissociate alpha antigen immune complexes might increase the sensitivity of the assay. Alternatively, it is possible that these patients may be infected with another member of the *M. tuberculosis* complex such as *M. africanum,* about which relatively little is known regarding alpha antigen genetics or biology.

Urinary antigen levels in HIV-infected persons were, in general, higher than in HIV-seronegative persons, and the conclusions which can be drawn from test results are somewhat more limited. Values of >2 ng/ml were found only in subjects with active tuberculosis, or with likely exposure to tuberculosis based on epidemiologic factors. This degree of antigenuria in HIV-infected persons may be used as an indication for either tuberculosis chemotherapy or preventive therapy, depending on the results of additional tests. In this application, the antigen assay had a sensitivity of 84% and a specificity of 98%.

Unlike in HIV-seronegative subjects, the degree of antigenuria in HIV-infected subjects did not differ between those with latent infection vs. active disease. The reason for this is not known. Many of the HIV-positive subjects who were studied had very high antigen levels (>10 ng/ml). Thus, it is preferred that the sample contain antigen levels that are less than or equal to 10 ng/ml. It is contemplated that for samples with very high antigen levels (i.e., >10 ng/ml), dilution of the sample to an antigen concentration lower than 10 ng/ml may be desirable prior to analysis. Alternatively, it is possible that in dually-infected (HIV and *M. tuberculosis*) persons, the total mycobacterial burden may not be the main determinant of clinical disease, and that other factors, possibly immunologic, may be important in determining whether the infection causes clinical illness.

Values between 33 pg and 2 ng/ml were identified in many HIV-infected Cleveland subjects who were without either active tuberculosis or epidemiologic evidence suggesting tuberculosis exposure. These levels were significantly greater than in HIV seronegative PPD skin test negative controls. The etiology of these results is not certain, but it may reflect latent infection with to *Mycobacterium avium.* The apparent clustering of values in the range of 1–2 ng/ml in samples from these subjects is consistent with the behavior of the assay with *M. avium* filtrate. Disseminated infection with organisms of the *Mycobacterium avium-intracellulare* complex (MAC) is the most common opportunistic infection late in the course of HIV disease. The frequency of disease due to MAC rises from 3% per year for individuals with CD4 counts of 100–200/μl to 39% at CD4 counts of <10/μl.

EXAMPLE 10

Detection of Alpha Antigen in Sputum

In this Example, detection of alpha antigen was studied in sputum obtained from patients at the initiation of anti-tuberculosis therapy. In this study, multiple sequential expectorated sputum samples were obtained during the first two weeks of anti-tuberculosis therapy from a group of HIV-uninfected AFB smear-positive subjects who presented to the Case Western Reserve University tuberculosis research unit site at Vittoria, Brazil. The sputum samples were homogenized by adding 10 mg N-acetyl cysteine (Sigma) and 10 3 mm diameter glass beads (Fisher) to each 5–10 ml sputum sample. The samples were vortexed at room temperature for 1 minute. Aliquots of 200 µl were frozen at −70° C. until analysis. A total of 37 pretreatment specimens was obtained from 13 subjects. Using the amplified ELISA method described in Example 3, the mean alpha antigen concentration in the positive specimens was determined to be 51 pg/ml. Every subject had at least one positive pretreatment specimen for a total of 28/37 or 76% positive.

Subsequent sputum specimens were also available on days 2, 4, 7, and 14 post initiation of treatment, from 10 patients. The alpha antigen concentrations in these subsequent specimens from these subjects are shown in FIGS. 13A–15. In these Figures, the results from one patient are shown in each panel. For three patients, only the pre-treatment specimen was determined to positive, and all subsequent specimens were negative. The results from this group of patients are shown in FIGS. 13A–13C, with FIG. 13A showing the results for "Subject 1,"; FIG. 13B, showing the results for "Subject 10,"; and FIG. 13C showing the results for "Subject 11." In these patients, the mean initial value obtained in the amplified ELISA was determined to be 27±13 pg/ml. The length of time alpha antigen was detectable in these specimens expressed in terms of half-life was determined to be 0.6 days.

In nine of the 10 patients for which multiple sputum were tested, at least one subsequent specimen was positive. The results for these nine patients are shown in FIGS. 14A–14F, in panels A–F, with one patient's results being shown in each FIGS. 14A–14F. As can be seen from this Figure, this group of patients tended to have higher initial antigen concentration than the first group, although this difference did not reach statistical significance (i.e., the mean initial value was 41.4±11 pg/ml). The rate of disappearance of antigen from subsequent specimens from this group was found to be slower than in the first group, with a half-life of 5.6 days.

In one patient, the level of sputum alpha antigen rose during treatment, as shown in FIG. 15. Simultaneous quantitative CFU rose more than 10 fold during this interval. Quantitative CFU did not increase in any of the other subjects during this interval.

These results indicate that the amplified ELISA method for detection of alpha antigen in sputum is suitable for detection of infection and/or disease with *M. tuberculosis*. Importantly, these results indicate that this ELISA method provides significant information for monitoring the progress of tuberculosis patients.

EXAMPLE 11

Production of Other Monoclonal Antibodies for Alpha Antigen Detection

In addition to TBC27 described and used in Example 3 above, other antibodies were produced for potential application in the purification and detection of alpha antigen of *M. tuberculosis*. These antibodies were developed by immunization six week-old female Balb/c mice (Charles River, Mass.) using the method of intrasplenic immunization (P. C. Svalander et al., "Intrasplenic immunization for production of monoclonal antibodies against mouse blastocysts," J. Immunol. Meth., 105:221–7 [1987]). Mice were immunized with 1 μg alpha antigen obtained from *M. tuberculosis* culture filtrate as described in Example 1. The portion of the nitrocellulose paper containing the alpha antigen was excised and the paper allowed to dry at room temperature. The paper was dissolved in DMSO (Sigma). It was then precipitated by the dropwise addition of sodium carbonate 0.05 M (Sigma), pH 9.6. The precipitated particles were then washed 3 times in 2 ml RPMI-1640 medium (BioWhittaker) and suspended in a final volume of 1 ml. The immunization was performed by injection into the spleen, using a 25 gauge needle. Animals were boosted with additional 1 μg twice at two week intervals, and sacrificed 2 weeks after the last boost. Spleen cells were fused to SP2/0 Ag 14 myeloma cells (ATCC) using polyethylene glycol (Sigma) and were propagated in Dulbecco's modified Eagle' medium (Sigma) with added hypoxanthine, aminopterin, and thymidine. Supernatants of wells with visible growth were tested for antibody by ELISA using plates sensitized with *M. tuberculosis* filtrate as described in Example 2. Positive wells were expanded in culture, and the supernatants collected and lyophilized, and the antibody was biotinylated using a biotinylation reagent kit (Pierce) according to the manufacturer's recommendations, all as described in Example 2.

Several antibodies specific for *M. tuberculosis* alpha antigen were developed using the methods of this Example, including the antibody designated as "5C5," and "8G104.4." As shown in the Western blot in FIG. 16, 5C5 and 8G10.4.4 reacted only with culture filtrates of *M. tuberculosis* and not *M. smegmatis* or *M. avium*. Thus, it is contemplated that these antibodies will also be useful in the amplified ELISA assay and provide increased specificity. However, with 5C5, cross-reactivity was observed, as described in Example 12.

EXAMPLE 12

Use of 5C5 for Detection of Alpha Antigen in Urine

In this Example, antibody 5C5 produced as described in Example 11 above was tested for its ability to detect *M. tuberculosis* alpha antigen in urine. The amplified ELISA method and patient groups described in Example 7 were used, with the exception that instead of using TBC27, 5C5 was used (i.e.,the samples were retested with 5C5 in place of TBC27).

The results of this study are shown in FIGS. 17 and 18. As shown in FIG. 17, this antibody was capable of detecting antigen in urine. However, as shown in FIG. 18, an apparent specificity to *M. tuberculosis* as determined by Western blot (see FIG. 16) does not ensure success in the diagnosis of tuberculosis, as cross reactivity can arise. In FIG. 18, lane 1 contained *M. tuberculosis,* while lane 2 contained *M. avium* filtrate. As shown in FIG. 18, when biotinylated 5C5 was substituted for TBC27 in the alpha antigen ELISA, the test was of less value than the use of TBC27 for tuberculosis diagnosis, regardless of HIV status (ie., the results were of no value for either the HIV-positive or HIV-negative patient groups). The spurious results were in part due to unexpected cross reactivity of the antibody with proteins expressed on the surface of normal human monocytes, detected by immunohistochemistry of infected cells.

EXAMPLE 13

Use of Synthetic Peptides to Produce Monoclonals Specific for Alpha Antigen of *M. tuberculosis*

In this Example, the possibility of using synthetic peptides to produce antibodies directed against *M. tuberculosis* alpha antigen was investigated. The amino acid sequences of the alpha antigens of M. avium and M. tuberculosis are compared in FIG. 19 (SEQ ID NOS: 1 and 2). In this Figure, residues which differ between the two species are emphasized in bold face. As shown in this Figure, extensive identity is apparent (87%) between the alpha antigens of these two species.

Upon inspection, potentially species-specific peptides were identified beginning at amino acid residues 147 and 229 of M. tuberculosis (SEQ ID NOS: 3 and 4). SEQ ID NO: 3 is comprised of the amino acid sequence "QWLSAN-RAVKPTGSAAI"; while SEQ ID NO: 4 is comprised of the amino acid sequence "ERNDPTQQIPKLVAN."

These peptides were hypothesized as representing sections that were specific to particular species of Mycobacterium. Searches were performed using the Entrez database search engine at the National Center for Biotechnology Information at the National Library of Medicine. This search engine is based on a program developed by S. F. Altschul termed "BLASTP," which is used to identify homologous sequences in the combined PDB, SwissProt, PIR, GenPept, and GPupdate databases (S. F. Altschul et al., "Basic local alignment search tool," J. Mol. Biol., 215:403–10 [1990]). A facility to search these databases for homologous sequences has been established by the National Library of Medicine, and was accessed by the Internet at URAL http://www3.ncbi.nlm.nih.gov/Entrez/index.html. The search engine allows the user to supply an amino acid sequence. It returns a list of all potentially homologous sequences which have been stored in its database. The engine is designed to identify sequences which are identical, which have similar amino acid residues in terms of charge or size, which have intervening inserted sequences, or which have deletions. However, in the comparison, the "expect" search parameter was increased from a default of 10 to 1000 to increase the reporting of even marginal matches.

As a control, a similar search was performed for a 17 amino acid intervening sequence "DQFIYAGSLSALLDPSQ" (SEQ ID NO: 5), which begins at residue 181 of the *M. avium* antigen sequence, and represents a consensus region that is shared among the species of the Mycobacterium genus. This sequence differs by one amino acid from the homologous stretch in the *M. tuberculosis* amino acid sequence. In the *M. tuberculosis* sequence, the first "D" is replaced with a "Q" (i.e., the entire sequence is "QQFIYAGSLSALLDPSQ" (SEQ ID NO: 8).

The results of these three searches are shown in the following Tables. These data were divided into four tables. The first table (Table 3) shows the comparisons for strains of mycobacteria. The second table (Table 4) shows the comparisons for various potential human pathogens. The third table (Table 5) shows the comparisons for various human peptides. The fourth table (Table 6) shows the comparisons for peptides from other organisms.

The data in these Tables are displayed as the percent identity/homology between the target sequences and its best match in another species. Those matches with ≧65% identity or ≧80% homology are highlighted in bold. Items marked with an asterisk (*) required folding of at least one sequence for optimal alignment; the degree of homology of these matches is likely overestimated. No homologous sequences were identified for those entries left blank.

TABLE 3

Search Results for Peptides from Various Mycobacteria and Three Peptide Sequences of Alpha Antigen of M. tuberculosis (% identity/% homology)

| | Amino Acid 147 | Amino Acid 229 | Amino Acid 181 |
|---|---|---|---|
| M. tuberculosis | | | |
| 85-B | 100/100 | 100/100 | 100/100 |
| 85-A | 71/76 | 58/76 | 70/88 |
| 85-C | 59/76 | 76/88 | 53/65 |
| M. bovis | | | |
| 85-B | 100/100 | 100/100 | 100/100 |
| Bovis antigen | 71/76 | 58/76 | 70/88 |
| 85-A | 71/76 | 58/76 | 70/88 |
| MPB51 | 53/71 | | |
| M. avium 85-B | 47/82 | 58/82 | 100/100 |
| M. intracellulare Alpha Antigen | 58/88 | 70/82 | 94/100 |
| M. kansasii 85-B | 88/100 | 70/88 | 94/100 |
| M. scrofulaceum Alpha Antigen | 64/94 | 82/88 | 94/100 |
| M. leprae | | | |
| 85-A | 52/88 | 58/76 | 70/76 |
| 85-B | 70/83 | 70/76 | 81/93 |
| 85-C | 59/76 | 76/88 | 53/65 |

TABLE 4

Search Results for Various Human Pathogens and Three Peptide Sequences of Alpha Antigen of M. tuberculosis (% identity/% homology)

| | Amino Acid 147 | Amino Acid 229 | Amino Acid 181 |
|---|---|---|---|
| Coxiella trxB, spoIIIE | | 35/59* | |
| D-ala-D-ala Carboxypeptidase | | | 41/76* |
| Aspergillus P450 53 | | 59/82* | |
| E. coli tus | 35/53* | | |
| Corynebacterium iron protein | | 35/53 | |
| Simian Paramyxovirus | | 59/82* | |
| Bacillus cellulase | | 41/65* | |
| Bacillus δ endotoxin | 35/71 | | |
| Human Adenovirus | | 53/76* | |
| Human Rotavirus A | | 59/59* | |
| Human Herpesvirus | | 29/71 | |
| Hepatitis C | | 29/35* | |
| Candida p450 | | | 41/65 |
| Saccharomyces | | | 53/82* |
| Yeast DNA helicase | | | 53/82* |

TABLE 5

Search Results for Human Peptides and Three Peptide Sequences of M. tuberculosis (% identity/% homology)

| | Amino Acid 147 | Amino Acid 229 | Amino Acid 181 |
|---|---|---|---|
| Tyrosine phosphatase | 41/76* | | |
| Testican | 65/71* | | |
| Isocitrate dehydrogenase | | | 35/47 |
| T-cell receptor d Chain | 29/53 | | |
| TEGT (Testis enhanced gene transcript) | | | 53/59* |
| Granulocyte Colony Stimulating Factor | | | 41/53 |

TABLE 6

Search Results for Various Organisms and Three Peptide
Sequences of Alpha Antigen of M. tuberculosis
(% identity/% homology)

|  | Amino Acid 147 | Amino Acid 229 | Amino Acid 181 |
|---|---|---|---|
| Simian Herpesvirus Protein | 59/76* | | |
| Cladosporium gag Protein | | | 59/59 |
| Arabidopisis meri 5 | | | 65/71* |
| Rice Photosystem II | 35/35* | | |
| Cyanophora Photosystem II | 47/47* | | |
| Maize Photosystem II | 29/29* | | |
| Wheat Photosystem II | 29/29* | | |
| Shewanella Fumarate Reductase | 47/59 | | |
| Rubus Pyrophosphatase | 59/71* | | |
| Mouse Pax-1 Protein | 41/41 | | |
| Kluyveromyces g6p Isomerase | 41/51* | | |
| Cyanobacterium ATP Synthetase | 47/53 | | |
| Alcaligenes CnrB | 47/65 | | |
| Caenorhabditis C14B9.5 | 53/65 | | 41/65 |
| Synechococcus Protein | 47/53 | 29/41 | |
| Methylophilus DCM Dehalogenase | | 47/65 | |
| Drosophila | | 41/65 | 47/65 |
| Xylano Hydrolase | | 41/65* | |
| Curcurbita | | | 59/59 |
| Arabidopsis | | | 53/88* |
| Gallus BRM Protein | | | 35/53 |
| Impatiens Spot Virus | | | 41/76 |
| Phaseolus Tonoplast | | | 41/71 |

EXAMPLE 14

Use of Synthetic Peptides to Produce Monoclonals
Specific for Alpha Antigen of *M. avium*

In this example, an alternative approach to identification of MAC-specific secreted antigens was designed based on identification of species-specific epitopes of characterized antigens. The amino acid sequences of alpha antigens of *M. avium* and *M. tuberculosis* are compared in FIG. 19 (i.e., SEQ ID NOS: 1 and 2). As discussed in Example 13, extensive identity is apparent (87%).

In this study, two candidate sequences were identified which might confer species specific responses to *M. avium* alpha antigen. The first, (SEQ ID NO: 6) with the sequence "SYLASNKGVKRTGNAAV," begins at residue 147. The second (SEQ ID NO: 7), with the sequence "QRNDPSLHIPELVGH," begins at residue 229. To determine the potential for broad species specificity in these regions, searches were performed with these amino acid sequences using BLASTP to identify homologous sequences in the combined PDB, SwissProt, PIR, GenPept, and GPupdate databases at the NCBI as described for the above Example. The "expect" search parameter was increased from a default of 10 to 1000 to increase the reporting of even marginal matches.

As a control, a similar search was performed for a 17 amino acid intervening sequence (SEQ ID NO: 5), with the sequence "DQFIYAGSLSALLDPSQ," which begins at residue 181 of the *M. avium* alpha antigen sequence, and differs by only one amino acid from the homologous *M. tuberculosis* sequence (SEQ ID NO: 8). As indicated above, this stretch represents a consensus region.

The results of these three searches are shown in the following Tables. These data were divided into four tables. The first table (Table 7) shows the comparisons for strains of mycobacteria. The second table (Table 8) shows the comparisons for various potential human pathogens. The third table (Table 9) shows the comparisons for various human peptides. The fourth table (Table 10) shows the comparisons for peptides from other organisms.

The data in these Tables are displayed as the percent identity/homology between the target sequences and its best match in another species. Those matches with ≧65% identity or ≧80% homology are highlighted in bold. Items marked with an asterisk (*) required folding of at least one sequence for optimal alignment; the degree of homology of these matches is likely overestimated. No homologous sequences were identified for those entries left blank.

TABLE 7

Search Results for Peptides from Various Mycobacteria and
Three Peptide Sequences of Alpha Antigen of M. avium
(% identity/% homology)

|  | Amino Acid 147 | Amino Acid 229 | Amino Acid 181 |
|---|---|---|---|
| M. avium Alpha Antigen | 100/100 | 100/100 | 100/100 |
| M. intracellulare | 82/88 | 80/86 | 88/100 |
| Alpha Antigen | | | |
| M. bovis | | | |
| 85-A | 47/71 | 46/80 | 71/88 |
| 85-B | 47/82 | | 94/94 |
| 85-B | 47/82 | 53/80 | 94/94 |
| BCG Antigen | 47/71 | 46/80 | 71/88 |
| MPB51 | 47/76 | | 53/71 |
| MPB70/MPB80 | 41/53* | | |
| M. kansasii 85-B | 53/82 | 87/93 | 88/94 |
| M. leprae | | | |
| 85-A | 65/76 | | 76/82 |
| 85-B | 47/76 | 53/66 | 88/94 |
| 85-C | 64/76 | 53/73 | 59/71 |
| MPT51-like Protein | | | 53/71 |
| u1740g | | | 47/59 |
| M. scrofulaceum Alpha Antigen | 71/76 | 66/93 | 88/94 |
| M. tuberculosis | | | |
| 85-A | 47/71 | 46/80 | 71/88 |
| 85-B | 47/82 | 53/80 | 100/100 |
| 85-C | 64/82 | 53/73 | 59/71 |

TABLE 8

Search Results for Other Pathogens of
AIDS Patients and Three Peptide
Sequences of M. avium Alpha Antigen
(% identity/% homology)

|  | Amino Acid 147 | Amino Acid 229 | Amino Acid 181 |
|---|---|---|---|
| Aeromonas β-lactamase | | 47/60 | |
| Bacillus hypothetical 49.5 KD Protein | | 53/73* | |
| Bacillus L24 Gene Product | 41/47 | | |
| Bacillus ORFY | | 53/73* | |
| Bacillus Pbp 5 | | 53/73* | |
| Candida β-glucosidase | | | 53/65 |
| Chlamydia ItuA Gene Product | 47/71* | | |
| Clostridium Hypothetical Protein | 59/59* | | |
| Enterococcus Erythromycin Resistance | 41/65* | | |
| Enterococcus Serine Protease | 41/53 | | |
| E. coli Glutaredoxin 3 | 53/71* | | |

TABLE 8-continued

Search Results for Other Pathogens of AIDS Patients and Three Peptide Sequences of M. avium Alpha Antigen (% identity/% homology)

| | Amino Acid 147 | Amino Acid 229 | Amino Acid 181 |
|---|---|---|---|
| (GRX 3) | | | |
| E. coli pap Fimbrial Activator Protein | 29/59 | | |
| E. coli Hypothetical Protein f83 | 53/59* | | |
| E. coli Pantothenate Permease | | 40/53 | |
| Haemophilus Heme-Binding Protein | | | 47/59 |
| Haemophilus HhdA | 47/70 | | |
| Haemophilus Preprotein Translocase | | | 47/70 |
| Mycoplasma genitalium (random genomic) | | | 65/71* |
| Neisseria DTDP-Glucose-46-Dehydratase | | | 41/59 |
| Neisseria meningitidis UDP-Glucosyltransferase | | | 41/59 |
| Neisseria meningitidis UDP-Glucose-4-epimeras | | | 41/59 |
| Pseudomonas 3-methyl-2-oxobutanoate Dehydrogenase | | 33/40 | |
| Pseudomonas Alkaline Phosphatase H | | 40/60 | |
| Pseudomonas putida bkdA2 Protein | | 33/40 | |
| Saccharomyces ORF 233 Gene Product | 41/53 | | |
| Saccharomyces Hypothetical Protein Ykl | | 53/67* | |
| Saccharomyces Tubulin Suppressor | | 33/47 | |
| Saccharomyces Ubiquitin-activating Enzyme | | | 47/59 |
| Saccharomyces (Unknown Protein) | | 60/67* | |
| Salmonella DTDP-Glucose 46-Dehydratase | | | 47/70 |
| Schizosaccharomyces Hypothetical 26.9 kD | | | 35/65 |
| Schizosaccharomyces (Unknown Protein) | | 47/53 | |
| Shigella DTDP-Glucose 46-Dehydratase | | | 47/65 |
| Shigella rfbB Protein | | | 47/65 |
| Streptococcus faecalis plasmid pAM | 41/65* | | |
| Streptococcus agalactiae MSL | 41/65* | | |
| Streptomyces 3-Dehydroquinate Dehyrogenase | | 40/67* | |
| Streptomyces Hypothetical Protein 00929 | | 47/53 | |
| Streptomyces Phospho-N-acetyltransferase | | 40/67 | |
| Treponema Flagellar Filament Core Protein | 35/59 | | |
| Variola Major Core Protein p4b | 53/65* | | |

TABLE 9

Search Results for Human Peptides and Three Peptide Sequences of M. avium Alpha Antigen (% identity/% homology)

| | Amino Acid 147 | Amino Acid 229 | Amino Acid 181 |
|---|---|---|---|
| Band 3 Anion Transport Protein | | | 53/59* |
| Histidine Decarboxylase | | 47/47 | |
| Ig Kappa Light Chain (VJC) | 47/59* | | |
| MET Gene Product | 41/41 | | |
| Protein-Tyrosine-Phosphatase | | 47/60 | |
| Protein tyrosine phosphatase PTPH1 | | | 35/47 |
| T-cell Factor 1 Splice Form F | | 40/47 | |
| Transforming Protein (N-myc) | | 60/67* | |

TABLE 10

Search Results for Various Organisms and Three Peptide Sequences of M. avium Alpha Antigen (% identity/% homology)

| | Amino Acid 147 | Amino Acid 228 | Amino Acid 181 |
|---|---|---|---|
| Arabidopisis meri 5 | | | 53/65* |
| Caenorhabditis F52C9.3 Gene Product | | 40/60 | |
| Caenorhabditis C32D5.12 Gene Product | | | 53/76 |
| Caenorhabditis Hypothetical 53.4 KD Gene Product | | | 41/65 |
| Caenorhabditis LIN-9 Protein | 35/65 | | |
| Caenorhabditis ZK637.6 | 35/65 | | |
| Dioscorea Storage Protein | | | 47/71* |
| Dog Cytochrome C | 53/71* | | |
| Drosophila Furin 2 | | 53/60 | |
| Drosophila Homeobox Protein | 41/53* | | |
| Drosophila Kinesin-Like Protein | 47/71 | | |
| Drosophila Maternal Tudor Protein | | | 47/64 |
| Halobacterium Ribosomal Protein S8 | | 47/47* | |
| Hordeum Lipid Transfer Protein | 59/71* | | |
| Horse T-cell Antigen CD2 | | 60/80* | |
| Impatiens Virus M Polyprotein | | | 41/76 |
| Lamb's Quarters Hypothetical Protein | | | 47/65* |
| Metalloproteinase Inhibitor | 65/76* | | |
| Methanosarcina vhtC Gene Product | | 33/60* | |
| Mouse Metalloproteinase Inhibitor 1 | 65/76* | | |
| Populous cellulase | 43/59 | | |
| Rat Dodecenoyl-CoA-Delta Isomerase | 41/59* | | |
| Rat Lactogen Receptor 1 | | 47/60 | |
| Rat Prolactin Receptor 2 | | 47/60 | |
| Rhodococcus Lipoprotein | | | 47/59 |
| Rice Cysteine Proteinase Inhibitor | 47/71 | | |
| Seal Cytochrome C | 53/71* | | |
| Spinacia Phosphoglucomutase | | | 41/70 |
| Strawberry Virus Coat Protein | | 47/53 | |
| Styela Homeobox Protein | | 47/53* | |
| Stylonychia DNA Polymerase II | | 47/53 | |

TABLE 10-continued

Search Results for Various Organisms and
Three Peptide Sequences of M. avium Alpha Antigen
(% identity/% homology)

|  | Amino Acid 147 | Amino Acid 228 | Amino Acid 181 |
|---|---|---|---|
| Synechocystis Hypothetical Protein | 41/53 | 53/67 | 41/53 |
| Tobacco Superoxide Dismutase | 47/71* | | |
| Tomato Virus M Polyprotein | | | 41/65 |
| Xenopus Activin Beta B Subunit | | 53/67 | 41/59 |

As shown in the above Tables, the potentially species-specific sequences generally established a high degree of similarity only with *M. intracellulare*, a member of the MAC complex, and with *M. scrofulaceum*, an uncommon pathogen. Little similarity was noted with proteins of other species.

An additional directed search was performed to compare these same three *M. avium* sequences with the PS 1 secreted antigen of the corynebacteria, which is a protein of approximately 30 kD, and which may be a member of the alpha antigen family (G. Joliff et al, "Cloning and nucleotide sequence of the csp1 gene encoding PS1, one of the two major secreted proteins of *Corynebacterium glutamicum*: the deduced N-terminal region of PS1 is similar to the Mycobacterium antigen 85 complex," Mol. Microbiol., 6:2349–2362 [1992]). The same methods were used in making these comparisons as described above. The results of this study indicated only that there was only 24% identity and 40% homology, suggesting that cross-reactivity between the *M. avium* alpha antigen and that of the corynebacteria was unlikely.

EXAMPLE 15

*M. avium* Alpha Antigen Peptide Sequences

Based on the analysis performed in Examples 13 and 14, peptides were synthesized representing two potentially species-specific sequences of *M. avium* alpha antigen. The first of these sequences was "SYLASNKGVKRTGNAAV" (SEQ ID NO: 6), which begins at residue 147. The second sequence was "QRNDPSLHIPELVGH" (SEQ ID NO: 7), which begins at residue 229. The peptides were synthesized on 1µ polystyrene microparticles by the commercial MacroMolecular Structure Analysis Facility of the University of Kentucky, Lexington, Ky.

In the synthesis of peptides, peptides are ordinarily cleaved from the solid support at the completion of the synthesis. However, for the purpose of immunization, allowing the peptides to remain on the beads may offer several advantages. First, the particles themselves have a modest adjuvant effect, and they may be injected intrasplenically directly (without use of nitrocellulose particles).

Two groups of mice as described in Example 6, above were immunized with these peptides using both intrasplenic and conventional protocols as described in Example 6 above. One animal from each group was bled to test for development of serum antibody against the peptides. One antibody preparation which recognized the native 30 kD alpha antigen and no other proteins in *M. avium* filtrate was obtained with immunization with the 229 peptide. Western blots of serum from these mice are shown in FIG. 20. These Westerns were prepared in the same manner as described for Example 1.

In addition to these preparations, it is contemplated that additional monoclonal and/or polyclonal antibodies be prepared that are usefull in the present invention.

EXAMPLE 16

Comparison of the Reactivity of K-II Serum and Anti-Alpha Antigen Antibody

In this example, a series of immunoabsorption studies were conducted to demonstrate that one of the antigens recognized by the K-II (or "Kris") serum described by Sippola et al. (Sippola et al., "*Mycobacterium avium* antigenuria in patients with AIDS and disseminated *M. avium* disease," J. Infect. Dis., 168:466–8 [1993]) is alpha antigen, as well as to show that the 22.5 kD to 25 kD protein present in *M. avium* filtrates, is not present in *M. tuberculosis* filtrates.

To prepare the K-II serum, an adult goat was immunized by an initial injection of an emulsion of 1 ml incomplete Freund's adjuvant (Difco) 10 mg heat-killed, dried *M. intracellulare* serotype 5 (ATCC 35768), and 10 mg dried culture filtrate of *M. intracellulare* serotype 5, propagated and prepared as described above in Example 1 with glucose added to the medium. The animal was boosted twice with injection of the same quantity of *M. intracellulare* culture filtrate.

In this example, Western blots of culture filtrates of *M. avium* and *M. tuberculosis* were used to demonstrate the reactivity of the K-II antiserum, and the antibodies produced in Example 2. The Western blot analysis was performed as described above in Example 1. The K-II serum was either used diluted 1:5000 in TBS, or was pretreated by addition of 100 µg *M. tuberculosis* culture filtrate per 5 ml of diluted antiserum, incubated 4 hr at room temperature prior to use in Western blot.

The results of this study are shown in the Western blots of FIGS. 21 (panels A–C) and 22. As shown in these blots, an *M. avium*-specific protein recognized by the Kris ("K-II") serum migrated with a molecular size of approximately 25 kD. This results suggests a potential role for this protein in antigen detection studies for diagnosis of MAC infection and disease.

Several *M. avium* protein antigens in this molecular weight range have been identified and cloned on the basis of homology with other species. These include a 27 kD *M. tuberculosis* lipoprotein (J. Nair et al., "Nucleotide sequence analysis and serologic characterization of a 27-kilodalton *Mycobacterium intracellulare* lipoprotein," Infect. Immun., 61:1074–81[1993]), and 22 and 19 kD proteins found in *M. tuberculosis* and *M. leprae* (D. P. Harris et al., "Epitope specificity and isoforms of the mycobacterial 19-kilodalton antigen," Infect. Immun., 62:2963–72 [1994]; R. J. Booth et al., "Homologs of *Mycobacterium leprae* 18-kilodalton and *Mycobacterium tuberculosis* 19-kilodalton antigens in other mycobacteria," Infect. Immun., 61:1509–15 [1993]; and S. L. Morris et al., "Isolation and characterization of recombinant lambda gt11 bacteriophages expressing four different *Mycobacterium intracellulare* antigens," Infect. Immun., 58:17–20 [1990]). However, the degree of homology with *M. tuberculosis* in these antigens make it unlikely that any of these represent the MAC-specific Kris antigen.

EXAMPLE 17

*M. avium* 25 kD Protein

In this Example, the identity of the 25 kD protein identified in Example 16 above is investigated in order to determine its potential role in immunodiagnosis of MAC infection. The intraspelenic protocol described in Example 2 is used to produce monoclonal antibodies directed against this protein, and hybridomas are screened for reactivity against *M. avium* filtrate. Those which score positive are then tested for lack of reactivity against *M. tuberculosis* filtrate. Those which appear to be specific for *M. avium* are expanded in culture, biotinylated, and evaluated in the antigen detection assay, as described in Example 3, with the exception that these antibodies substitute for TBC-27.

In additional experiments, K-II serum preadsorbed against the monoclonal antibody is substituted for the BCG antiserum. As K-II serum is a goat antiserum, the secondary antibody used here is an anti-goat antibody, rather than the anti-rabbit antibody used in the previous Examples.

These Examples clearly show that the amplified ELISA system of the present invention can be used to detect urinary mycobacterial antigen in patients with latent and active infection. The test is potentially valuable for diagnosis of tuberculosis because it can be applied to fluids remote from the site of active infection. It is rapid, inexpensive and technically straightforward, and thus has potential application in less-developed regions of the world where laboratory facilities and fmancial resources for tuberculosis control are limited. It has the added advantage that an additional clinic visit (for skin test reading) is not required. The assay may be useful in diagnosis of latent infection in persons in whom PPD skin testing is unreliable, as it detects microbial products rather than measuring the host response. Finally, since the assay detects a secreted (rather than cell-associated) antigen, its decline during therapy of either latent of active infection may be a useful, early marker of treatment success. Lastly, this is the only method currently described which can potentially be used to monitor the effectiveness of preventive therapy.

In summary, the present invention provides numerous advances and advantages over the prior art, including: (1) much greater sensitivity, (2) much greater safety, as there is no spillage, nor aerosolization of bacterial cultures during biochemical testing methods; and (3) the overall process for performing multiple tests is extremely simple and efficient, requiring very little labor on the part of the microbiologist. All of these advantages enhance the speed and accuracy of scoring test results in studies to detect *M. tuberculosis* infection and disease.

What is claimed is:

1. A method for identification of *Mycobacterium tuberculosis* in a sample comprising:

a) providing:

i) a monoclonal antibody directed against an epitope on a portion of alpha antigen of *Mycobacterium tuberculosis,* wherein said antibody is not reactive with alpha antigen of *Mycobacterium avium;* ii) a sample suspected of containing at least a portion of said alpha antigen of *Mycobacterium tuberculosis;* and b) adding said sample to said monoclonal antibody under conditions such that said antibody binds to said epitope of said portion of said alpha antigen of *Mycobacterium tuberculosis,* to form an antibody-antigen complex, and c) detecting said antibody-antigen complex, under conditions such that the presence of *Mycobacterium tuberculosis* is detected, wherein said detecting is selected from the group consisting of enzyme immunoassay, radioimmunoassay, fluorescence immunoassay, flocculation, particle agglutination, and in situ chromogenic assay.

2. The method of claim 1, wherein said detecting comprises adding a primary antibody to said antigen-antibody complex so that said primary antibody binds to said antigen to form an antibody-antigen-antibody sandwich.

3. The method of claim 2, wherein said detecting further comprises adding a reporter reagent, wherein said reporter reagent comprises an antibody reporter, to said antibody-antigen-antibody sandwich to form an antibody-antigen-antibody-antibody sandwich.

4. The method of claim 3, wherein said detecting further comprises adding an amplifier to said antibody-antigen-antibody-antibody sandwich.

5. The method of claim 1, wherein said monoclonal antibody comprises a murine monoclonal antibody.

6. The method of claim 5, wherein said murine monoclonal antibody is biotinylated.

7. A method for identification of *Mycobacterium tuberculosis* in a sample comprising:
   a) providing:
      i) a monoclonal antibody directed against an epitope on a portion of alpha antigen of *Mycobacterium tuberculosis,* wherein said antibody is not reactive with alpha antigen of *Mycobacterium avium;*
      ii) a sample suspected of containing at least a portion of alpha antigen of *Mycobacterium tuberculosis;*
   b) adding said sample to said monoclonal antibody under conditions such that said antibody binds to said epitope on said portion of said alpha antigen of *Mycobacterium tuberculosis,* in said sample to form an antibody-antigen complex; and
   c) detecting said antibody-antigen complex, wherein said detecting is selected from the group consisting of enzyme immunoassay, radioimmunoassay, fluorescence immunoassay, flocculation, particle agglutination, and in situ chromogenic assay.

8. The method of claim 7, wherein said detecting comprises adding a primary antibody to said antigen-antibody complex so that said primary antibody binds to said antigen to form an antibody-antigen-antibody sandwich.

9. The method of claim 8, wherein said detecting further comprises adding a reporter reagent, wherein said reporter reagent comprises an antibody reporter, to said antibody-antigen-antibody sandwich to form an antibody-antigen-antibody-antibody sandwich.

10. The method of claim 9, wherein said detecting further comprises adding an amplifier to said antibody-antigen-antibody-antibody sandwich.

11. The method of claim 7, wherein said monoclonal antibody comprises a murine monoclonal antibody.

12. The method of claim 11, wherein said murine monoclonal antibody is biotinylated.

* * * * *

```
                        SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 325 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO:1:

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160
```

```
Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
                260                 265                 270

Val Arg Ser Ser Asn Leu Lys Phe Gln Asp Ala Tyr Asn Ala Ala Gly
                275                 280                 285

Gly His Asn Ala Val Phe Asn Phe Pro Pro Asn Gly Thr His Ser Trp
                290                 295                 300

Glu Tyr Trp Gly Ala Gln Leu Asn Ala Met Lys Gly Asp Leu Gln Ser
305                 310                 315                 320

Ser Leu Gly Ala Gly
                325

(2) INFORMATION FOR SEQ ID NO:2:

(i) SEQUENCE CHARACTERISTICS:
        (A) LENGTH: 330 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:2:

Met Thr Asp Leu Ser Glu Lys Val Arg Ala Trp Gly Arg Arg Leu Leu
1               5                   10                  15

Val Gly Ala Ala Ala Val Thr Leu Pro Gly Leu Ile Gly Leu Ala
            20                  25                  30

Gly Gly Ala Ala Thr Ala Asn Ala Phe Ser Arg Pro Gly Leu Pro Val
            35                  40                  45

Glu Tyr Leu Gln Val Pro Ser Ala Gly Met Gly Arg Asp Ile Lys Val
    50                  55                  60

Gln Phe Gln Ser Gly Gly Asn Gly Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Val Ile Met Pro Val
                100                 105                 110

Gly Gly Gln Ser Ser Phe Tyr Ala Asp Trp Tyr Gln Pro Ala Cys Gly
            115                 120                 125

Lys Ala Gly Cys Ser Thr Tyr Lys Trp Glu Thr Phe Leu Thr Ser Glu
130                 135                 140

Leu Pro Ser Tyr Leu Ala Ser Asn Lys Gly Val Lys Arg Thr Gly Asn
145                 150                 155                 160

Ala Ala Val Gly Ile Ser Met Ser Gly Ser Ala Met Ile Leu Ala
                165                 170                 175
```

```
Val Asn His Pro Asp Gln Phe Ile Tyr Ala Gly Ser Leu Ser Ala Leu
        180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Asp Ala Met Trp Gly Pro Ser Ser
        210                 215                 220

Asp Pro Ala Trp Gln Arg Asn Asp Pro Ser Leu His Ile Pro Glu Leu
225                 230                 235                 240

Val Gly His Asn Thr Arg Leu Trp Leu Tyr Cys Gly Asn Gly Thr Pro
                245                 250                 255

Ser Glu Leu Gly Gly Ala Asn Met Pro Ala Glu Phe Leu Glu Asn Phe
        260                 265                 270

Val Arg Ser Ser Asn Leu Lys Phe Gln Asp Ala Tyr Asn Gly Ala Gly
        275                 280                 285

Gly His Asn Ala Val Phe Asn Phe Asn Ala Asn Gly Thr His Ser Trp
        290                 295                 300

Glu Tyr Trp Gly Ala Gln Leu Asn Ala Met Lys Pro Asp Leu Gln Gly
305                 310                 315                 320

Thr Leu Gly Ala Ser Pro Gly Gly Gly
                325                 330

(2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:3:

Gln Trp Leu Ser Ala Asn Arg Ala Val Lys Pro Thr Gly Ser Ala Ala
1               5                   10                  15

Ile (2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:4:

Glu Arg Asn Asp Pro Thr Gln Gln Ile Pro Lys Leu Val Ala Asn
1               5                   10                  15

(2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

Asp Gln Phe Ile Tyr Ala Gly Ser Leu Ser Ala Leu Leu Asp Pro Ser
```

-continued

```
1               5                   10                  15

Gln (2) INFORMATION FOR SEQ ID NO:6:

(i) SEQUENCE CHARACTERISTICS:
          (A) LENGTH: 17 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO:6:

Ser Tyr Leu Ala Ser Asn Lys Gly Val Lys Arg Thr Gly Asn Ala Ala
1               5                   10                  15

Val (2) INFORMATION FOR SEQ ID NO:7:

(i) SEQUENCE CHARACTERISTICS:
          (A) LENGTH: 15 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO:7:

Gln Arg Asn Asp Pro Ser Leu His Ile Pro Glu Leu Val Gly His
1               5                   10                  15

(2) INFORMATION FOR SEQ ID NO:8:

(i) SEQUENCE CHARACTERISTICS:
          (A) LENGTH: 17 amino acids
          (B) TYPE: amino acid
          (C) STRANDEDNESS: Not Relevant
          (D) TOPOLOGY: Not Relevant (ii) MOLECULE TYPE: peptide (xi) SEQUENCE DESCRIPTION: SEQ ID NO:8:

Gln Gln Phe Ile Tyr Ala Gly Ser Leu Ser Ala Leu Leu Asp Pro Ser
1               5                   10                  15
Gln
```